(12) United States Patent
Livak et al.

(10) Patent No.: US 9,353,406 B2
(45) Date of Patent: May 31, 2016

(54) UNIVERSAL PROBE ASSAY METHODS

(75) Inventors: Kenneth J. Livak, San Jose, CA (US);
Jason A. A. West, Pleasanton, CA (US);
Robert C. Jones, Los Altos, CA (US)

(73) Assignee: Fluidigm Corporation, South San Francisco, CA (US)

(*) Notice: Subject to any disclaimer, the term of this patent is extended or adjusted under 35 U.S.C. 154(b) by 39 days.

(21) Appl. No.: 13/280,214

(22) Filed: Oct. 24, 2011

(65) Prior Publication Data
US 2012/0115143 A1 May 10, 2012

Related U.S. Application Data

(60) Provisional application No. 61/439,325, filed on Feb. 3, 2011, provisional application No. 61/406,066, filed on Oct. 22, 2010.

(51) Int. Cl.
*C12Q 1/68* (2006.01)

(52) U.S. Cl.
CPC ........................................ *C12Q 1/682* (2013.01)

(58) Field of Classification Search
None
See application file for complete search history.

(56) References Cited

U.S. PATENT DOCUMENTS

| | | | |
|---|---|---|---|
| 6,540,895 B1 | 4/2003 | Spence et al. | |
| 6,885,982 B2 | 4/2005 | Harris et al. | |
| 6,951,632 B2 | 10/2005 | Unger et al. | |
| 7,042,649 B2 | 5/2006 | Quake et al. | |
| 7,059,348 B2 | 6/2006 | Nat | |
| 7,062,418 B2 | 6/2006 | Lee et al. | |
| 7,097,809 B2 | 8/2006 | Dam et al. | |
| 7,161,736 B2 | 1/2007 | Legrand et al. | |
| 7,192,629 B2 | 3/2007 | Lammertink et al. | |
| 7,217,367 B2 | 5/2007 | Huang et al. | |
| 7,232,109 B2 | 6/2007 | Driggs et al. | |
| 7,248,413 B2 | 7/2007 | Quake et al. | |
| 7,262,923 B2 | 8/2007 | Quake et al. | |
| 7,279,146 B2 | 10/2007 | Nassef | |
| 7,291,512 B2 | 11/2007 | Unger | |
| 7,294,503 B2 | 11/2007 | Quake et al. | |
| 7,368,163 B2 | 5/2008 | Huang et al. | |
| 7,442,556 B2 | 10/2008 | Manger et al. | |
| 7,476,363 B2 | 1/2009 | Unger et al. | |
| 7,526,741 B2 | 4/2009 | Lee et al. | |
| 7,604,965 B2 | 10/2009 | McBride et al. | |
| 7,666,361 B2 | 2/2010 | McBride et al. | |
| 7,678,547 B2 | 3/2010 | Eyal et al. | |
| 7,691,333 B2 | 4/2010 | McBride et al. | |
| 7,749,737 B2 | 7/2010 | McBride et al. | |
| 7,792,345 B2 | 9/2010 | Taylor et al. | |
| 7,815,868 B1 | 10/2010 | Jones et al. | |
| 7,820,427 B2 | 10/2010 | Unger et al. | |
| 7,833,708 B2 | 11/2010 | Enzelberger et al. | |
| 7,837,946 B2 | 11/2010 | McBride et al. | |
| 2002/0006617 A1* | 1/2002 | Fan et al. | 435/6 |
| 2003/0119004 A1* | 6/2003 | Wenz et al. | 435/6 |
| 2004/0180377 A1 | 9/2004 | Manger et al. | |
| 2005/0053952 A1 | 3/2005 | Hong et al. | |
| 2005/0272071 A1* | 12/2005 | Lao et al. | 435/6 |
| 2006/0014183 A1* | 1/2006 | Pfundheller et al. | 435/6 |
| 2006/0172408 A1 | 8/2006 | Quake et al. | |
| 2006/0233674 A1 | 10/2006 | Nelson | |
| 2006/0281183 A1 | 12/2006 | Sun et al. | |
| 2007/0134807 A1 | 6/2007 | Bao et al. | |
| 2007/0224617 A1 | 9/2007 | Quake et al. | |
| 2007/0248971 A1 | 10/2007 | Maerkl et al. | |
| 2008/0050283 A1 | 2/2008 | Chou et al. | |
| 2008/0075380 A1 | 3/2008 | Dube et al. | |
| 2008/0108063 A1 | 5/2008 | Lucero et al. | |
| 2008/0129736 A1 | 6/2008 | Sun et al. | |
| 2008/0176211 A1 | 7/2008 | Spence et al. | |
| 2008/0223721 A1 | 9/2008 | Cohen et al. | |
| 2008/0230387 A1 | 9/2008 | McBride et al. | |
| 2008/0264863 A1 | 10/2008 | Quake et al. | |
| 2008/0274493 A1 | 11/2008 | Quake et al. | |
| 2008/0281090 A1 | 11/2008 | Lee et al. | |
| 2008/0292504 A1 | 11/2008 | Goodsaid et al. | |
| 2009/0018195 A1 | 1/2009 | Balagadde | |
| 2009/0069194 A1 | 3/2009 | Ramakrishnan | |

(Continued)

FOREIGN PATENT DOCUMENTS

| | | |
|---|---|---|
| WO | 01/67369 A2 | 9/2001 |
| WO | 2007/033385 A2 | 3/2007 |
| WO | 2007/044091 A2 | 4/2007 |
| WO | 2008/043046 A2 | 4/2008 |
| WO | WO 2008104794 A2 * | 9/2008 |
| WO | 2009/100449 A1 | 8/2009 |
| WO | 2010/011852 A1 | 1/2010 |
| WO | 2010/017210 A1 | 2/2010 |
| WO | 2010/077618 A1 | 7/2010 |
| WO | 2011/053790 A2 | 5/2011 |

OTHER PUBLICATIONS

Tsourkas et al. Nucleic Acids Research (2002) 30(19): 4208-4215.*
Livak, "Allelic discrimination using fluorogenic probes and the 5' nuclease assay, Genetic Analysis", Biomolecular Engineering, Feb. 1999, vol. 14, No. 5-6, p. 143-149.

*Primary Examiner* — Angela M Bertagna
(74) *Attorney, Agent, or Firm* — Kilpatrick Townsend & Stockton LLP

(57) ABSTRACT

Reagents and methods are provided for detecting the presence of a target polynucleotide in a sample are disclosed. In one aspect, a method for producing a labeled amplification product by amplifying a target nucleic acid sequence to produce an amplification product comprising the target sequence, a first probe-binding sequence 5' to the target sequence, and a second probe-binding sequence 3' to the target sequence, thereby producing an amplification product; and hybridizing a first detection probe to the amplification product, the first detection probe comprising a first segment that hybridizes to the first probe-binding sequence and a second segment that hybridizes to the second probe-binding sequence, thereby producing a labeled amplification product is disclosed.

26 Claims, 37 Drawing Sheets

(56) References Cited

U.S. PATENT DOCUMENTS

| | | |
|---|---|---|
| 2009/0142236 A1 | 6/2009 | Unger et al. |
| 2009/0147918 A1 | 6/2009 | Fowler et al. |
| 2009/0168066 A1 | 7/2009 | Hansen et al. |
| 2009/0239308 A1 | 9/2009 | Dube et al. |
| 2009/0291435 A1 | 11/2009 | Unger et al. |
| 2010/0006437 A1 | 1/2010 | Barany et al. |
| 2010/0104477 A1 | 4/2010 | Liu et al. |
| 2010/0120018 A1 | 5/2010 | Quake et al. |
| 2010/0120077 A1 | 5/2010 | Daridon |
| 2010/0124765 A1 | 5/2010 | Lao et al. |
| 2010/0154890 A1 | 6/2010 | Maerkl et al. |
| 2010/0166608 A1 | 7/2010 | Quan et al. |
| 2010/0171954 A1 | 7/2010 | Quake et al. |
| 2010/0183481 A1 | 7/2010 | Facer et al. |
| 2010/0184202 A1 | 7/2010 | McBride et al. |
| 2010/0187105 A1 | 7/2010 | Unger et al. |
| 2010/0196892 A1 | 8/2010 | Quake et al. |
| 2010/0197522 A1 | 8/2010 | Liu et al. |
| 2010/0200782 A1 | 8/2010 | Unger et al. |
| 2010/0230613 A1 | 9/2010 | Pieprzyk et al. |
| 2010/0263732 A1 | 10/2010 | Hansen et al. |
| 2010/0263757 A1 | 10/2010 | Fernandes et al. |
| 2010/0311060 A1 | 12/2010 | Facer et al. |
| 2010/0320364 A1 | 12/2010 | Unger et al. |

\* cited by examiner

A)
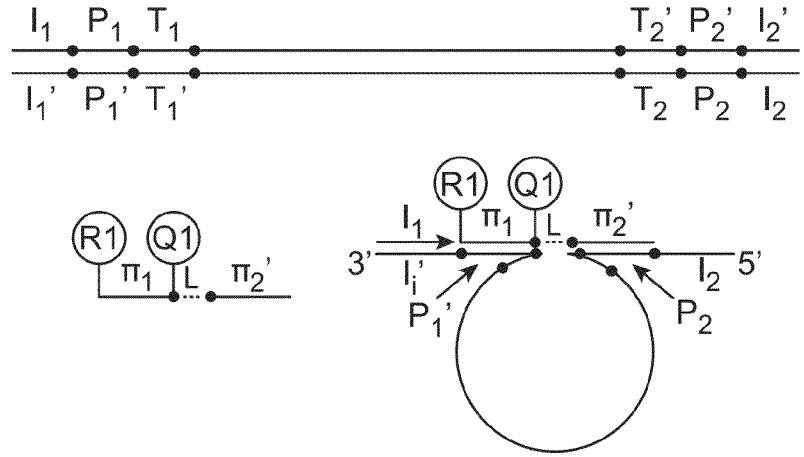
B)
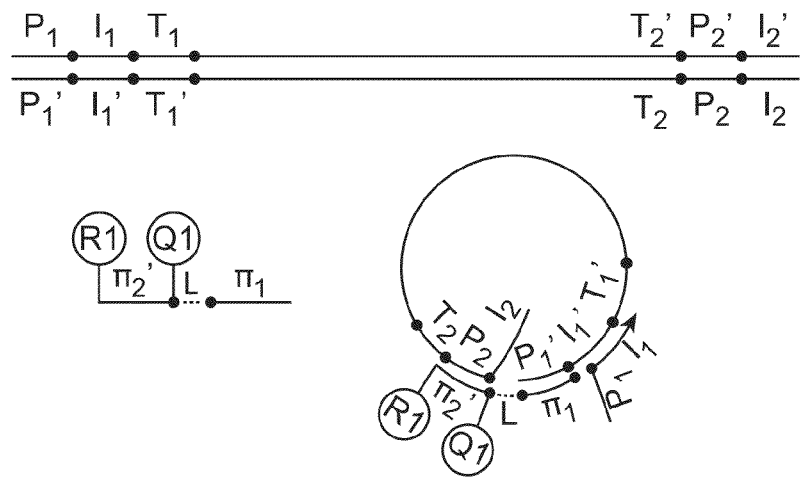
C)
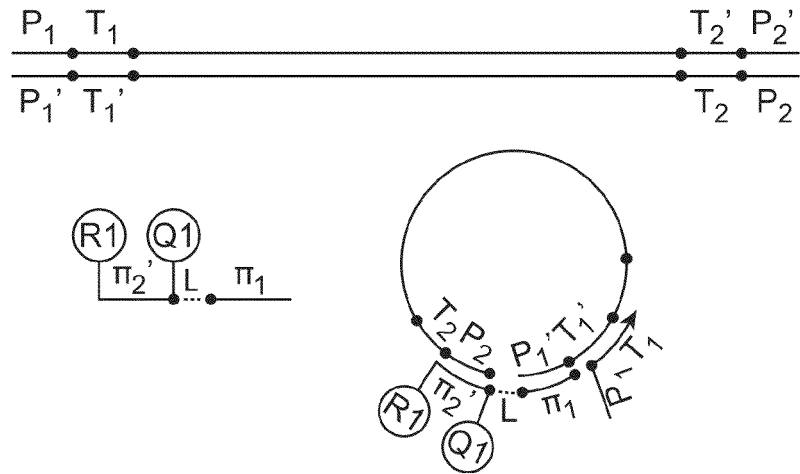
FIG. 4

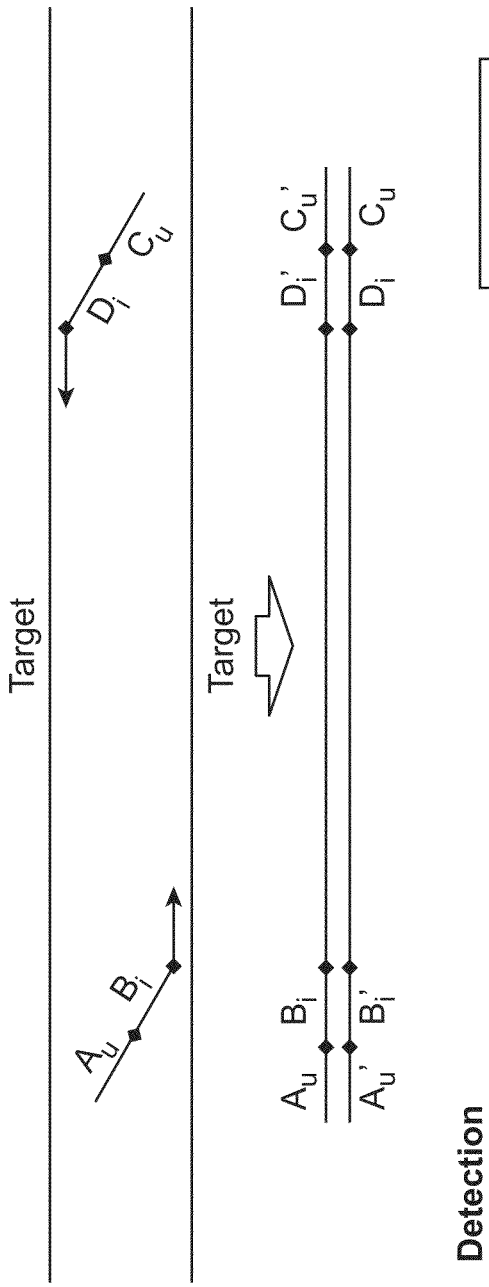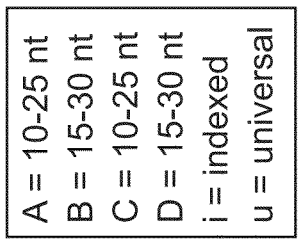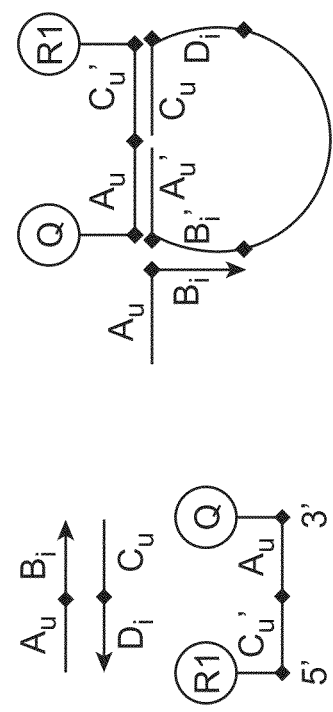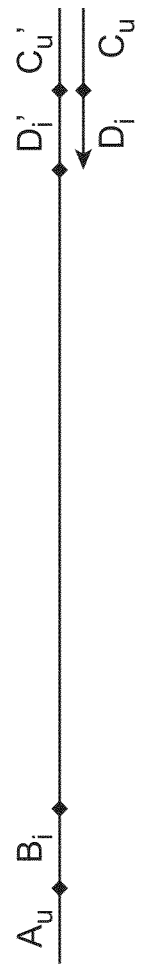
FIG. 16

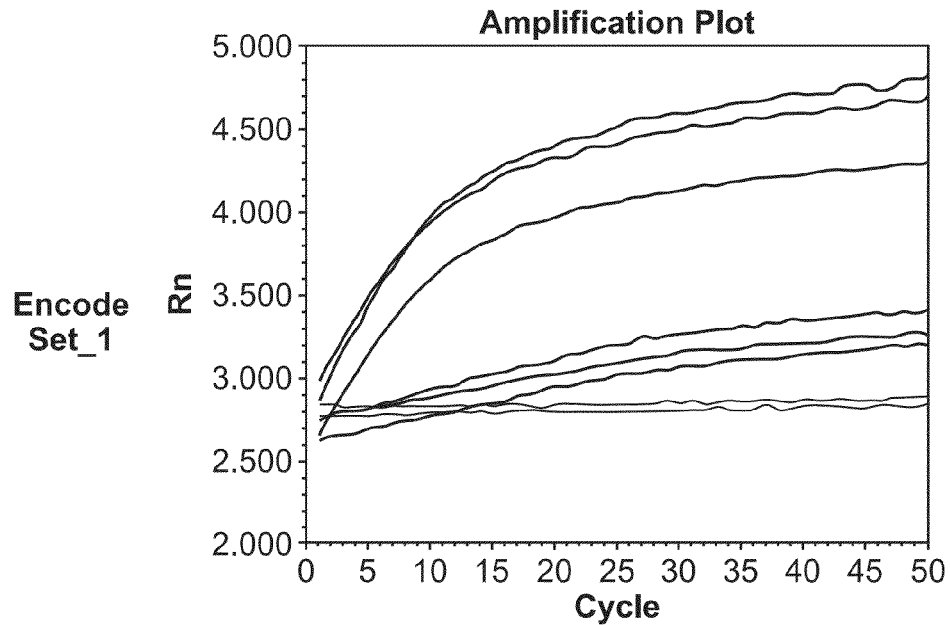
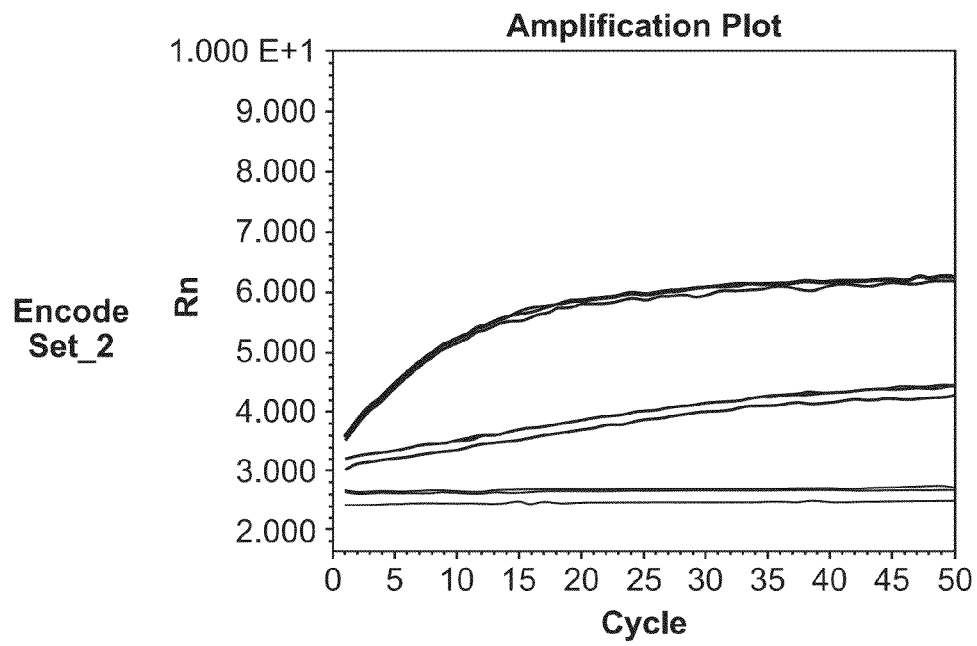
FIG. 31

Amplification Plot
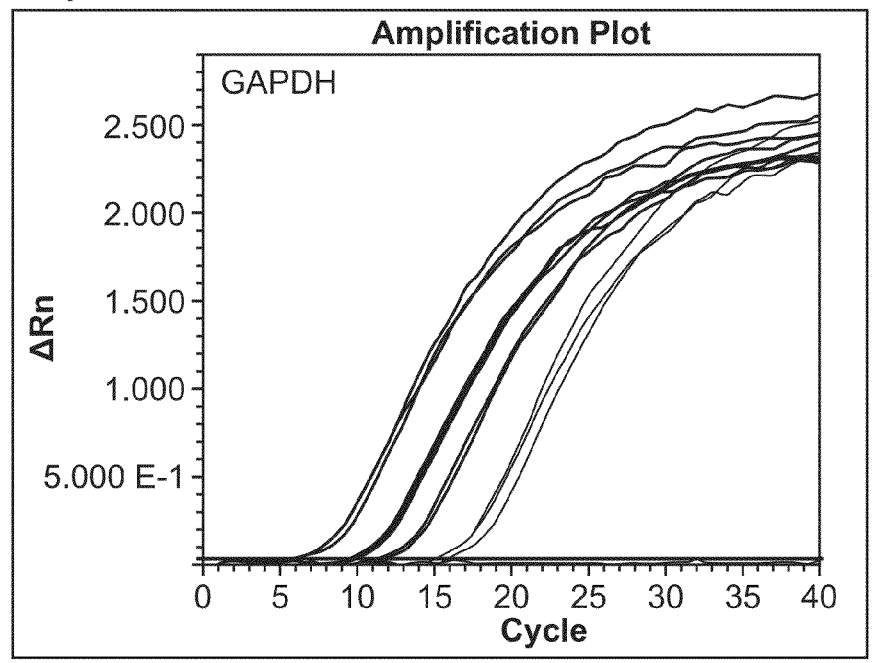
Amplification Plot
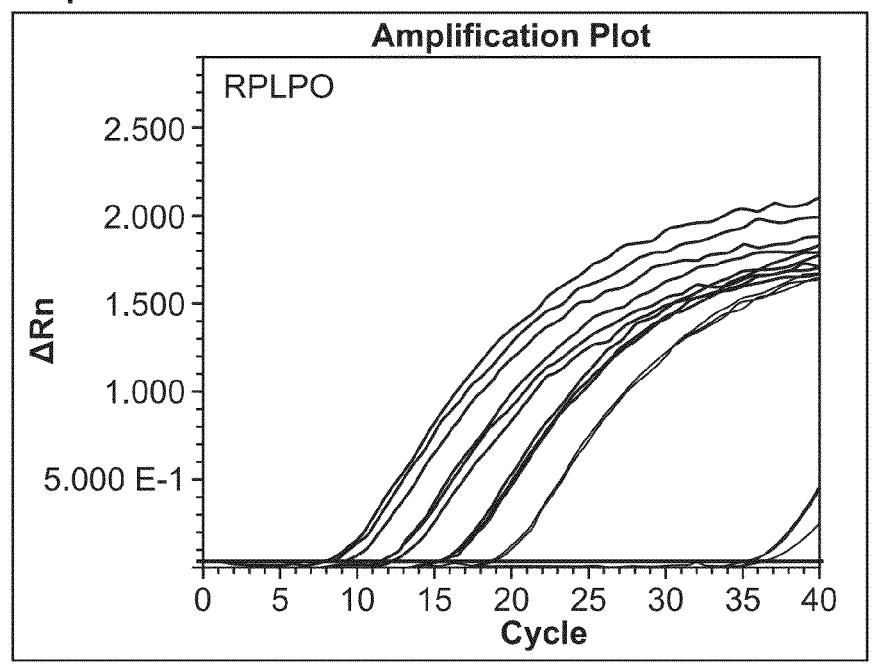
FIG. 33

A) OuroBoros Data
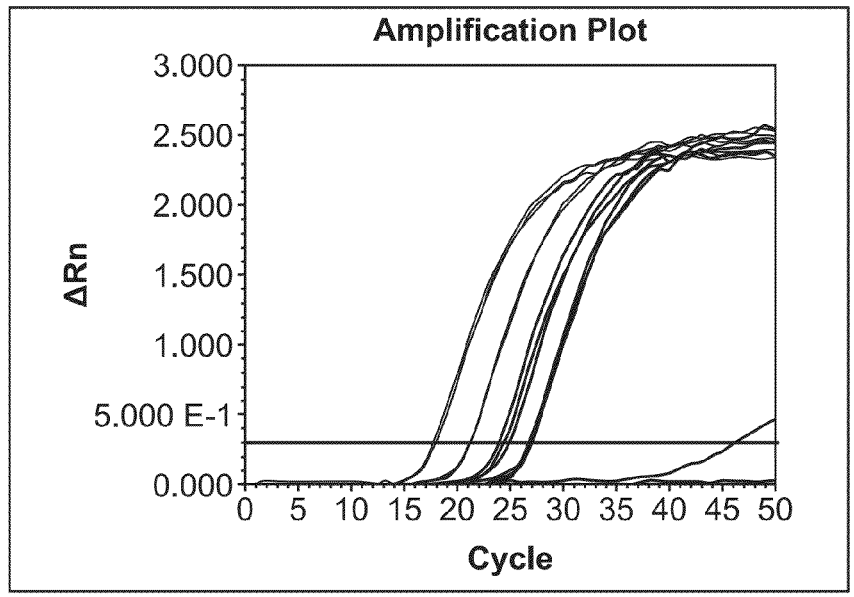
B) (SimpleBoros data with reverse decode primer)
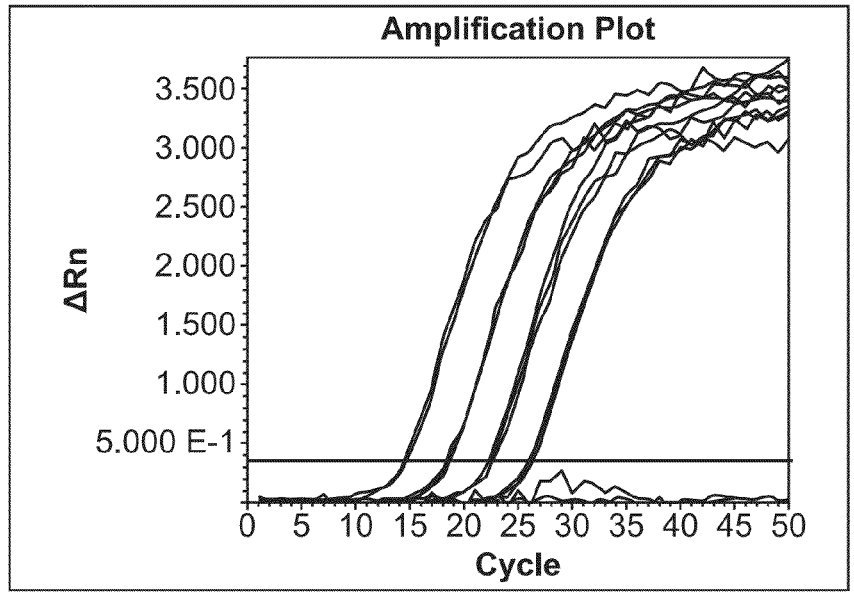
FIG. 34

UNIVERSAL PROBE ASSAY METHODS

CROSS-REFERENCE TO RELATED APPLICATIONS

This application claims the benefit of U.S. Provisional Application Nos. 61/439,325, filed Feb. 3, 2011, and 61/406,066, filed Oct. 22, 2010, each of which is incorporated herein by reference in its entirety and for all purposes.

REFERENCE TO A "SEQUENCE LISTING," A TABLE, OR A COMPUTER PROGRAM LISTING APPENDIX SUBMITTED AS AN ASCII TEXT FILE

The Sequence Listing written in file 85665-823497_ST25.TXT, created on Oct. 25, 2011, 3,625 bytes, machine format IBM-PC, MS-Windows operating system, is hereby incorporated by reference.

FIELD OF THE INVENTION

The invention relates to nucleic acid assays and finds application in the fields of genetics, medicine, and agriculture.

BACKGROUND

The high cost of fluorogenic probes used in quantitative PCR (qPCR) assays has prompted schemes that use "Universal Probes." A Universal Probe, sometimes called a "Universal Template Probe," is a generic fluorogenic probe that can be used to generate signal in qPCR assays by recognizing non-template specific sequences introduced into amplification products. One of the advantages of this method is that different target DNA sequences can be detected employing the same labeled probe, which substantially reduces the cost of real-time PCR set-up. One example, described by Zhang et al., 2003, *Nucl. Acids Res.* 31:e123, is a TaqMan™ probe that recognizes an approximately 20 base sequence from the 5' end of a PCR primer. U.S. Pat. Nos. 7,153,658 and 7,601,821 describe variations of this scheme by adding a generic set of primers to the Universal Probe. In these approaches, a multiplex ligation reaction is performed to associate each specific target segment with its own pair of encoding PCR primers.

BRIEF SUMMARY OF THE INVENTION

In one aspect, the disclosure provides a method for producing a labeled amplification product by amplifying a target nucleic acid sequence to produce an amplification product comprising the target sequence, a first probe-binding sequence 5' to the target sequence, and a second probe-binding sequence 3' to the target sequence, thereby producing an amplification product; and hybridizing a first detection probe to the amplification product, said first detection probe comprising a first segment that hybridizes to the first probe-binding sequence and a second segment that hybridizes to the second probe-binding sequence, thereby producing a labeled amplification product is disclosed. In one approach, the target nucleic acid sequence is amplified by the polymerase chain reaction or the ligase chain reaction. In one approach the first detection probe comprises a fluorescent dye (for example the first detection probe may be a fluorescence resonance energy transfer (FRET) probe comprising a reporter dye and a quencher dye). In one approach the detection probe is a molecular beacon probe. In one approach, the target nucleic acid sequence is one of a plurality of distinct target nucleic acid sequences in a sample.

In one approach, the method further includes combining the labeled amplification product with a first primer under conditions in which said primer anneals to the amplification product and is extended by a DNA polymerase with 5' nuclease activity, wherein said extension causes the release of the reporter dye or the quencher dye from the first detection probe or causes the release of the detection probe from the labeled amplification product. The method may include additional rounds of amplification of the target sequence, for example, additional rounds of PCR amplification with the first primer and a reverse primer.

In one approach, the method further includes producing a second labeled amplification product by amplifying a second target nucleic acid sequence to produce a second amplification product comprising said second target sequence, a third probe-binding sequence 5' to the second target sequence, and a fourth probe-binding sequence 3' to the second target sequence, thereby producing a second amplification product; and hybridizing a second detection probe to the second amplification product, said second probe comprising a first segment that hybridizes to the third probe-binding sequence and a second segment that hybridizes to the fourth probe-binding segment, thereby producing a second labeled amplification product. In one approach the third probe-binding sequence is the same as the first probe-binding sequence and the fourth probe-binding sequence is the same as the second probe-binding sequence and a single detection probe binds both the first and second amplification products. In one approach the third probe-binding sequence is not the same as the first probe-binding sequences and/or the fourth probe-binding sequence is not the same as the second-probe binding sequence. The first and second detection probes comprise different reporter dyes.

In one aspect, the disclosure provides a method comprising (a) combining (1) a target polynucleotide; (2) a first encoding primer, wherein the first encoding primer comprises a first target-binding sequence complementary to and capable of binding to a first primer-binding sequence (PBS) of the target polynucleotide and a first probe-binding sequence not complementary to the target polynucleotide sequence at a position adjacent to said first PBS; and (3) a second encoding primer, wherein the second encoding primer comprises a second target-binding sequence complementary to and capable of binding to a second PBS of the target polynucleotide and a second probe-binding sequence not complementary to the target polynucleotide sequence at a position adjacent to said second PBS; (b) exposing the combination produced in step (a) to amplification conditions, thereby producing amplicons comprising the target polynucleotide sequence bounded by first PBS and the second PBS or the complement of the second PBS; (c) detecting the amplicon by hybridizing a detection probe to the amplicon, which detection probe binds both of (i) the first PBS and (ii) the second PBS or the complement of the second PBS.

In one approach the target polynucleotide is double stranded, the first target-binding sequence is located at the 3' terminus of the first encoding primer, the second target-binding sequence is located at the 3' terminus of the second encoding primer, and the first and second primer binding sequences are on different strands of the target polynucleotide. In one approach the amplification conditions are PCR amplification conditions. In one approach the target polynucleotide is double stranded, the first target-binding sequence is located at the 3' terminus of the first encoding primer, the second target-binding sequence is located at the 5' terminus of the second encoding primer, and the first and second primer binding sequences are on the same strand of a the target polynucleotide. In one approach the amplification conditions are LCR amplification conditions. In one approach the first encoding primer comprises a first target binding sequence or complement thereof, a first probe binding sequence or complement thereof, and an first indexing sequence, and the second encoding primer comprises a second target binding sequence or complement thereof, a second probe binding sequence or complement thereof, and a second indexing sequence, and wherein the target sequence is further amplified using a forward primer comprising the first probe binding sequence or complement thereof, and the first indexing sequence, and a reverse primer comprises the second probe binding sequence or complement thereof, and the second indexing sequence. In one approach the second encoding primer the second probe binding sequence or complement thereof is between the second target binding sequence and the second indexing sequence.

In one aspect, the disclosure provides a method of detecting the presence of a double stranded or partially double stranded target polynucleotide in a sample, comprising: (a) contacting the target polynucleotide with a first encoding primer and a second encoding primer, wherein a first encoding primer comprises a first target-binding sequence complementary to and capable of hybridizing to a first primer binding sequence of the target polynucleotide, and a first probe binding sequence, wherein a second encoding primer comprises a second target-binding sequence complementary to and capable of hybridizing to a second primer binding sequence portion of the target polynucleotide, and a second probe binding sequence, wherein the first and second target-binding sequences are on complementary strands of the target polynucleotide; (b) amplifying a double-stranded target sequence between and including the first and second primer binding sequences to produce an amplification product comprising the first and second probe binding sequences; (c) contacting the amplification product with a detection probe, such that the detection probe binds to both the first and second probe binding sequences; and (d) detecting said binding, thereby determining that the target polynucleotide is present in the sample.

In one aspect the disclosure provides a method of detecting the presence of a target polynucleotide sequence in a sample, comprising: a) amplifying the target polynucleotide sequence to produce an amplicon comprising the target polynucleotide sequence flanked by a first probe-binding sequence and a second probe-binding sequence, b) hybridizing a detection probe to the amplicon to form a detection probe-amplicon complex, wherein the detection probe comprises, a first segment that hybridizes to the first probe-binding sequence, a second segment that hybridizes to the second probe-binding sequence, and an extendible 3'-terminus, a signal moiety positioned 5' to the extendible 3' terminus; c) maintaining the detection probe-amplicon complex in the presence of DNA polymerase having 5' nuclease activity under extension reaction conditions, wherein the extendible 3' terminus of the detection probe is extended, wherein the amplicon acts as the template for the extension reaction and wherein the 5' terminus of the detection probe is hydrolyzed by the nuclease activity and the signal moiety is released from the detection probe-amplicon complex. In one approach, the extension reaction produces an amplifiable polynucleotide, further comprising amplifying the polynucleotide using a forward primer and a reverse primer. The detection probe may the forward primer. In one approach, step (a) includes amplifying the target polynucleotide sequence using a first encoding primer with the structure 5'-P-I-T-3' and a second encoding primer with the structure 5'-I-P-T-3'.

In one aspect, the disclosure provides a method of detecting the presence of a target polynucleotide sequence in a sample, comprising: a) amplifying the target polynucleotide sequence to produce an amplicon comprising the target polynucleotide sequence flanked by a first probe-binding sequence, a second probe-binding sequence, and an indexing sequence, b) hybridizing a detection probe to the amplicon to form a detection probe-amplicon complex, wherein the detection probe comprises a first segment that hybridizes to the first probe-binding sequence, a second segment that hybridizes to the second probe-binding sequence, and a non-extendible 3'-terminus, a signal moiety positioned 5' to the extendible 3' terminus, c) maintaining the detection probe-amplicon complex in the presence of DNA polymerase having 5' nuclease activity and an indexing primer that hybridizes to a sequence in the amplicon that is complementary to the indexing sequence under extension reaction conditions, wherein the indexing primer is extended, wherein the amplicon acts as the template for the extension reaction and wherein the 5' terminus of the detection probe is hydrolyzed by the nuclease activity and the signal moiety is released from the detection probe-amplicon complex.

In one aspect the disclosure provides a method for specific detection of a microRNA, comprising: (a) combining (i) a sample comprising the microRNA, (ii) an artificial nucleic acid template comprising a first sequence that is complementary to the microRNA and a second sequence that is 3' to the first sequence, (iii) reagents for DNA-dependent extension of an RNA primer including a polymerase; thereby producing an extension combination; (b) exposing the extension combination to conditions under which the microRNA anneals to the nucleic acid template and the microRNA is extended by the polymerase thereby producing a chimeric polynucleotide comprising a 5' microRNA portion and a 3' DNA portion complementary to the second sequence; and (c) detecting the production of the chimeric polynucleotide.

BRIEF DESCRIPTION OF THE FIGURES

FIGS. 1-5 illustrate encoding and detection steps according to the invention. FIG. 1 illustrates the PCR amplification and encoding of a target sequence present in a double-stranded target polynucleotide. FIG. 2 illustrates detection of a target sequence using PCR amplification. FIG. 3 illustrates $\pi_1$ hybridizing to a 3' portion of $P_1$ and $\pi_2$ hybridizing to a 5' portion of $P_1$ and to $P_2$. FIGS. 4A and 4B illustrate two different conformations of detection probes hybridized to amplicon sequences. FIG. 4A illustrates an embodiment in which the encoding amplification is carried out using encoding primers in which each probe-binding sequence lies between an indexing sequence and the target sequence. FIG. 4B illustrates an embodiment in which the encoding amplification is carried out using a pair of encoding primers in which one primer comprises an indexing sequence between the target sequence and a probe binding sequence and the second primer comprises a probe-binding sequence between the target sequence and an indexing sequence. FIG. 4C shows a conformation in which the decoding primer hybridizes to the target-binding sequence T, which is analogous to an indexing sequence in this embodiment. FIGS. 5A-5D are illustrations of FRET-type detection probes hybridized to a single strand of an amplicon, and illustrate that detection probes may have several possible designs. FIGS. 5A and 5C illustrate that in some probes the $\pi$ sequences are adjacent to each other, while FIGS. 5B and 5D illustrate that in others the π sequences may be separated by a linker L. FIGS. 5E and 5F illustrate another arrangement wherein the FRET-type moiety is incorporated in the 5' end of the detection probe such that the spacing between the quencher and reporter is reduced to decrease the background fluorescence of the non-hydrolyzed probe molecule.

FIGS. 16-23 illustrate encoding and detection steps using the Ouroboros conformation.

FIG. 31 shows the results of an assay.

FIG. 34 shows the results of an assay. FIG. 34A shows encoding and decoding reactions that were carried out to detect target sequence. FIG. 34B shows that a concentration dependent response in fluorescence signal was detected.

FIG. 35A shows steps ("extension steps") that are carried out in one reaction volume (e.g., in a single tube, well or chamber) and FIG. 35B shows steps ("amplification steps") that are carried out in a different reaction volume or volumes. FIG. 35C shows an approach that reduces or eliminates "background" amplification of the synthetic DNA template. "FPEP"=forward primer extension product. "MiRNA" (heavy bold line) indicates a miRNA, while "MiRNA'" indicates a DNA sequence complementary to the miRNA. A "prime" mark indicates a complementary sequence. The synthetic template is shown as a dashed line.

FIG. 36A shows the double-stranded product of the amplification step. FIG. 36B shows detection of the amplification product. Ai=indexing primer; Bu=universal left (5' end) probe element, Cu=forward primer sequence for second strand, Du=universal right (5' end) probe element and Ei=reverse decoding primer (indexed).

DETAILED DESCRIPTION

1. Definitions and Terminology

Figure 1:
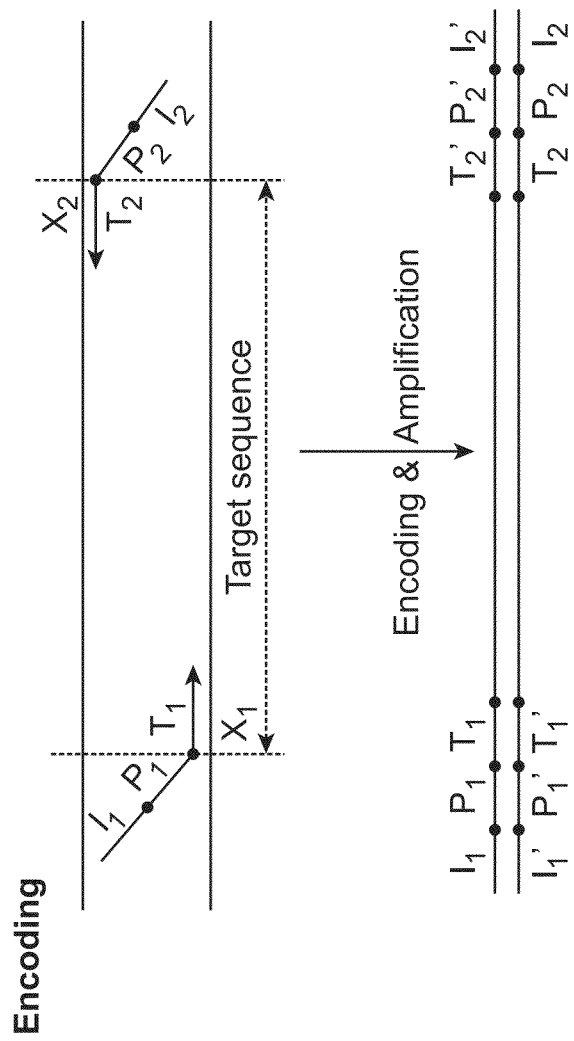

As used herein, a "sequence" means a nucleic acid base sequence. Unless otherwise indicated or apparent from context, bases or sequence elements are listed in the order 5' to 3' as they appear in a polynucleotide.

The term "segment," refers to a sequence in the polynucleotide having a particular function, e.g., probe segment, binding segment, target segment.

A "target sequence" or "target segment" is a nucleic acid sequence detected in an assay. In most cases a target sequence of interest is predefined (i.e., sequence is known prior to analysis). In other cases the complete target sequence is not known, but is defined as the sequence that is amplified by primers of known sequence. A target sequence may be found in DNA (including genomic, mitochondrial, viral, synthetic and cDNA), in RNA, or in amplifiable synthetic analogs thereof.

Two target sequences are "distinct" if they differ from each other by at least one nucleotide.

A "polynucleotide" refers to DNA, RNA, or analogs thereof. Polynucleotides may be single-stranded or double-stranded, and are at least 10 bases or basepairs in length. A polynucleotide having a length in the range of 10-70 bases, inclusive, can be called an "oligonucleotide."

A "target polynucleotide" is a polynucleotide that comprises a target sequence. In a double-stranded target polynucleotide the target sequence is on one strand and the complement of the target sequence is on the other strand.

As used herein, "complementary" has its normal meaning in the molecular biology arts, and refers to a relationship between two antiparallel nucleic acid sequences in which the sequences are related by the base-pairing rules: A pairs with T or U and C pairs with G. A first sequence or segment that is "perfectly complementary" to a second sequence or segment is complementary across its entire length and has no mismatches. A first sequence or segment is "substantially complementary" to a second sequence of segment when a polynucleotide consisting of the first sequence is sufficiently complementary to specifically hybridize to a polynucleotide consisting of the second sequence. For illustration, hybridization conditions are salt concentrations less than about 1.0 M sodium ion, typically about 0.01 to 1.0 M sodium ion at pH 7.0 to 8.3, and temperatures at least about 30° C. for oligonucleotides (e.g., 10 to 50 nucleotides) and at least about 60° C. for long probes (e.g., greater than 50 nucleotides). Typically, specific hybridization will occur when there is at least about 55% base complementarity over a stretch of at least 14-25 nucleotides, preferably at least 65%, more preferably at least 75%, and most preferably at least 90%. The prime symbol ['] is used to indicate a perfectly or substantially complementary sequence.

The terms "anneal", "hybridize" or "bind," in reference to two polynucleotide sequences, segments or strands, are used interchangeably and have the usual meaning in the art. Two complementary sequences (e.g., DNA and/or RNA) anneal or hybridize by forming hydrogen bonds with complementary bases to produce a double-stranded polynucleotide or a double-stranded region of a polynucleotide.

Two sequences or segments in a polynucleotide are "adjacent" or "contiguous" if there is no intervening sequence or non-nucleotide linker separating them. In some contexts, "non-adjacent" refers to two probe-binding sequences separated from each other by an intervening target sequence.

The terms "amplicon" and "amplification product" are used interchangeably and have their usual meaning in the art. The grammatically singular term, "amplicon," can refer to many identical copies of an amplification product. Moreover, reference to an "amplicon" encompasses both a molecule produced in an amplification step and identical molecules produced in subsequent amplification steps (such as, but not limited to, amplification products produced in subsequent rounds of a PCR amplification).

Two sequences are "associated" when the first and second sequences appear in the same single or double-stranded polynucleotide molecule or when the first sequence and the complement of the second sequence appear in the same polynucleotide strand. Two associated sequences may or may not be contiguous with each other.

A "primer" is an oligonucleotide or polynucleotide comprising a sequence that is complementary to, and capable of hybridizing to, a target sequence or an indexing sequence, or the complement thereof. In some cases a primer is extended by a DNA-dependent DNA polymerase. However, as the term is used herein, a "primer" may refer to an oligonucleotide that is not extended, such as "primers" that hybridize to a target sequence in ligase based amplification reactions.

A "decoding primer" is a primer that specifically binds to an indexing sequence or complement thereof, or target-binding sequence or complement thereof, or target sequence or complement thereof, in an amplicon produced according to the process described herein, and which may be extended by a DNA polymerase.

The terms "multiplex" and "multiplexing" refer to assays in which two or more primer sets are used to amplify two or more distinct target sequences in the same amplification reaction mixture.

A "amplification reaction mixture" is the solution in which an amplification reaction takes place and may comprise target polynucleotides, primers, polymerase, ligase, amplification reagents, amplicons, buffering agents, nuclease inhibitors, divalent cations, dNTPs, and/or other components known in the art for amplification.

As used herein, a "sample" refers to a composition containing a target polynucleotide. Exemplary samples include purified or partially purified DNA or RNA, cells and cell lysates (e.g., eukaryotic cells, human cells, animal cells, plant cells, stem cells, blood cells, lymphocytes, bacterial cells, recombinant cells and cells infected with a pathogen. tissue samples), viruses, environmental samples (e.g., water samples), food samples, forensic samples, plant samples, blood samples and the like.

As used herein, "amplification" of a nucleic acid sequence has its usual meaning, and refers to in vitro techniques for enzymatically increasing the number of copies of a target sequence. Amplification methods include both asymmetric methods (in which the predominant product is single-stranded) and conventional methods (in which the predominant product is double-stranded).

Abbreviations: P—probe-binding sequence, I—indexing sequence; T—target-binding sequence; X—primer-binding sequence; π—amplicon-binding sequence; R—reporter; Q—quencher; L—linker.

Symbols: The "prime symbol" (') indicates that a sequence (e.g., X') is complementary to a corresponding sequence (e.g., X). The colon symbol (:) indicates that a first sequence segment (e.g., X') is hybridized to a second sequence (e.g., X or π), e.g., "X':X" or "X':π".

2. Detection of Target Polynucleotides

In one aspect, the invention provides methods for detecting target nucleic acid sequences in a sample. A target sequence may be of interest because it is from a pathogenic organism, because it contains genetic information such as a single nucleotide polymorphism, deletion or insertion, because copy number variation of the sequence is informative of a subject's medical status, and for many other reasons that will be known to physicians and scientists. A target sequence may be found in a naturally occurring polynucleotide and/or may be from a non-naturally occurring polynucleotide such as an amplicon. For example, a sequence may be amplified from a naturally occurring template, optionally with addition of synthetic sequences, and the resulting amplicon sequence detected.

In some embodiments detection of target sequences in a sample sometimes can be described as a three-step process involving (1) an encoding amplification in which the target sequence is associated with probe-binding sequences and optionally with indexing sequences, (2) a distribution step in which the product of the encoding amplification is split into multiple aliquots, and (3) a decoding and detection step in which the presence, absence, quantity, or relative amounts of the target sequence in the aliquots is determined. The determination of the presence, absence, quantity, or relative amount of the target sequence is indicative of the presence, absence, quantity, or relative amount of the target sequence in the initial sample. In some embodiments the detection of target sequences in a sample comprises (1) an encoding amplification and (2) a decoding and detection step, without a distribution step.

2.1. Encoding Amplification

In the encoding amplification step, a target sequence (or more typically, multiple different target sequences in a multiplex reaction) are associated with specified nucleic acid sequences referred to as "probe-binding sequences". Optionally the target sequence is also associated with one or more "indexing sequences." This association is effected when the target sequence is amplified using an "encoding primer set." Each encoding primer in an encoding primer set may have a "target-binding" sequence or segment (T), and a "probe-binding" sequence or segment (P). Optionally, one or more encoding primers in an encoding primer set includes an "indexing sequence" (I). Although typically an encoding primer has two (T+P) or three (T+P+I) sequence elements, the presence of additional sequence elements is not excluded.

Various amplification methods may be used to associate probe-binding sequences, and optionally indexing sequences, with target sequences in an encoding amplification. For clarity the discussion below focuses initially on polymerase chain reaction (PCR) approaches in which the encoding primer set consists of two primers designed to amplify a specified target sequence under PCR amplification conditions. In PCR amplification approaches, the target-binding sequence T is located at the 3' end of the encoding primer.

FIG. 1 illustrates the PCR amplification and encoding of a target sequence present in a double-stranded target polynucleotide. The target sequence is in the upper strand with the boundaries shown, while the lower strand comprises the complement of the target sequence. As shown in FIG. 1, amplification produces an amplicon in which the target sequence is flanked, through the encoding process, by a first probe-binding sequence ($P_1$) and the complement of a second probe-binding sequence ($P_2'$), a first target-binding sequence ($T_1$) the complement of a second target-binding sequence ($T_2'$), and optionally one or more indexing sequences (I). In referring to the target-binding, probe-binding sequences or indexing sequences, we will generally refer to a "pair of probe-binding sequences," for example, rather then to the more cumbersome "first probe-binding sequence and complement of second probe-binding sequence." It will be apparent to the reader, particularly with reference to the figures, when reference to a complementary sequence is encompassed.

The portion of the target polynucleotide to which the target-binding sequence (T) hybridizes is referred to as a primer-binding sequence (X). The target-binding sequence T of the encoding primer is sufficiently complementary to X to specifically hybridize to the target polynucleotide. If both target-binding sequences (T) are exactly complementary to the primer binding sequences (X) to which they bind, the sequence [$T_1$-target sequence-$T_2'$] in the amplicon will correspond exactly to a sequence in the polynucleotide template. When a target-binding sequence T is not exactly complementary to the primer binding sequence P, it will be at least sufficiently complementary to specifically hybridize. In addition, T's sequence may be further constrained by the requirements of the amplification method. For example, if the encoding primer is a PCR primer, the 3' base should bind the corresponding base of the target sequence to promote primer extension.

An exemplary amplicon, or amplification product, produced in the encoding amplification is illustrated in FIG. 1. In this example, each probe-binding sequence lies between an indexing sequence and the target sequence. Somewhat different amplicons are illustrated in FIG. 16 (indexing sequence lies between the probe-binding sequence and the target sequence), FIG. 26 (target-binding sequence is also the indexing sequence), FIG. 29 (in one encoding primer, the indexing sequence lies between the probe-binding sequence and the target sequence and in the second encoding primer the probe-binding sequence lies between the indexing sequence and the target sequence) and FIG. 28 (LCR amplicon, in which target-binding sequences are, or take the place of, target sequence). In each case, a pair of probe-binding sequences flank a target sequence (FIGS. 16, 26 and FIG. 28, if T's are exactly complementary to X's) or a sequence substantially identical to a target sequence (FIG. 28, if a T is not exactly complementary to an X). As is illustrated in the figures, "indexing sequences" (I) may also be associated with the target sequence in the amplicon. Functions of indexing sequences are explained below.

Although for simplicity FIG. 1 shows amplification of a single target sequence, the encoding amplification is typically a multiplex reaction. That is, two or more different target sequences are amplified using different encoding primer sets. Usually at least two of the different target sequences become associated through the encoding amplification with a different combination of probe-binding sequences and/or different indexing sequences, such that the amplicons containing different target sequences can be distinguished from each other in the decoding step. It will be appreciated that a combination of probe-binding sequences is order dependent. That is the combination 5'-$P_1$-$P_2$-3' is not the same as the combination 5'-$P_2$-$P_1$-3').

Figure 28:
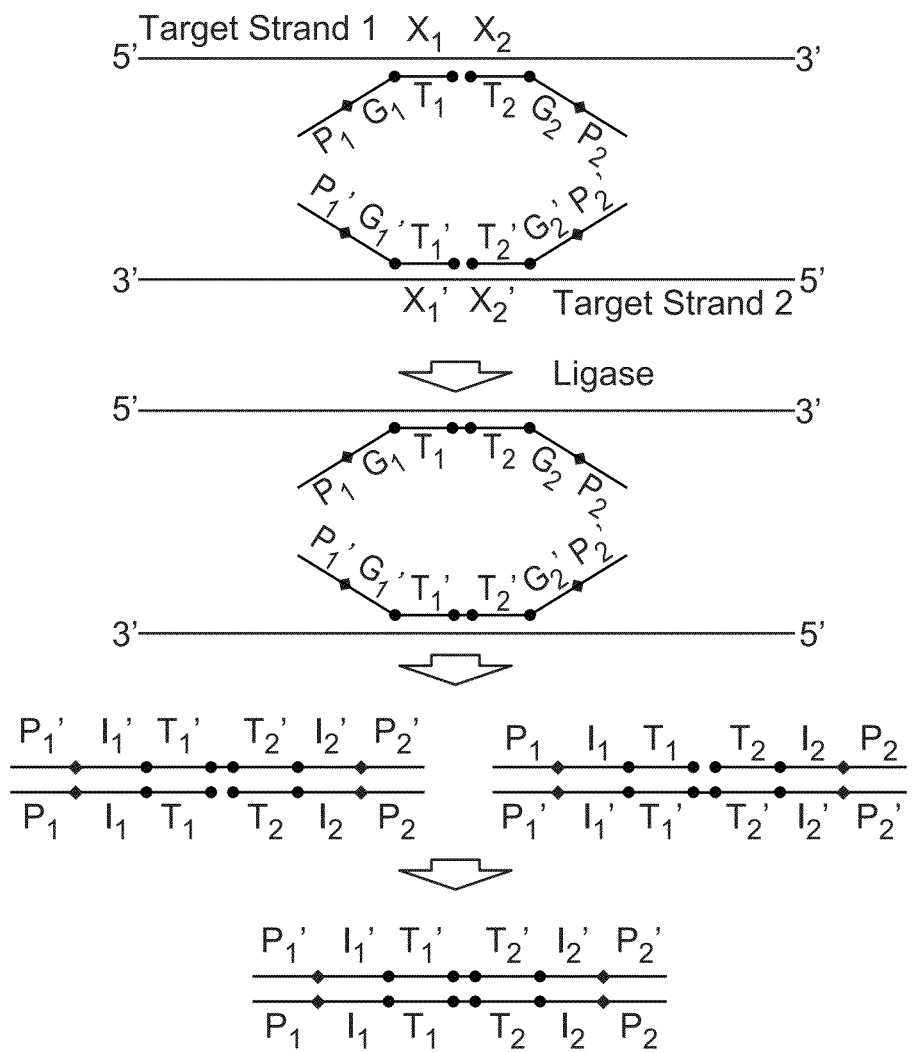
FIG. 28 illustrates an encoding amplification using the ligase chain reaction.

As noted above, amplification methods other than PCR methods may be used in the encoding amplification. For example, amplification may be carried out using the ligase chain reaction (LCR), in which case an encoding primer set may consist of four primers. FIG. 28 illustrates an encoding amplification using the ligase chain reaction (LCR). As outlined in FIG. 28, multiple rounds of denaturation, annealing and ligation using a thermostable DNA ligase result in the exponential amplification of the target sequence (or target-binding sequence), producing an amplicon that may be subject to decoding and detection as described elsewhere herein.

In this approach, the "encoding primer set" contains two pairs of primers, rather than one pair used in PCR methods. An encoding primer set used for such amplification includes a first primer, with a 3' terminal segment sufficiently complementary to the target sequence to anneal to the target polynucleotide, and a second primer, with a 5' terminal segment sufficiently complementary to anneal to the target polynucleotide (e.g., 5'-P/I-T-3' and 5'-T-P/I-3' where "P/I" means "P" or "P and I, in either order"). The second pair comprises sequences complementary to the sequences of the first pair.

In conventional LCR methods, and as illustrated in FIG. 28, the primers are designed to anneal at adjacent sites on the target strand so that the 3' base of one primer can be ligated directly to the 5' base of the second primer. Alternate methods are known however, including "Gap-LCR" (in which DNA polymerase is used to fill a gap between two annealed probes), PCR-followed by LCR, inclusion of a flap endonuclease (FEN) as part of the LCR method, and the like, which may be adapted for the present invention. See, e.g., Abravaya et al., 1995, *Nuc. Acids Res.* 23:675-682 and references cited therein, all incorporated by reference herein. Also see, e.g., Wiedmann et al., 1994, *Genome Res.* 3:S51-S64 and Gill and Ghaemi, 2008, "Nucleic acid isothermal amplification technologies: a review" *Nucleosides, Nucleotides & Nucleic Acids*, 27:224-43, and Bi et al, U.S. Pat. No. 6,511,810, all incorporated by reference herein.

It will be appreciated that PCR, LCR and other amplification methods and conditions are well known and need not be described in detail here. In general terms, the amplification reaction mixture (the solution in which the amplification reaction takes place) may comprise sample (containing target polynucleotides), primers, amplification reagents, amplicons, buffering agents, nuclease inhibitors, $Mg^{++}$ or other divalent cations, dNTPs, and other components known in the art for amplification. Enzymes that may be present include DNA polymerase (e.g., Taq polymerase), ligase (e.g., bacteriophage T4 ligase, *E. coli* ligase, Afu ligase, Taq ligase). In some embodiments the DNA polymerase has a 5' nuclease activity. It is routine in the art to design primers and select amplification conditions (e.g., slope, duration and temperatures for denaturation, annealing and extension in PCR).

The encoding amplification is generally a multiplex amplification. That is, primer sets are included that are sufficient to amplify at least two different target sequences, thereby producing at least two distinguishable amplicons if the at least two target sequences are present in the sample. Distinguishable amplicons may differ at a single nucleotide (e.g., representing polymorphic variation), or at more than one nucleotide. Distinguishable amplicons may differ in sequence due to an insertion or deletion in one relative to another.

In one embodiment, all of the amplicons produced in a multiplex amplification reaction share the same combination of probe-binding sequences (e.g., all $P_1$+$P_2$), reflecting the use of encoding primers designed with the same probe binding sequences. As is discussed below, this allows all of the amplicons to be detected using a single detection probe, even if they contain different amplified target sequences. In other embodiments, some but not all of the amplicons share the same combination of probe-binding sequences (e.g., some amplicons comprise $P_1$+$P_2$ and other amplicons comprise $P_3$+$P_4$, or some amplicons comprise $P_1$+$P_2$ and other amplicons comprise $P_1$+$P_3$). In still other embodiments, each of the amplicons produced in a multiplex amplification reaction has a different (unique) combination of probe binding sequences.

Distinct encoding primer sets may have members in common. For example, a first set may comprise forward primer A and reverse primer C, and a second set may comprise forward primer B and reverse primer C.

An encoding amplification step that precedes a distribution step is sometime called a "pre-amplification" step.

2.2. Distribution Step

In the second step, the encoding amplification reaction mixture is divided into two or more separate aliquots, each of which can be independently assayed for the presence or absence of a target sequence. The presence or absence of a target sequence in an aliquot is indicative of the presence, absence, quantity, or relative amount of the target sequence in an initial sample selected for analysis. Separate aliquots are usually assayed at the same time.

In some embodiments, decoding primers and/or detection probes (both discussed below) are added to individual aliquots. That is, in some embodiments the reaction mixture is distributed into individual aliquots and specific reagents (e.g., detection probes and/or decoding primers) are added to each aliquot. In a different embodiment, distribution of a sample into aliquots comprises combining the reaction mixture with reagents (e.g., detection probes), and then distributing the mixture into individual aliquots of the mixture without subsequent addition of specified additional reagents, e.g., detection probes and/or decoding primers.

Specific methods for distribution are not critical to the practice of the invention, although they may be of practical significance. In one embodiment, distribution is carried out by manual pipeting. For example, ten 1-microliter aliquots of a 10-microliter reaction mixture may be distributed to individual tubes or well by pipeting. More typically, robotic methods are used and preferably microfluidic methods are used for efficiency and economy.

For illustration and not limitation, a number of microfluidic devices are known for distribution of a sample or reaction mixture followed by addition of reagents. Fluidigm Corp. (South San Francisco Calif.) provides a number of platforms for distribution and combinatorial addition of reagents, including commercially available Dynamic Array™ and Access Array™ systems, and as well as systems described in the literature (see, e.g., U.S. Pat. No. 7,604,965; Patent publications WO 2010/077618; US 2009/0317798; US 2008/0223721; US 2009/0257920; US 2009/0291435; and unpublished application Nos. U.S. Ser. No. 12/804,568 and PCT/US10/58459). Other approaches include use of microfluidic cards. One useful approach involves distribution of the reaction mixture into microdroplets in which amplification reactions may be carried out (see, e.g., Patent Application Publication Nos. US 2009/0035838; US 2010/0022414; WO 01/89788; WO 2006/040551; WO 2006/040554; WO 2004/002627; WO 2008/063227; WO 2004/091763; WO 2005/021151; WO 2006/096571; WO 2007/089541; WO 2007/081385 and WO 2008/063227. In one droplet-based approach the sample may be partitioned into a plurality of droplets and individual same droplets fused with droplets containing specified reagents.

In another approach, partitioning methods are used. In these methods the encoded sample is combined with detection reagents (and optionally indexing reagents) prior to distribution to separate compartments or droplets in which the detection reactions are carried out (see, e.g., U.S. Pat. No. 7,604,965). For example, the mixture can be distributed to individual aliquots by partition of a channel containing the mixture, by distribution of the mixture into droplets, and the like. In some embodiments a commercially available Digital Array™ partitioning device (Fluidigm Corp., South San Francisco, Calif.) is used.

2.3. Decoding and Detection Step

In the third step, amplicons produced in the encoding step are detected. As discussed above, each amplicon comprises two probe-binding sequences (P). Detection of an amplicon involves combining the amplicon with a detection probe under conditions in which the detection probe hybridizes to probe-binding sequences, and detecting the hybridization. Without intending to limit the invention, in some embodiments, detecting hybridization entails (1) hydrolyzing a portion of the detection probe, thereby releasing a signal moiety from the detection probe, and (2) detecting the release. Without intending to limit the invention, in some embodiments, detecting hybridization entails (1) hydrolyzing a portion of the detection probe in the presence of a decoding primer, thereby releasing a signal moiety from the detection probe, and (2) detecting the release. Without intending to limit the invention, in other embodiments, displacing the bound detection probe by extending a decoding primer, and (2) detecting the displacement.

Figure 2:
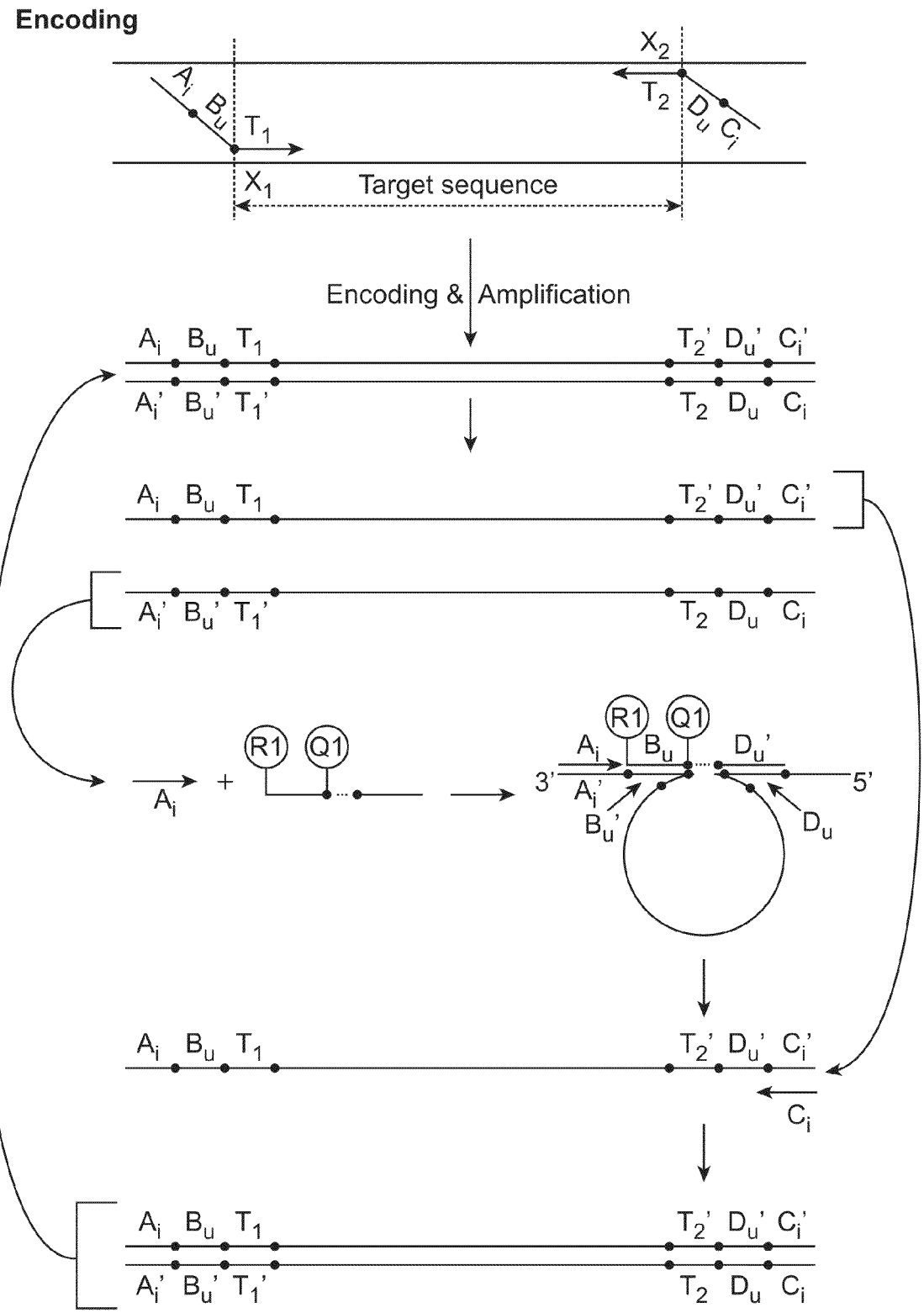

We will first provide an overview of the Decoding and Detection Step by referring to FIG. 2, which illustrates an exemplary embodiment. We will then describe detection probes and the decoding process in additional detail.

A variety of approaches to decoding are described herein. In describing these methods general familiarity with quantitative PCR methods has been assumed. For background, see, e.g., Bustin S A (ed), 2004, A-Z OF QUANTITATIVE PCR. La Jolla, Calif.: IUL Biotechnology Series, International University Line, incorporated by reference herein, and other references cited herein. As used herein "amplification conditions" refer to target and reagent concentrations, temperature (including thermocycling profiles), buffer compositions, and the like necessary to amplify a sequence using PCR, LCR or other amplification approaches. Amplification conditions are well known in the art, and are described in the scientific and patent literature, including but not limited to references cited herein.

2.3.1 Overview

FIG. 2 illustrates detection of a target sequence using PCR amplification. In Figure The six structures in FIG. 2 may be referred to (top-to-bottom) as FIG. 2-1 to FIG. 2-6, respectively. In FIG. 2-1 the target sequence is amplified using a pair of PCR primers, each comprising a target-binding sequence ($T_1$, $T_2$), a probe-binding sequence (B, D) and an indexing sequence (A, C). Several rounds of amplification result in many (e.g., $10^3$-$10^6$) copies of an amplicon containing the target sequence flanked by probe-binding sequences B and D, and indexing sequences A and C, illustrated in FIG. 2-2. The amplicons are denatured (FIG. 2-3) in the presence of a detection probe, decoding primer $A_i$ and decoding primer $C_i$, and subjected to additional rounds of amplification. Each additional round of amplification involves regeneration of the lower strand by extension of decoding primer $C_i$ on the upper stand template (FIG. 2-5). This regeneration produces the amplicon shown in FIG. 2-6 and identically in FIG. 2-2, which is a substrate for additional rounds of amplification and detection. Each round also involves combination of the lower amplification strand with a decoding primer $A_i$ and the detection probe. The lower strand, detection probe and decoding primer adopt the conformation represented in cartoon form in FIG. 2-4. In this conformation, the detection probe binds the amplicon via annealing of the detection probe's π ("amplicon binding") sequences denoted "$B_U$" and "$D_U$" to the amplicon's probe-binding sequences of (here denoted "$B_U$" and "$D_U$"), the decoding primer $A_i$ binds an indexing sequence in the amplicon (here denoted "$A_I$"), and the decoding primer is extended. Extension of the decoding primer results in detectable release of a signal moiety (here denoted R1) from the hydrolysis probe. Extension also regenerates the double-stranded amplicon shown in FIG. 2-3 and FIG. 2-6.

In the illustration shown in FIG. 2, the detectable probe is a FRET probe and the signal moiety, R1, is a reporter dye. In this FRET approach, partial hydrolysis of detectable probe results in physical separation of the reporter dye from a quencher dye (Q1), resulting in a detectable change in the fluorescent signal. However, the invention is not limited to FRET detection, and a variety of signal moieties and probe detection methods, some of which are discussed in more detail below, may be used.

2.3.2 Detection Probes

Amplicons produced in the encoding step comprise two non-contiguous probe-binding sequences P, separated from each other in the amplicon by a target sequence. The amplicons may be detected and identified using "detection probes" of the invention. Detection probes are probes that hybridize to both of the probe-binding sequences (P) of an amplicon.

Typically, the detection probe has a pair of sequences, denoted "π" (Pi) sequences that are exactly or substantially complementary to the amplicon's probe-binding sequences. Typically, each π sequence hybridizes to a corresponding probe-binding sequence in the amplicon (e.g., $\pi_1:P_1$ and $\pi_2:P_2$).

Figure 3:
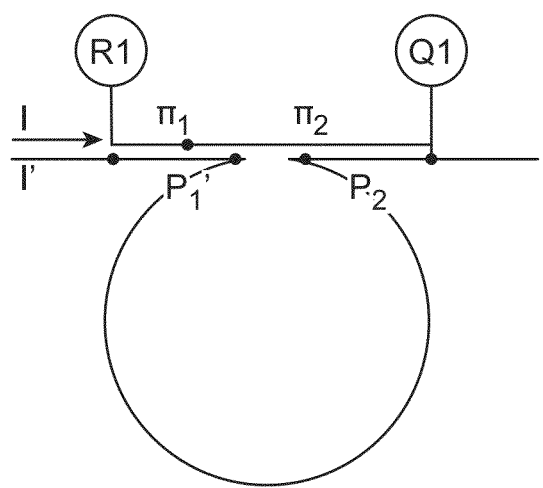
Figure 5:
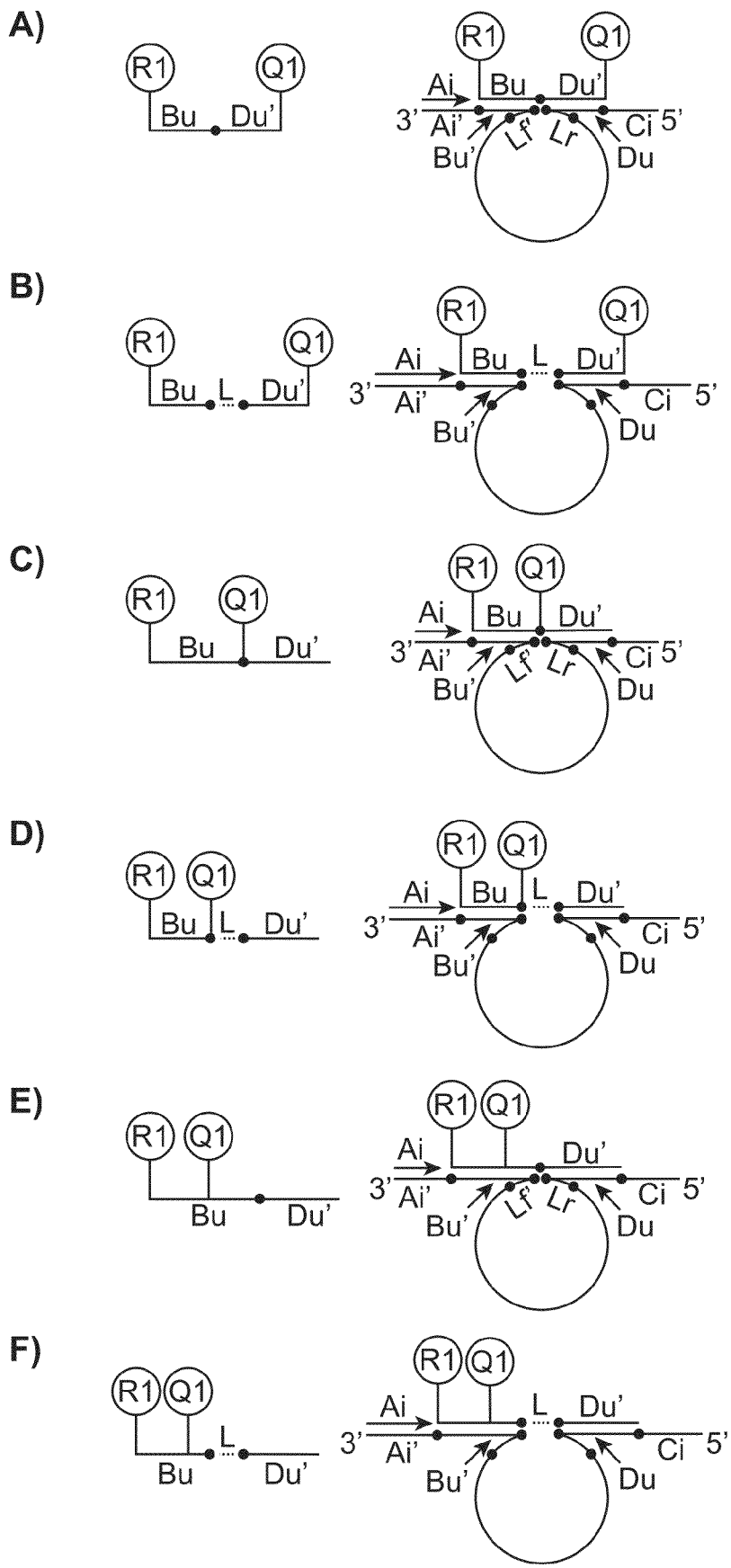

Although typically each π sequence hybridizes to a corresponding probe-binding sequence in the amplicon, in some embodiments, the detection probe is designed so that, for example, each π sequence binds to a subsequence of a probe-binding sequence P, or, for example so that one π sequence binds to a subsequence of a probe-binding sequence and the second π sequence binds to portions of two different P sequences. See, e.g., FIG. 3, showing $\pi_1$ hybridizing to a 3' portion of $P_1$ and $\pi_2$ hybridizing to a 5' portion of $P_1$ and to $P_2$. In some embodiments, the length and composition of the π sequences and the two non-contiguous probe-binding sequences is such that the detection probe will specifically anneal only to an amplicon in which both probe-binding sequences are present. Because hybridization of the detection probe to the amplicon requires the presence in the amplicon of sequences from both encoding primers, the assay provides an extremely high level of specificity.

In some embodiments (discussed below) the detection probe (while annealed to an amplicon, forming a detection probe-amplicon complex) is extended at the 3'-terminus by DNA polymerase. In embodiments in which extension is not intended it may be advantageous to add a blocker at the 3' terminus of the detection probe so that it cannot be extended. Suitable transcription blockers are well known in the art and include carbon spacers, phosphate moieties, and the like. Extension may also be blocked by the presence of non-hybridizing nucleotides (i.e., 3' nucleotides that do not anneal to the template being extended).

Binding of the detection probe to the amplicon can be detected in a number of ways, some of which are discussed below. Often, detection uses a fluorescence-based system. Typically, a system is used in which the intensity of a fluorescent signal is dependent on the proximity of a reporter and quencher to each other. Fluorescence-based systems are well known. See, e.g., Livak et al., 1995 "Oligonucleotides with fluorescent dyes at opposite ends provide a quenched probe system useful for detecting PCR product and nucleic acid hybridization" *PCR Methods Appl.* 4:357-362; Tyagi and Kramer, 1996, "Molecular beacons: probes that fluoresce upon hybridization" *Nat. Biotechnol.* 14:303-308; Piatek et al., 1998, *Nat. Biotechnol.* 16:359-63; Tyagi et al., 1998, *Nat. Biotechnol.* 16:49-53; U.S. Pat. No. 5,723,591; and U.S. Pat. No. 6,150,097 incorporated herein by reference). Exemplary reporters and quenchers include those described in Anderson et al, U.S. Pat. No. 7,601,821, incorporated herein by reference. Labeling probes can also comprise sulfonate derivatives of fluorescenin dyes with SO3 instead of the carboxylate group, phosphoramidite forms of fluorescein, phosphoramidite forms of CY 5 (available for example from Amersham). Exemplary reporter include fluorophores, such as a xanthene dye (e.g., fluorescein or a rhodamine), a cyanine dye, a dansyl derivative, EDANS, coumarin, Lucifer yellow, BODIPY, Cy3, Cy5, Cy7, Texas red, erythrosine, naphthylamine, or Oregon green, including 5-carboxyfluorescein (5-FAM); 6-carboxyfluorescein (6-FAM); 2',4',1,4,-tetrachlorofluorescein (TET); 2',4',5',7',1,4-hexachlorofluorescein (HEX); eosin; calcium green; NED; tetramethyl-6-carboxyrhodamine (TAMRA); tetrapropano-6-carboxyrhodamine (ROX); 2',7' dimethoxy-4',5-dichloro-6-carboxyrhodamine (JOE); and tetramethylrhodamine. Exemplary quenchers include tetramethylrhodamine (TAMRA), DABCYL (DABSYL, DABMI or methyl red) anthroquinone, nitrothiazole, nitroimidazole or malachite green. Quenchers are also available from various commercial sources, such as Black Hole Quenchers® from Biosearch Technologies and Iowa Black® or ZEN quenchers from Integrated DNA Technologies, Inc.

For convenience, exemplary fluorescence-based detection systems are sometimes described as using "hydrolysis probe systems" or "hybridization probe systems." When "hydrolysis probe systems" are used, a reporter and quencher associated with the detection probe are separated by a cleavage of the probe so that the reporter and quencher are associated with different molecules which can become physically separated, resulting in a change in signal. When "hybridization probe systems" are used, the reporter and quencher remain associated with the same detection probe molecule, but the conformation of the probe changes increasing or decreasing the proximity of the reporter and quencher from each other, resulting in a change in signal. Various probe systems are described in more detail below, for illustration and not limitation.

Figure 13:
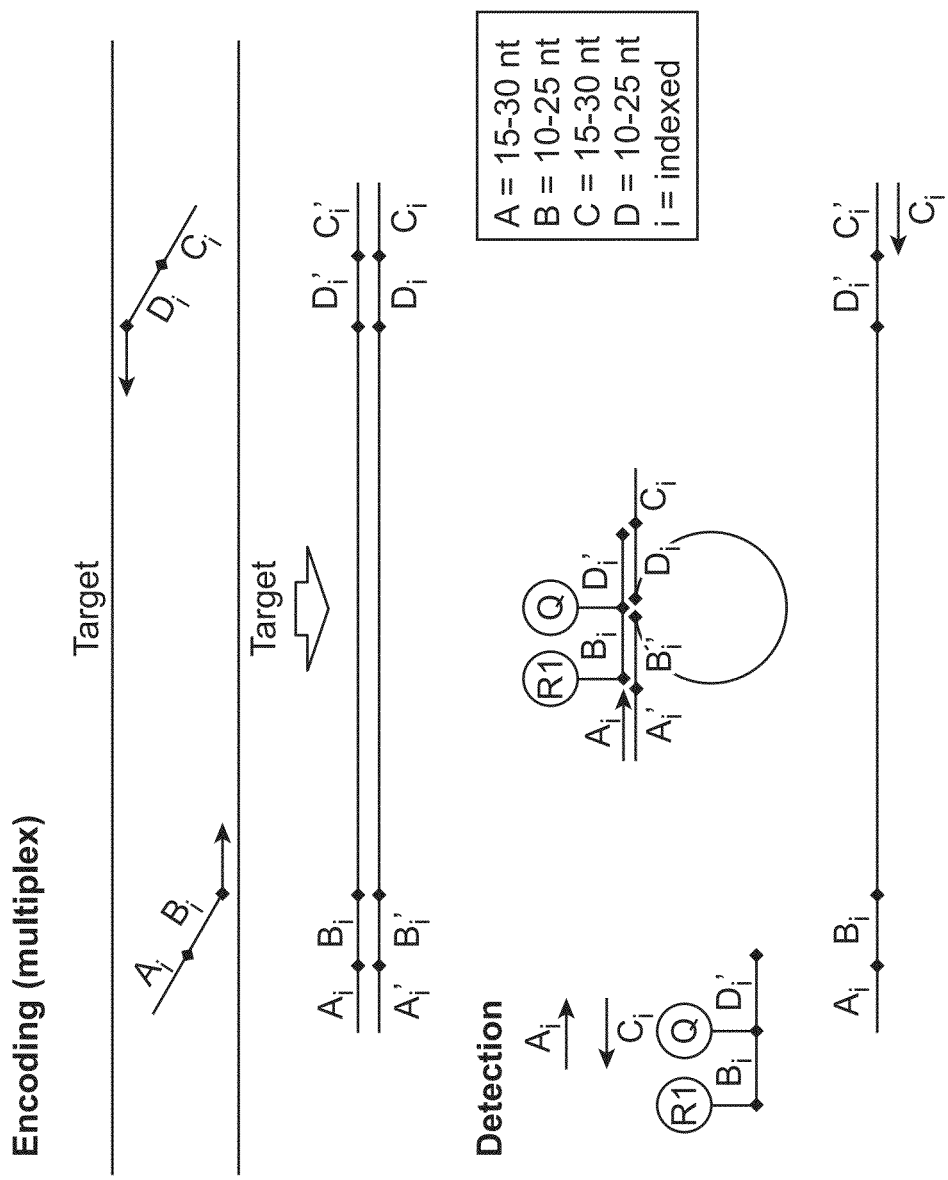
Figure 17:
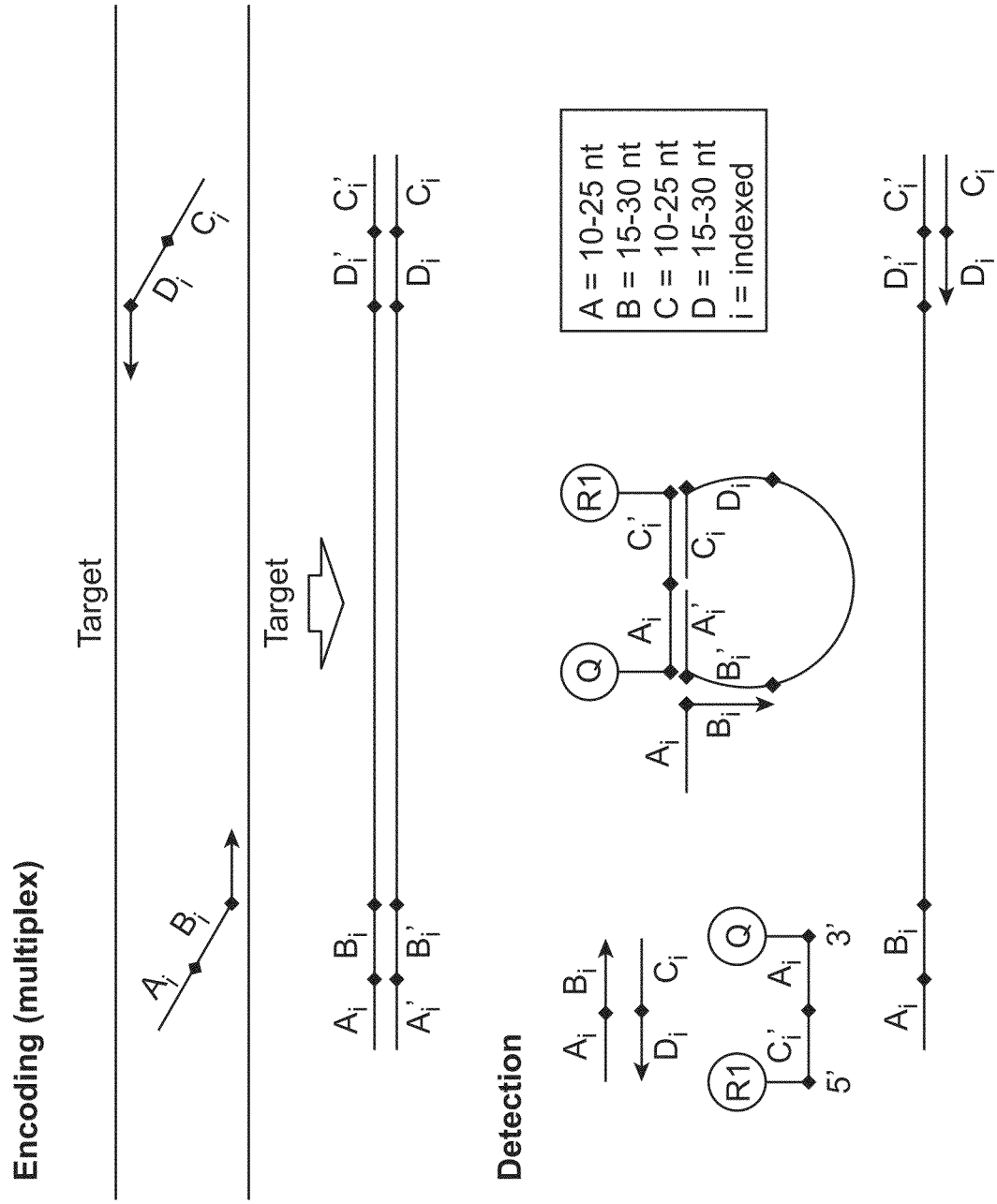

For example, in some embodiments a detection probe is a dual labeled FRET (fluorescence resonance energy transfer) type probe. A FRET-based probe comprises a donor (reporter) and acceptor (quencher) fluorophore. The donor and acceptor fluorophore pair are selected such that the emission spectrum of the donor overlaps the excitation spectrum of the acceptor. Thus, when the pair of fluorophores are within sufficiently close proximity to one another, energy transfer from the donor to the acceptor can occur and can be detected. As illustrated in FIGS. 2, 13 and 17, among others, extension of an appropriately positioned decoding primer annealed to the amplicon using a polymerase with a 5' nuclease activity (e.g., Taq polymerase) results in hydrolysis of all or a portion of the detection probe and release of the reporter (or quencher). Upon release, the quencher and reporter are physically separated, resulting in a detectable change in the fluorescent signal.

In some embodiments, the detection probe is a molecular beacon-type hybridization probe. In a molecular beacon, reporter and quencher molecules are linked at (or near) the 5' and 3' ends of an oligonucleotide that contains short (∼5 bp) complementary sequences of bases at the 5' and 3' ends. The complementary bases hybridize to form a stem-loop structure which holds the reporter and quencher close together in space at the base of the stem. When the probe hybridizes to another polynucleotide (e.g., an amplicon) it assumes a linear conformation in which the reporter and quencher are separated in space and the extent of quenching is diminished. Thus, hybridization of a molecular beacon-type probe segment to a probe-binding segment results in an increase of fluorescent signal. Extension of the decoding primer can result in displacement of the molecular beacon from the amplicon strand, allowing it to change from a linear conformation to a hairpin conformation with a resulting decrease in fluorescent signal. Alternatively, cooperative probes can be used to generate a fluorescent signal. See, e.g., Satterfield et al., 2010, *J. Mol. Diagnostics.* 12:359-67; Satterfield et al., 2008, *Nuc. Acids Res.* 36:3129; Satterfield et al., 2007, *Nuc. Acids Res.* 35:e76; Satterfield et al., 2007, *Clin Chem.* 53:2042-50, each of which is incorporated herein in its entirety.

Detection probes for use in the invention are not limited to fluorescence-based systems. For example, any probe for which hydrolysis of the probe results in a detectable separation of a signal moiety from the detection probe-amplicon complex may be used. For example, in one approach, release of the signal moiety may be detected electronically (e.g., as an electrode surface charge perturbation when a signal moiety is released from the detection probe, amplicon complex) or chemically (e.g., a change in pH in a solution as a signal moiety is released into solution). Likewise, any probe that binds the probe-binding segments and for which a change in signal can be detected upon hybridization or upon displacement of the probe from the bound amplicon may be used.

Figure 26:
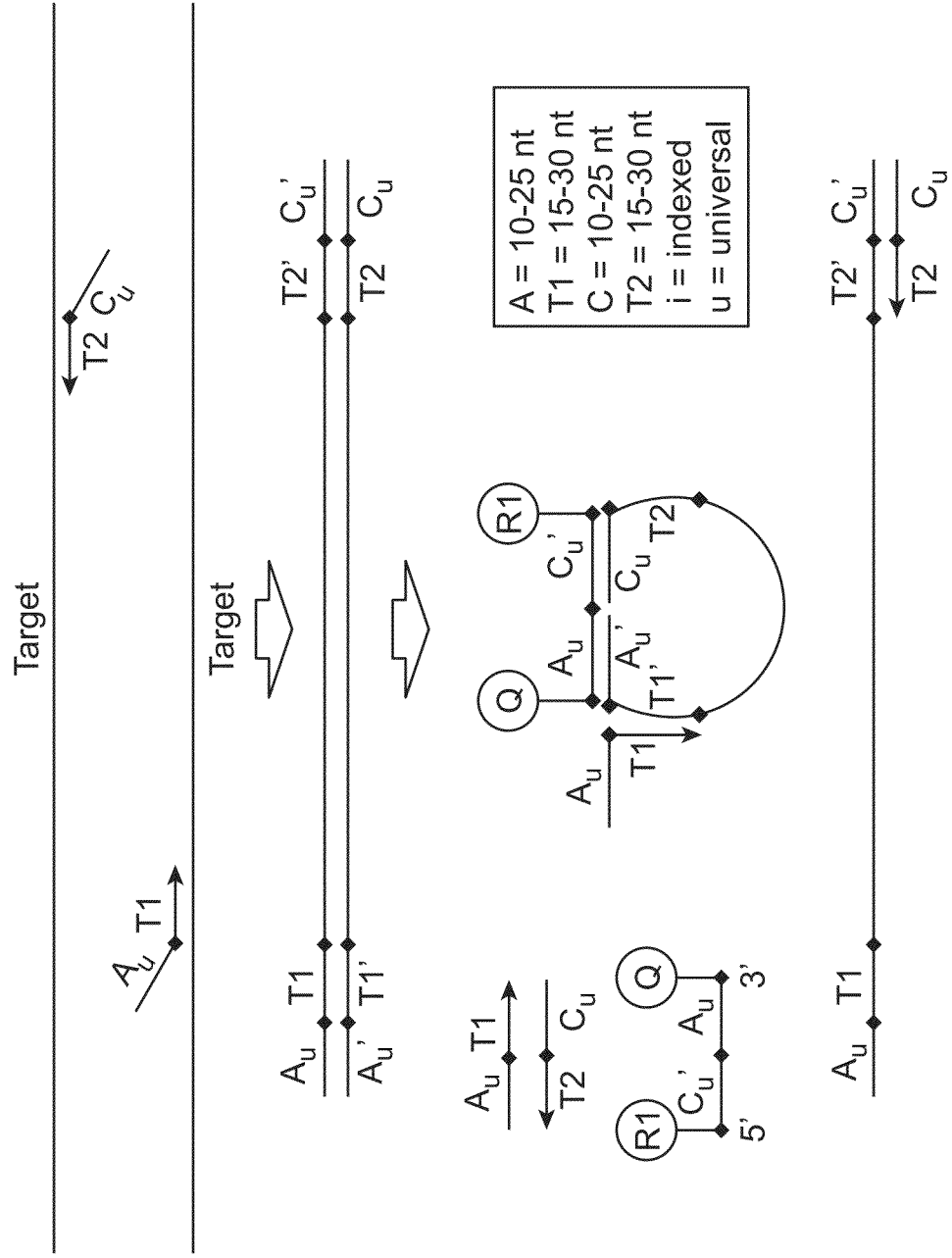
FIGS. 26-27 illustrate the use of the Ouroboros conformation using a decoding primer that hybridizes to a target-binding sequence (T) or its complement.

FIGS. 4A and 4B illustrate two different conformations of detection probes hybridized to amplicon sequences. FIG. 4A illustrates an embodiment in which the encoding amplification is carried out using encoding primers in which each probe-binding sequence lies between an indexing sequence and the target sequence, while FIG. 4B illustrates an embodiment in which the encoding amplification is carried out using a pair of encoding primers in which one primer comprises an indexing sequence between the target sequence and a probe binding sequence and the second primer comprises a probe-binding sequence between the target sequence and an indexing sequence. Also see FIG. 29. FIG. 4C shows a conformation in which the decoding primer hybridizes to the target-binding sequence T, which is analogous to an indexing sequence in this embodiment. The decoding primer could also hybridize to the target sequence of the amplicon at a position on the target sequence 3' to the position shown in the figure. In preferred embodiments, the decoding primer will also include additional sequences, e.g., probe-binding sequences, as illustrated in FIG. 26. In FIGS. 4A-C, the $\pi_1$ sequence is complementary to $P_1'$ and the $\pi_2$ sequence is complementary to $P_2$.

As is illustrated in the figures, extension of the decoding primer using a polymerase with a 5'-nuclease activity (e.g., Taq DNA polymerase) results in hydrolysis of the detection probe beginning at the 5' end of the probe. This hydrolysis can be detected in a variety of ways. In certain examples, hydrolysis results in release of the signaling moiety, and the release is detected by a change in fluorescence, luminescence, phosphorescence, pH, charge or the like.

FIGS. 5A-5D are illustrations of FRET-type detection probes hybridized to a single strand of an amplicon, and illustrate that detection probes may have several possible designs. For example, in some probes the π sequences are adjacent to each other (FIGS. 5A and 5C) while in others the π sequences may be separated by a linker L (FIGS. 5B and 5D). Linkers may be non-nucleotide linkers and/or may contain non-hybridizing nucleotides (i.e., nucleotides that do not hybridize to the amplicon). In another arrangement (FIGS. 5E and 5F) the FRET-type moiety is incorporated in the 5' end of the detection probe such that the spacing between the quencher and reporter is reduced to decrease the background fluorescence of the non hydrolyzed probe molecule. Similar to the aforementioned probe constructs (FIG. 5A-5D) the sequences in the probe molecule can be adjacent to one another or separated by a linker. Non-nucleotide linkers are known in the art. Examples include polyethylene glycol and other commercially available linkers (also called "spacers") (e.g., C3 and C12 spacers from Glen Research Corp. VA) and many others well known in the art. See, e.g., WO 2007/114986, e.g., paragraphs [00181]-[00187] incorporated herein by reference, for descriptions of linkers. Also illustrated are embodiments in which the reporter and quencher moieties are located in different portions of the detection probe. Numerous other variations will be apparent to those of skill in the art. For example, the positions of the reporter and quencher may be reversed, either or both may be linked to nucleotides at the termini of the probe or to non-terminal nucleotides.

2.3.3 Design of Primers and Detection Probes

Guided by this specification, those of skill in the molecular biology arts will be able to design detection probes, encoding primer sets, and decoding primers suitable for the practice of the invention. Parameters to be considered in probe and primer design include sequence length, secondary structure, dimer formation, GC content, reaction temperature conditions (e.g., denaturation, annealing and extension temperatures in the case of PCR), reaction salt and pH conditions, amplicon length and position, the melting temperature of the amplification product and the like. A variety of well-known methods and computer tools may be used to assist in design. See Burpo, 2001, "A critical review of PCR primer design algorithms and cross-hybridization case study" *Biochemistry* 281:1-11; Rychlik et al., 1990, "Optimization of the annealing temperature for DNA amplification in vitro" *Nuc. Acid. Res.* 18:6409-11; SantaLucia, 1998, "A unified view of polymer, dumbbell, and oligonucleotide DNA nearest-neighbor thermodynamics" *PNAS* 95:41460-65; Lowe et al., 1990, "A computer program for selection of oligonucleotide primers for polymerase chain reactions" *Nucleic Acids Res.* 18:1757-61. Sambrook et al., MOLECULAR CLONING: A LABORATORY MANUAL (C.S.H.P. Press, NY 2d ed., 1989); and Ausubel et al., CURRENT PROTOCOLS IN MOLECULAR BIOLOGY, Greene Publishing and Wiley-Interscience, New York (1997), each of which is incorporated herein by reference for all purposes.

Figure 8:
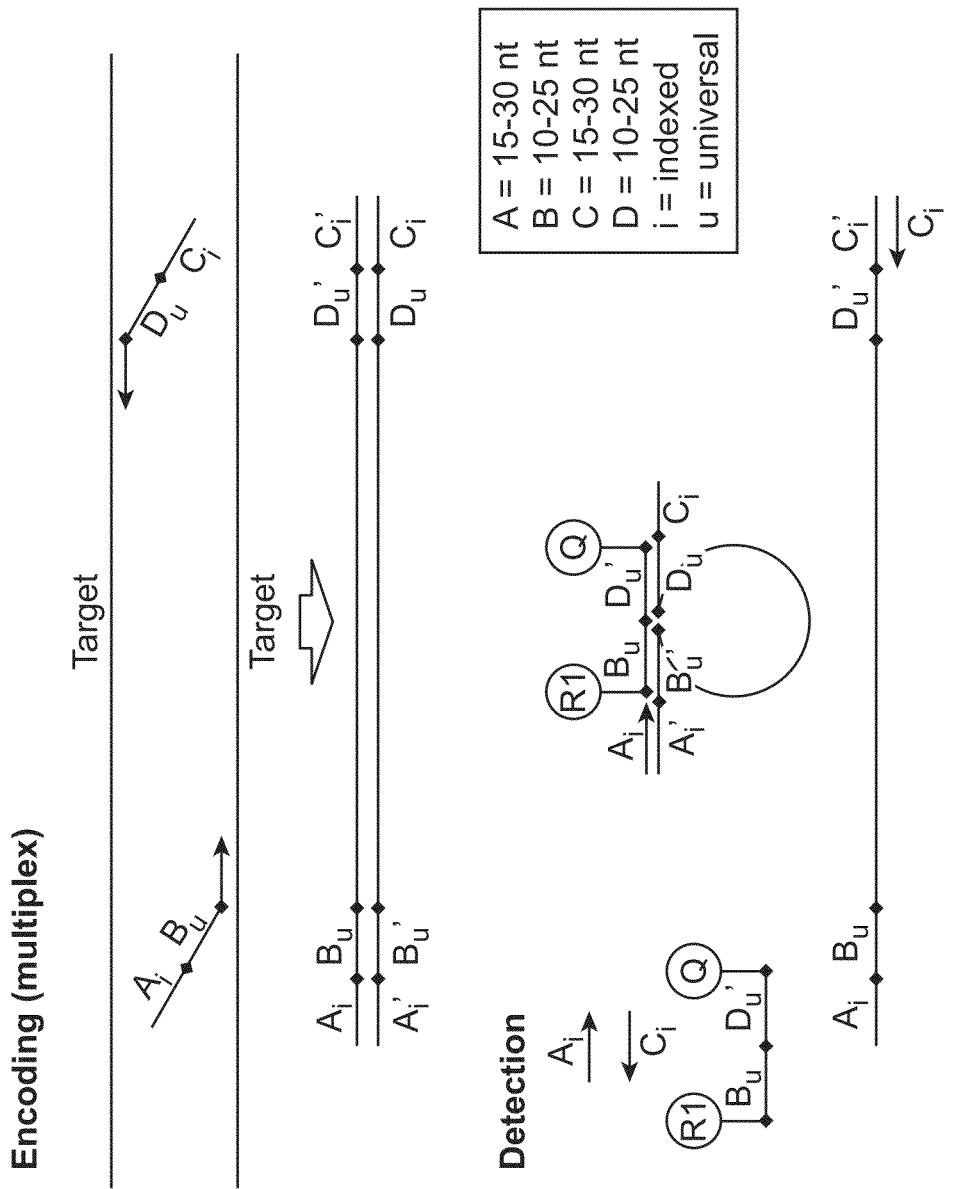
FIGS. 8-15 illustrate encoding and detection steps according to the invention.
Figure 10:
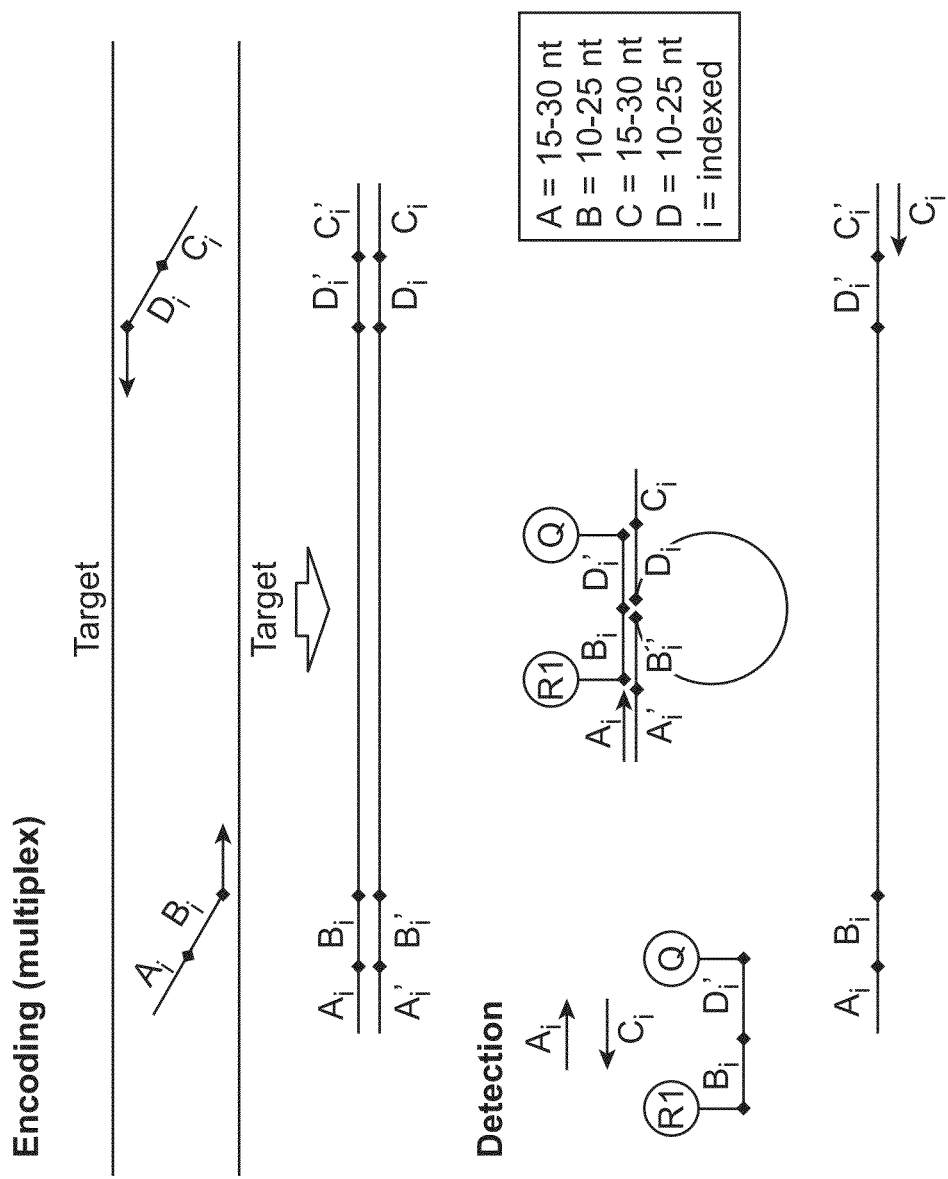

FIGS. 8, 10 and 17, among others include exemplary lengths for probe-binding sequences (e.g., 10-25 nucleotides) and indexing sequences (e.g., 15-30 nucleotides). The target-binding sequence is usually 15-30 nucleotides (e.g., 18-25 nucleotides) in length. These ranges are guidelines but are not intended to limit the invention.

2.3.4 Decoding

"Decoding" refers to the steps taken to detect a signal indicative of the presence of a particular target sequence. Thus, decoding encompasses both (1) generation of a signal from an individual probe molecule and (2) further amplification of the encoded amplicons, resulting in additional signal generation. It will be noted that the probes and primers of the invention are used in concert to achieve both of these ends.

Probe-binding (P) and π sequences can be designated as universal (subscript "u", e.g., $P_U$ or $\pi_U$; see, e.g., FIGS. 2, 5, 8) or indexed (subscript "i", e.g., $P_i$ or $\pi_i$; see, e.g., FIG. 17). Likewise, indexing sequences can be designated as universal or, more often, are indexed (e.g., $I_i$ see, e.g., FIG. 17).

Figure 6:
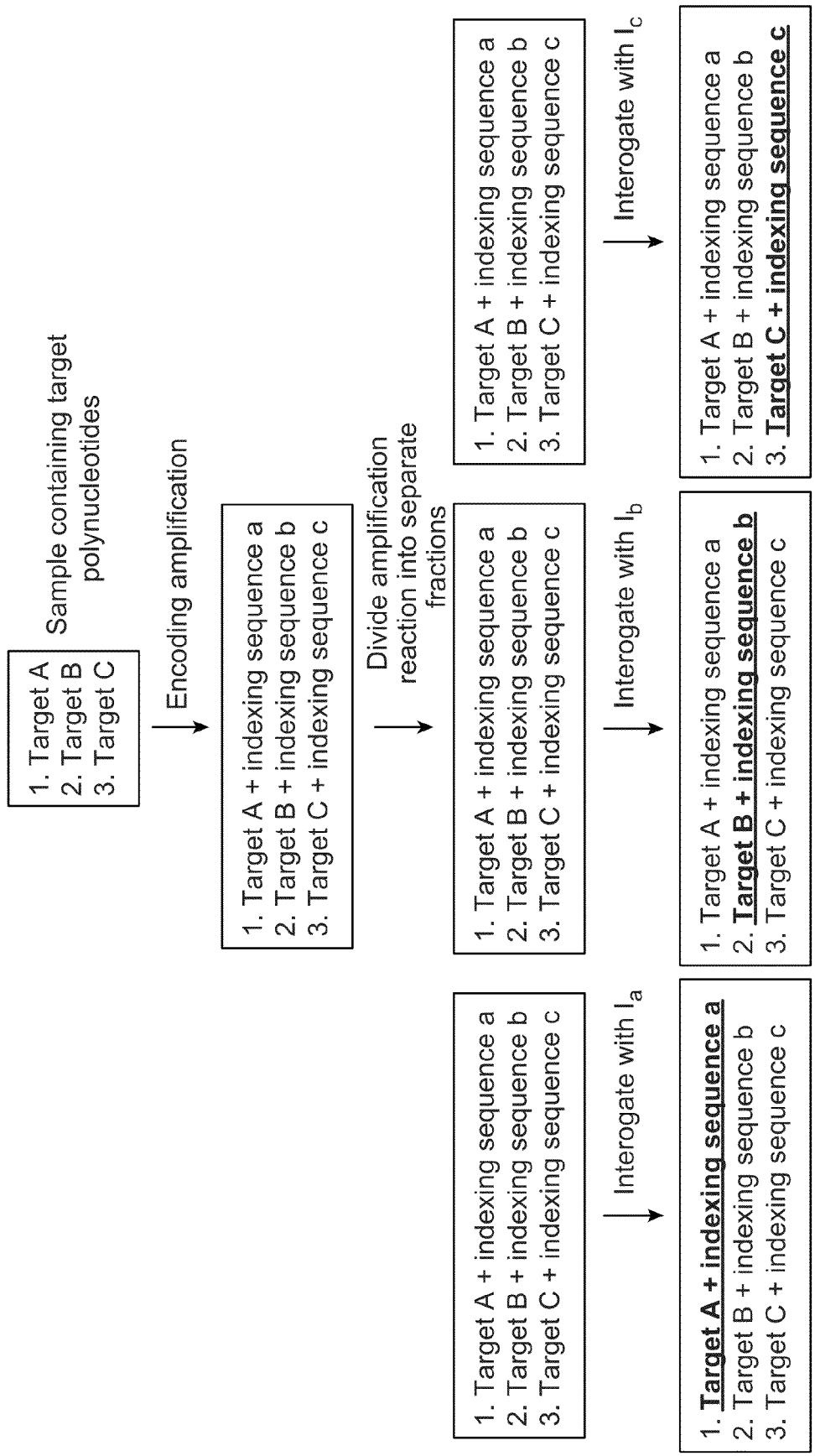
FIGS. 6 and 7 are flow charts illustrating decoding using indexed probes and indexing sequences.

The designations "universal" and "indexed" describe the relationship, in a specified assay, of probe-binding or indexing sequences and the target sequences with which they are associated. A probe-binding sequence or indexing sequence that does not uniquely identify the target sequence with which it is associated can be considered a "universal" sequence. For example, a sample may be assayed for the presence of 48 target sequences by associating each of the 48 target sequences with the same probe-binding sequences and detecting amplicons containing the probe-binding sequences using a single "universal" detection probe with π sequences that recognizes the probe-binding sequences. Each of the 48 target sequences could be associated with a different indexing sequence, and distinguished from each other using 48 different decoding primers. FIG. 6 illustrates detecting three target sequences based on associating each with universal probe-binding sequences, and decoding using decoding primers that recognize one of three indexing sequences.

Alternatively, a sample could be assayed for the presence of 48 target sequences by associating each of the 48 target sequences with a different probe-binding sequence. Each of the 48 target sequences could be distinguished using based on annealing of one of 48 uniquely labeled detection probes. In this case, each of the 48 target sequences could be associated with the same indexing sequence, and a single "universal" decoding primer, or primer pair, could be used in detection of the 48 targets. Given the expense of producing labeled detection probes, of these two alternatives, the use of a universal detection probe has the advantages of lower cost.

Figure 7:
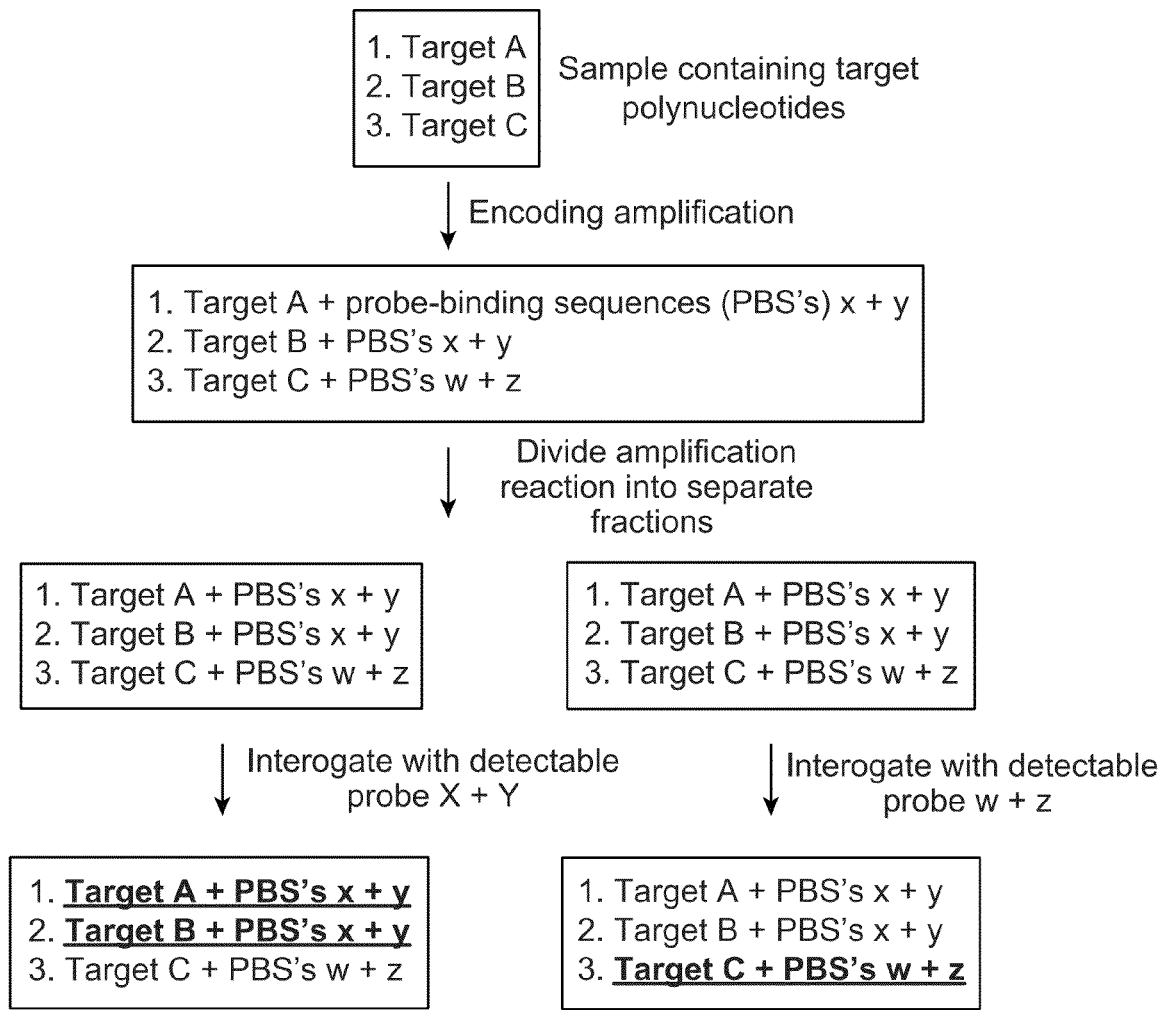

FIG. 7 illustrates assaying for three target sequences by associating each target sequence with one of two combinations of probe-binding sequences (X+Y or W+Z) and using two uniquely labeled detection probes. It will be apparent that the same strategy could be by associating three target sequences with one of two indexing sequences, and using a pair of decoding primers and a single universal probe to detect the presence or absence of target.

It will be apparent that, if desired, using indexed probe-binding sequences and/or indexing sequences can be used to selectively detect individual target sequences or defined sub-genuses of target sequences. By using various combinations of indexing sequences and indexed probe-binding sequences analyses of considerable complexity can be carried out.

2.3.5 Self-Digesting Probe with No Decoding Primer

Figure 30:
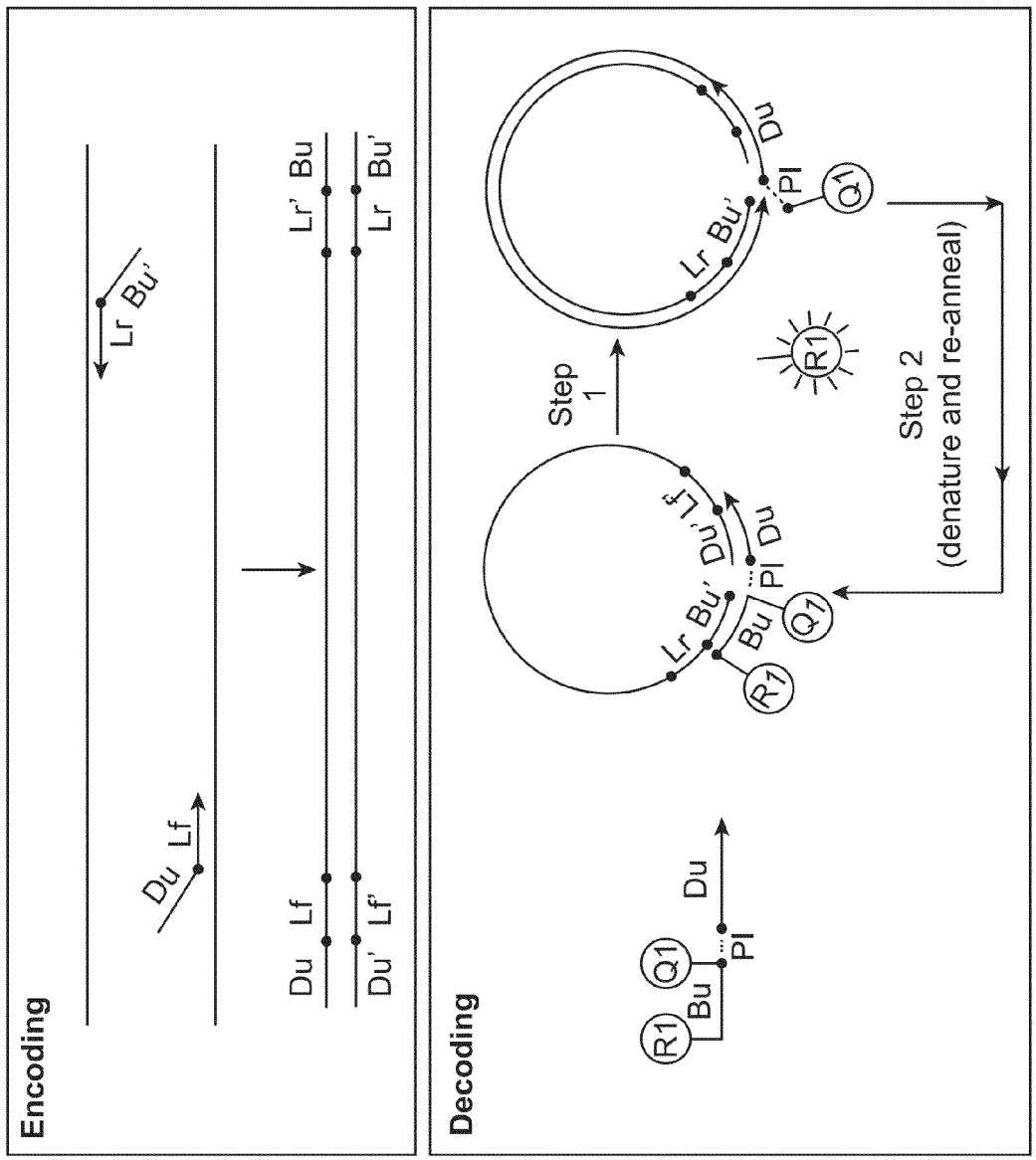
FIG. 30 shows an assay using an extendible self-digesting probe without decoding primers.

As illustrated in FIG. 30 methods are provided in which "self-digesting" probes are used without a decoding primer. As illustrated, an initial encoding amplification associates each target sequence with a pair of probe-binding sequences (Du and Bu') using encoding primers with the structure 5'-P-T-3'. The amplicons are combined with a hydrolysis type detection probe having the structure 5'-$P_1$-L-$P_2$'-3' (denoted in FIG. 30 as 5'-Bu-PI-Du-3'). Importantly, the 3'-terminus of the detection probe is not blocked. That is, the detection probe can serve as a DNA polymerase primer to extend the detection probe at the 3' end, using the amplicon as template. Extension results in cleavage of the detection probe releasing the signal moiety (reporter), resulting in a detectable change in the fluorescent signal.

The extended probe-amplicon complex is then denatured and a new detection probe molecule is allowed to anneal to the amplicon, repeating the extension and generation of signal. This can be accomplished using, without limitation, a PCR thermocycle profile comprising denaturation at 95° C. for 5 seconds followed by extension at 60° C. for 1 minute.

This assay can be carried out by conducting the encoding step and the decoding (detection) step in the same vessel or well (i.e., with no "preamplification" step). In this embodiment the forward encoding primer is included at a decreased concentration compared to the reverse encoding primer (e.g., a 10-fold lower concentration) so that one amplicon strand is produced asymmetrically. This allows to the encoding reaction to occur, but favors production of signal through amplification in the detection step. Alternatively, the assay can be carried out using a distribution step.

2.3.6 Self-Digesting Probe with One Decoding Primer

Figure 32:
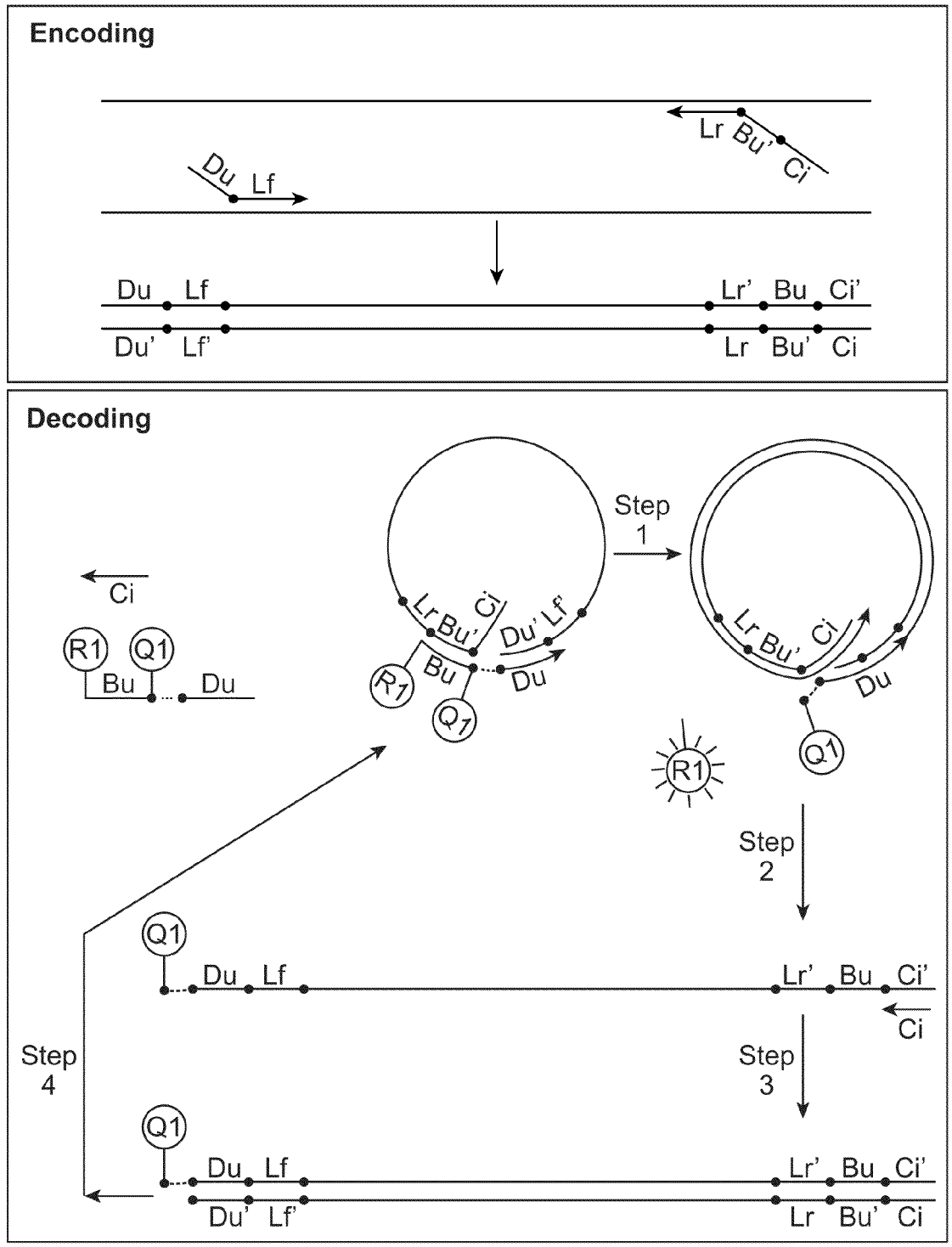
FIG. 32 shows an assay using a non-extendible self-digesting probe and one decoding primer.

FIG. 32 illustrates an embodiment in which a single decoding primer is used. As illustrated, an initial encoding amplification associates each target sequence with a pair of probe-binding sequences, denoted Bu and Du. The encoding primers have the structure 5'-Du-Lf-3' (forward encoding primer) and 5'-Ci-Bu'-Lr-3' (reverse encoding primer) in which Ci is an indexing primer. The amplicons are combined with a FRET-type detection probe having the structure 5'-Bu-PI-Du-3', where "PI" denotes a linker. A DNA polymerase with 5' nuclease activity is used to extend the detection probe at the 3' end using the amplicon as template, eventually cleaving the signal moiety (reporter) from the detection probe, resulting in a detectable change in the fluorescent signal. As shown in the figure, extension of the probe continues after the reporter is released and terminates at the linker moiety.

The signal generated in this process may be, and preferably is, increased by amplifying the probe extension product as described in the example using a reverse decoding primer.

In one embodiment of this assay, the encoding primers may be used in the same reaction as the extendable probe and the single reverse decoding primer (i.e., in the same reaction volume). In this embodiment the initial priming steps are run at an elevated temperature (approximately 72° C.) for an extended period of time (12-20 minutes) to tag and create a paired end amplicon that has perfect homology to the encoding primers. Because the melting temperature of the encoding primers (up to 65 bases) hybrid exceeds the temperature at which extension occurs as well as the melting temperature of the extendable probe primer element, and the reverse decoding primer: the encoding reaction can be conducted in the same vessel as the decoding reaction.

Alternatively, the encoding step can be carried out in a first reaction volume, the first reaction volume can be distributed to multiple second reaction volumes (e.g., in droplets, by partitioning, etc.) and the decoding steps can be carried out in the second reaction volumes.

When the assay does not include a distribution step, multiplexing can accomplished by using multiple probes having different reporter systems to distinguish signal generated from different target sequences.

When the assay includes a distribution step, multiplexing can (also) accomplished by varying the indexing sequence and using different reverse decoding primers in different second reaction volumes.

3. Illustrations 3.1 Illustration 1: Encoding Primers and Universal Probes

FIG. 8 illustrates an encoding amplification and detection steps. Although for simplicity a single target is shown, the encoding step is usually a multiplex reaction.

As illustrated in FIG. 8, during the encoding step, the target sequence is amplified using a pair of encoding primers. In this example, encoding primers are used to incorporate primer sequences that are indexed to correspond to each of the specific target segments being interrogated. Indexing sequences $A_i$ and $C_i$ are shown. These encoding primers also incorporate probe sequence information (i.e., probe-binding sequences $B_u$ and $D_u$). Thus, each of the two encoding primers contains part of the sequence information recognized by the detectable probe.

In the encoding reaction, the encoding primer sequences are incorporated into the 5' regions of each strand of the amplicon and complementary sequences are incorporated in the second strand. In this example, proceeding in a 5' to 3' direction, each encoding primer comprises an indexing sequence (Ai, Ci), a probe binding sequence (Bu, Du), and a target-binding sequence ($T_1$, $T_2$). The complementary strand therefore comprises probe-binding sequences (Bu', Du) flanking the amplified target sequence. In the encoding step, a double-stranded amplicon is produced. For convenience the two strands can be referred to as the "upper strand" (5'-Ai . . . -3') and the "lower strand" (5'-Ai' . . . -3').

FIG. 8 also illustrates a detection step. Amplicons containing amplified target sequences are detected using a fluorogenic detection probe that hybridizes to both of the probe-binding sequences. For simplicity, the fluorogenic probe is shown in this example as a hydrolysis probe that would be cleaved by the 5' nuclease activity of the DNA polymerase used in the detection PCR step. As shown, the detection probe comprises π sequences Bu and Du', which hybridize to the corresponding probe-binding sequences Bu' and Du incorporated into the lower strand of the amplicon. Because the fluorogenic probe hybridizes to sequences derived from both primers, the detection step maintains the two primer specificity of the encoding PCR step. In the detection step shown in FIG. 8, the decoding primer $A_i$ is annealed to the indexing sequence $A_i'$ on the lower strand and extended using a DNA polymerase with 5' nuclease activity. A second decoding primer, $C_i$, is used to regenerate the double-stranded amplicon using the upper strand as template. Denaturation of the amplicon allows another round of signal generation.

It will be recognized that, the detection probe may also be a molecular beacon probe. For use of a molecular beacon, a short hairpin structure (4-6 base pairs) is engineered between the Reporter (R1) and Quencher (Q). In another variation, the encoding step is performed using ligation oligonucleotides and ligase rather than using PCR.

While only one target polynucleotide is illustrated in FIG. 8, it will be understood that the encoding step may be a multiplex reaction comprising encoding primers that bind to multiple different target sequences. In one embodiment, each encoding primer pair has a different combination of target-binding sequences ($T_1/T_2, \ldots T_m/T_n$, where m and n are integers), indexing sequences (A, C) and probe-binding sequences (B, D). The probe-binding sequences may be shared by all of the amplicons generated in an assay. For example, if all of the encoding primer pairs in the reaction share the same probe binding sequences, it is possible to detect all target polynucleotides using the same labeled detection probe, e.g., a "universal probe." Use of common probe-binding sequences has the advantage of reducing the costs associated with using target-specific probes while maintaining two primer specificity of the encoding reaction. Similarly, the indexing sequences may be shared by all of the amplicons generated in an assay, or may be unique to a particular target sequence or genus of target sequences. In the latter case, individual genera, subgenera or species can be distinguished using decoding primers specific for the particular genus or species.

Figure 33:
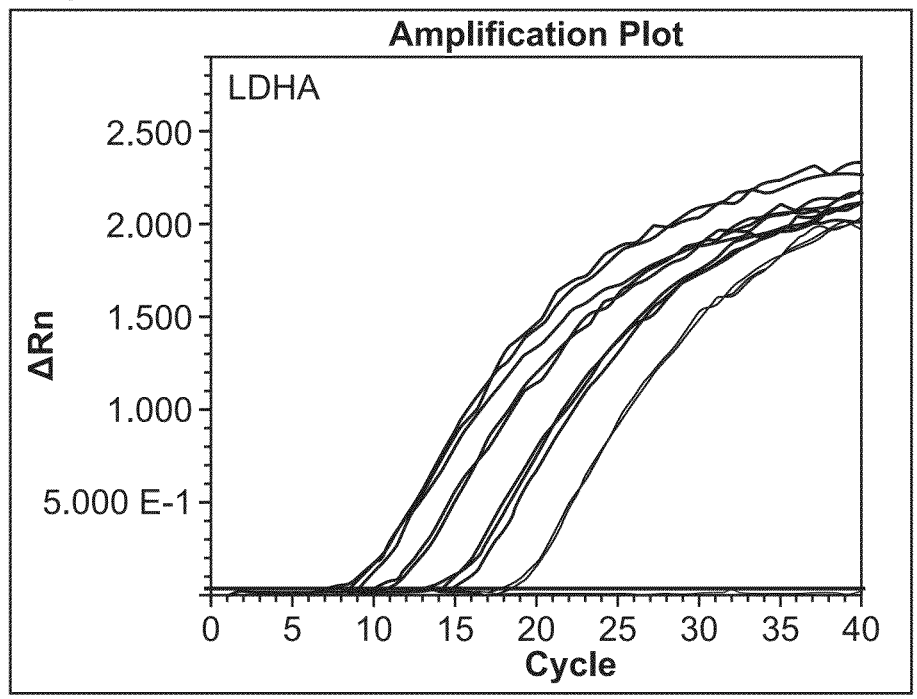
FIG. 33 shows the results of an assay.

Using this process several genes can be analyzed. FIG. 33 shows the results of three decoding PCR reactions conducted from a single multiplexed encoding reaction. In this assay, in the multiplex encoding amplification, three encoding primer sets were used to amplify three target sequences. Individual portions of the resulting amplification mixture were decoded with using decoding primers specific for each encoded target sequence. These decoding reactions demonstrate acceptable linearity over at least four orders of magnitude using a conventional real-time PCR instrument (Applied Biosystems 7900HT).

In a separate experiment a similar set of twelve decoding reactions, each replicated six times, were conducted using a Fluidigm Dynamic Array (96.96). These reactions also demonstrated a linear response over four orders of magnitude for several of the expressed genes analyzed in this reaction. The experiments demonstrate the utility of the universal probe construct which enables the detection of many different genes from a single multiplexed encoding reaction.

Figure 9:
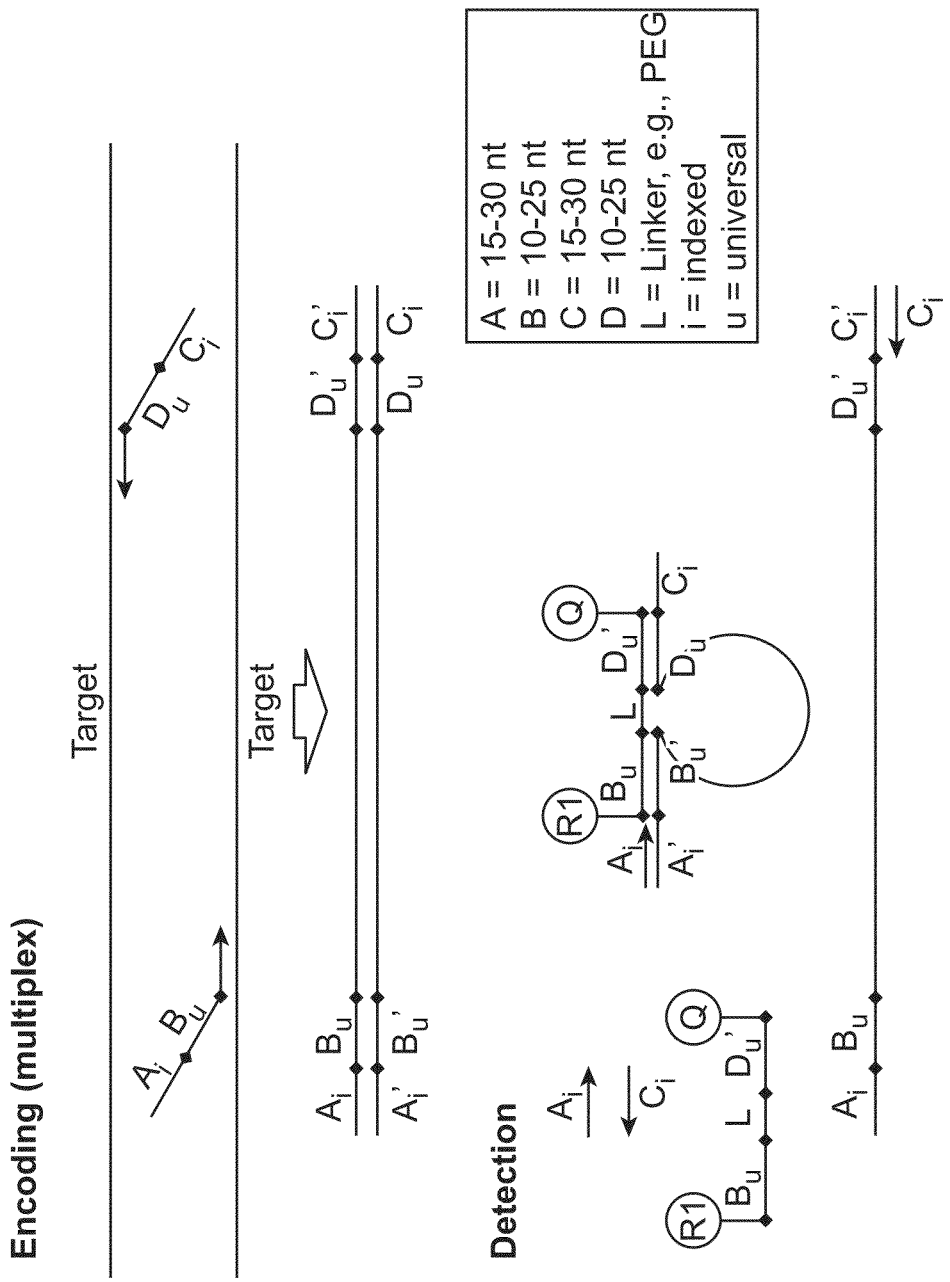

FIG. 9 shows that in certain embodiments the detection probe comprises a non-nucleotide linker (L) between the detection probe π sequences (Bu, Du'). For example, the non-nucleotide linker can comprise polyethylene glycol (PEG). The non-nucleotide linker L may improve the kinetics and stability of probe hybridization.

3.2 Illustration 2: Indexing Probe Segments

Figure 11:
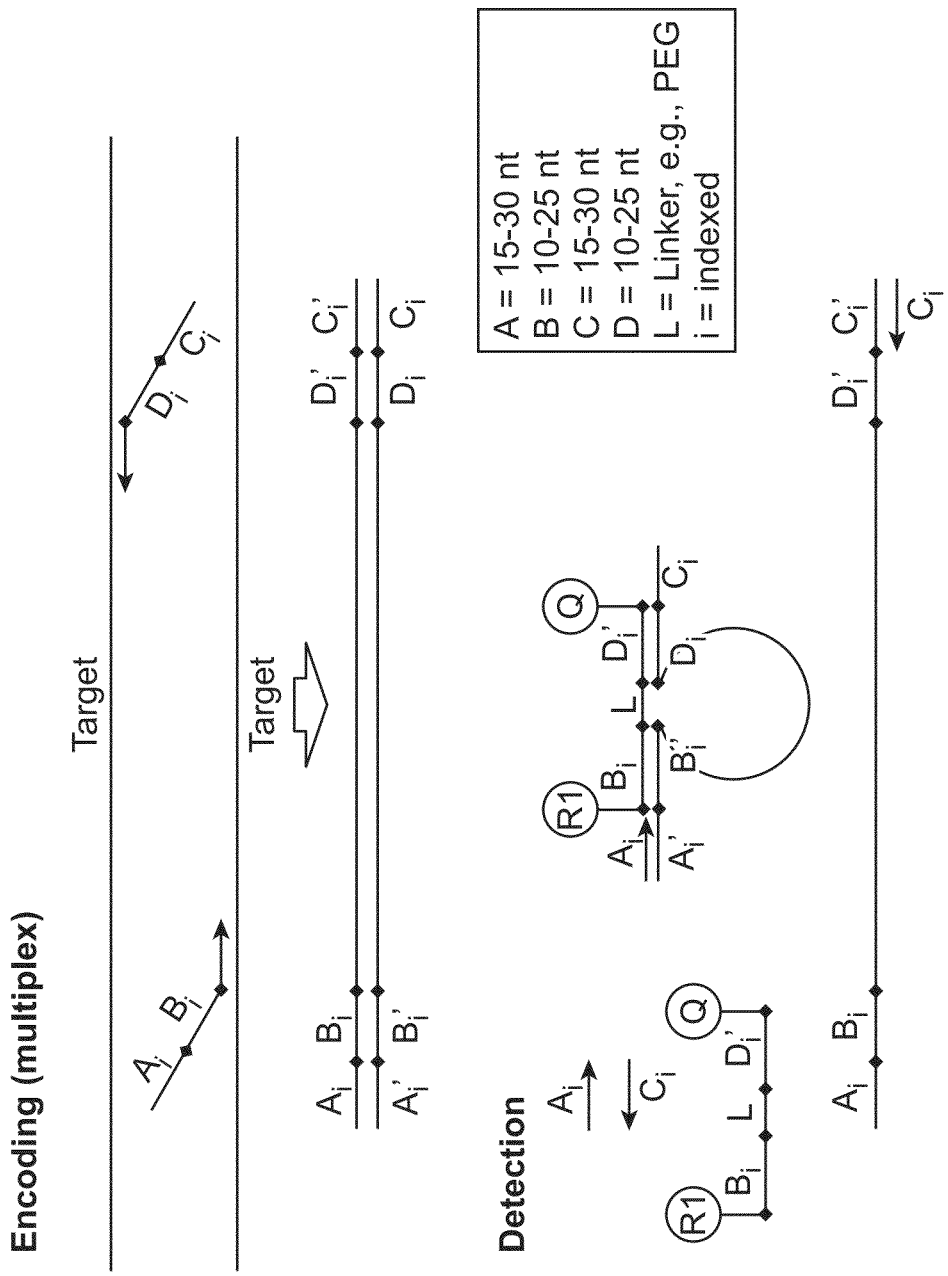

FIG. 10 illustrates amplification and detection of a target sequence using encoding primers that comprise indexed probe-binding sequences (Bi and Di) and indexed indexing sequences (Ai, Ci). As illustrated in the figure, rather than use a Universal Probe, it is possible to index the probe segments (i.e., probe binding sequences) and thus have an indexed probe sequence associated with each set of indexed encoding and decoding (indexing) primers. This may have benefits in terms of the specificity of the overall experiment. FIG. 11 illustrates that in certain embodiments the detection probe comprises a non-nucleotide linker (L) between the detection probe π sequences (Bu, Du').

3.3. Illustration 3: Detection Probe Configurations

The diagrams above have been drawn with probes that have the reporter at the 5' end and the quencher at the 3' end. FIGS. 5 and 12-15 illustrate various probe configurations useful in the present methods. For example, it is possible to move the quencher to the middle of the probe, the reporter to the middle of the probe, or both reporter and quencher away from the ends of the probe. The positions of reporter and quencher can be reversed (particularly when molecular beacon probes are used).

Figure 12:
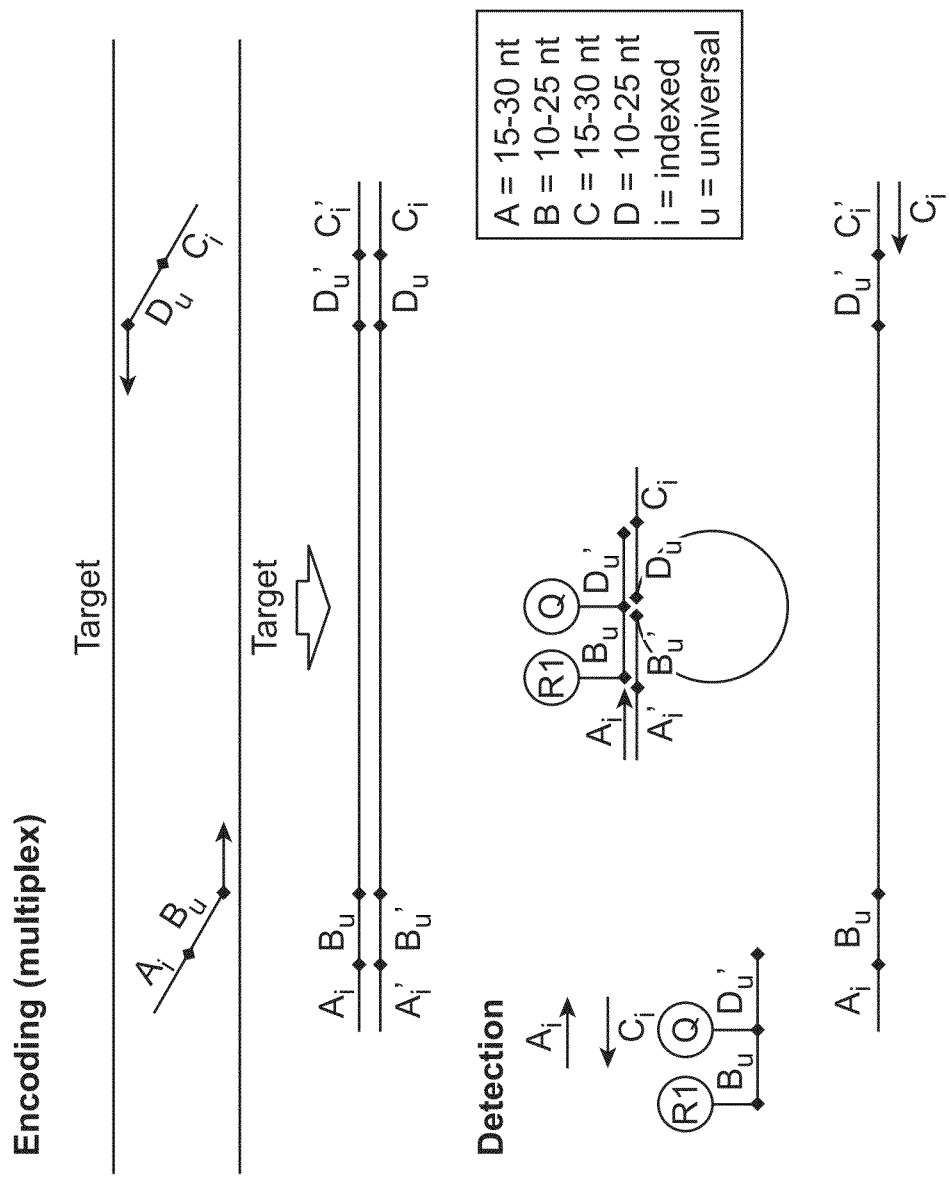

FIG. 12 shows the quencher Q located in the interior (i.e., not at the terminus) of a detection probe. In the figure a universal probe is used, with indexing sequences.

FIG. 13 is similar to FIG. 12, but shows the quencher Q located in the middle of an indexing detection probe, between the probe π sequences Bi and Di'.

Figure 14:
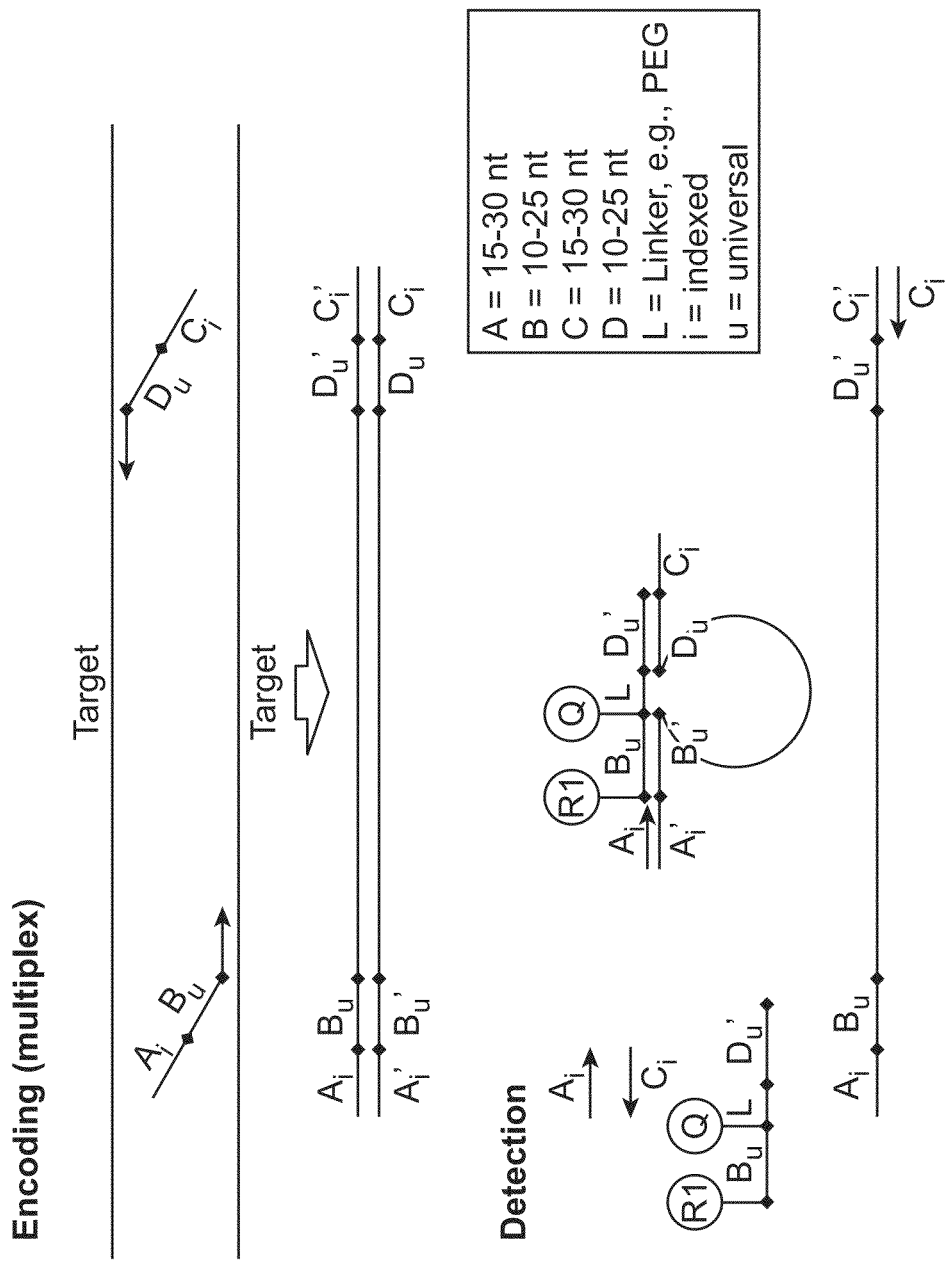

FIG. 14 illustrates a universal probe having a linker (e.g., a non-nucleotide linker or an intervening nucleotide sequence). In this example, the reporter and quencher are both positioned within a π segment hybridized to a single probe binding sequence.

Figure 15:
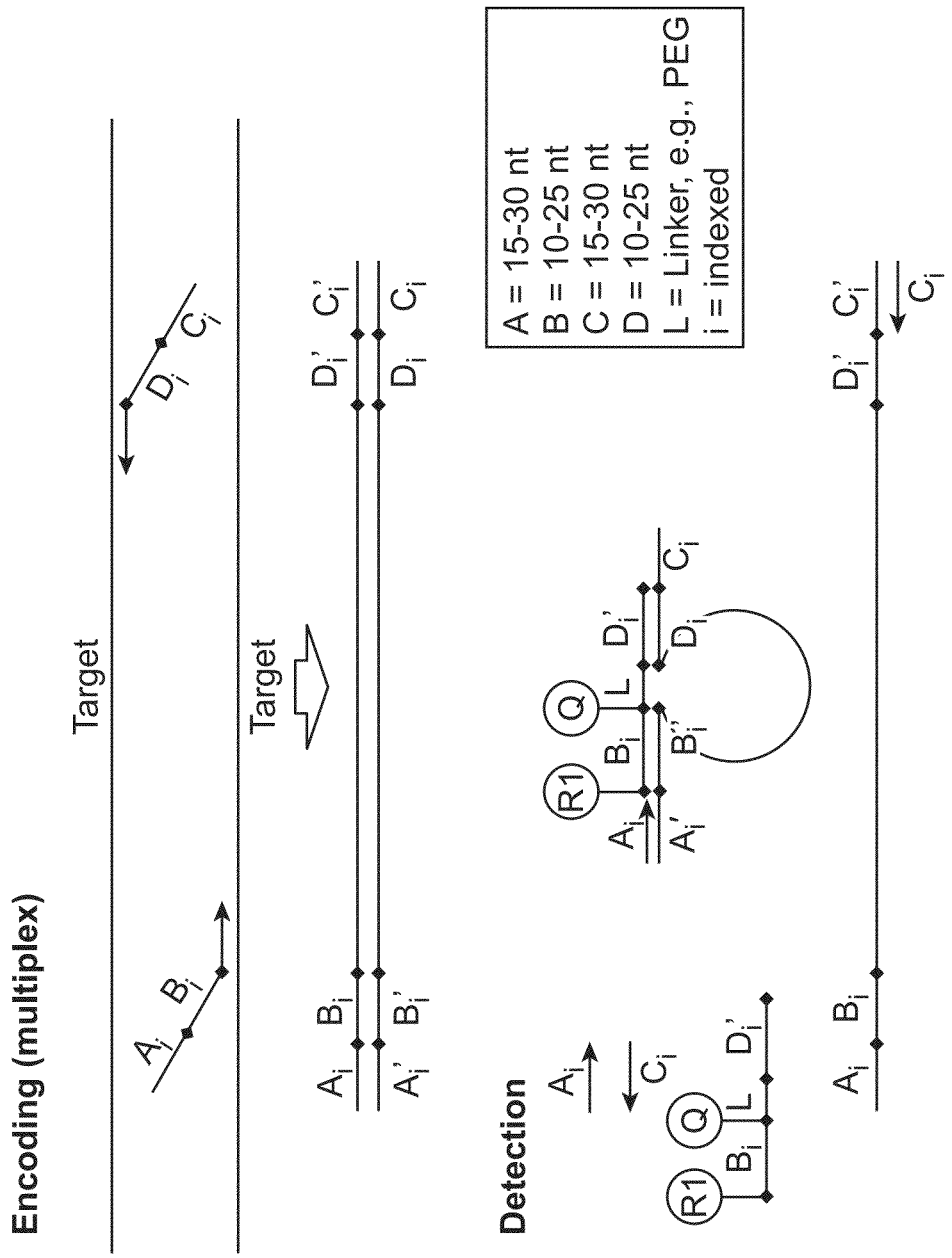

FIG. 15 illustrates a detection probe with indexed π sequences and having a linker and quencher located between the probe π sequences Bi and Di'.

In other embodiments (not shown), the reporter is, or both the reporter and quencher are, located away from the terminus of the probe. These diagrams have been drawn with probes that have the reporter at the 5' end and the quencher at the 3' end. If molecular beacon probes are used, the positions of reporter and quencher can be reversed.

3.4 Illustration 4: Ouroboros Configuration

FIG. 16 illustrates an alternative scheme that maintains two primer specificity for the probe by essentially reversing the orientation of the probe. This entails taking each encoding primer and exchanging the position of the probe segment (i.e., probe binding sequence) and the decoding primer segment (i.e., indexing sequence) All the variations of indexed probes, inclusion of a linker in the probes, and moving the positions of Reporter and/or Quencher can be used.

As shown in FIG. 16, the relative positions of the indexing sequence(s) and probe-binding sequences are reversed in the encoding primers. Thus, proceeding in a 5' to 3' direction, each encoding primer comprises a probe-binding sequence (Au, Cu), an indexing sequence (Bi, Di), and a target-binding sequence ($T_1, T_2$). Amplification of the target sequence during the encoding step results in association of the encoding primer sequence and target sequence, producing amplicons in which the target sequence is flanked by the probe-binding sequences and, optionally, indexing sequence(s) between the probe-binding sequences and target sequence.

In the detection step, the detectably labeled probe comprises sequences Au and Cu' that hybridize to the probe-binding sequences Au' and Cu. The detection step comprises combining the amplified target polynucleotide with the detectable probe(s), decoding primers Au-Bi and Di-Cu, and DNA polymerase under conditions sufficient for primer extension. Primer $B_i$ is extended by DNA polymerase until the nuclease activity of the polymerase releases the reporter dye, separating it from the quencher and resulting in a detectable signal.

FIG. 17 is similar to FIG. 16, but shows encoding primers with indexed probe-binding sequences.

Figure 18:
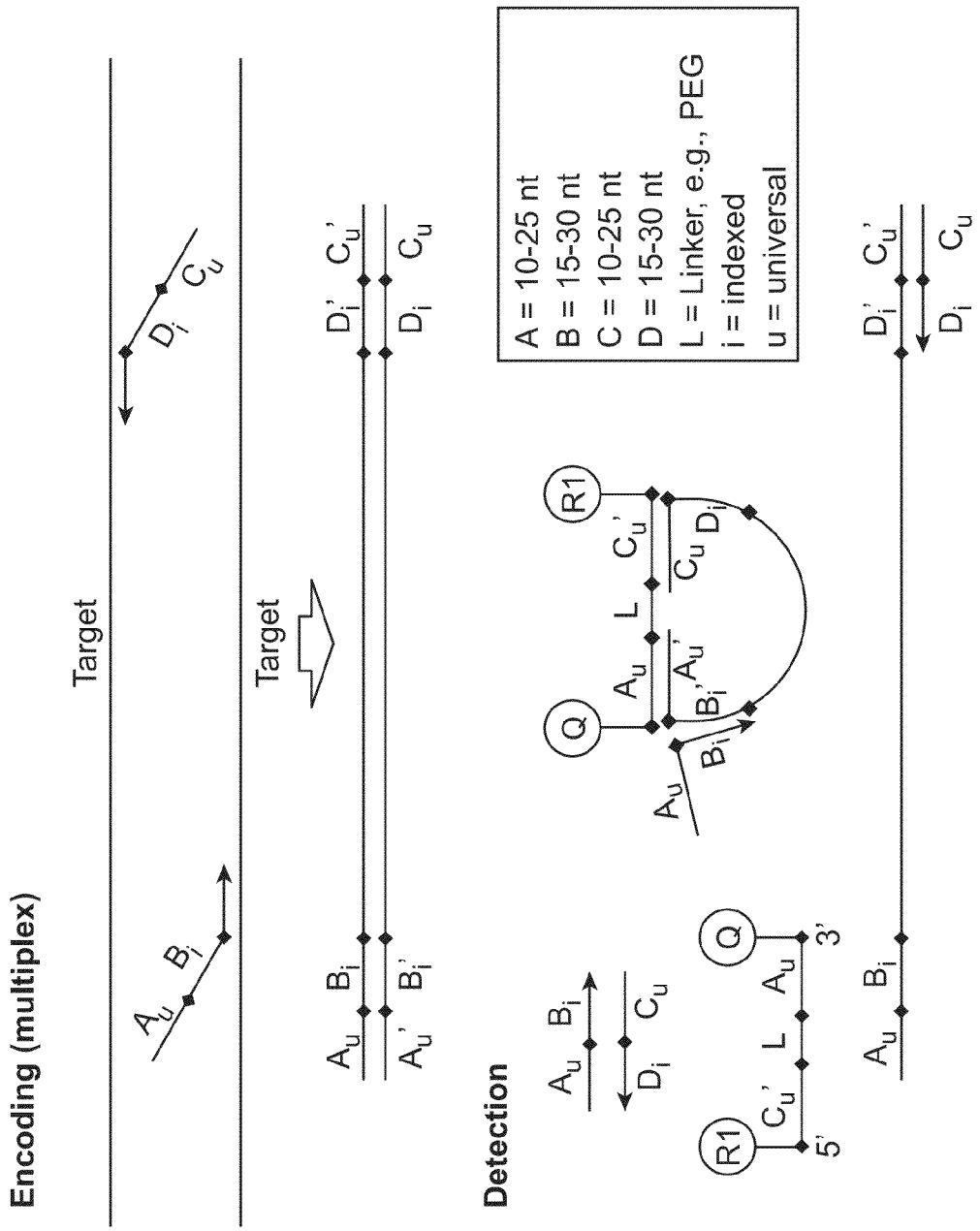
Figure 19:
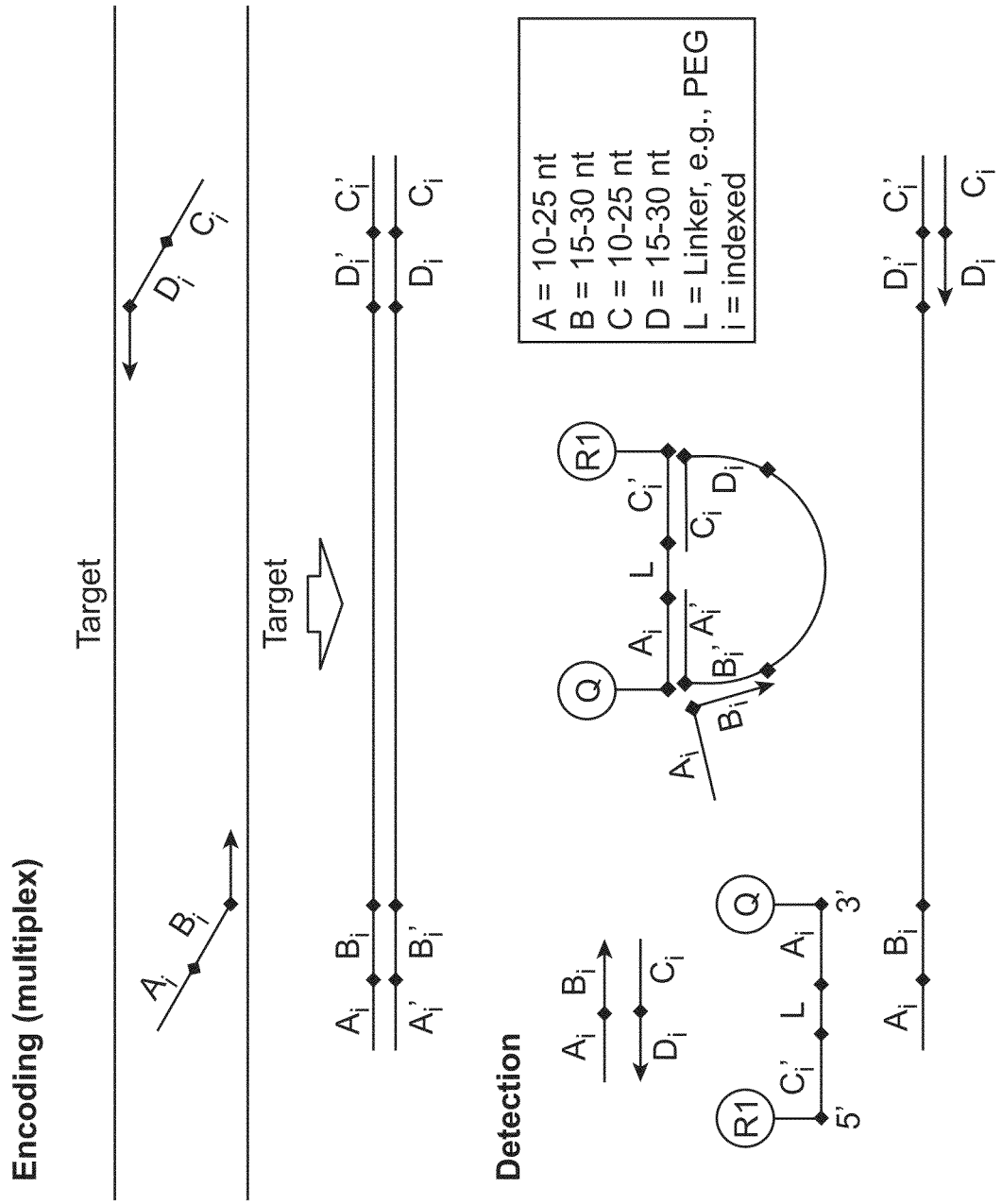
Figure 20:
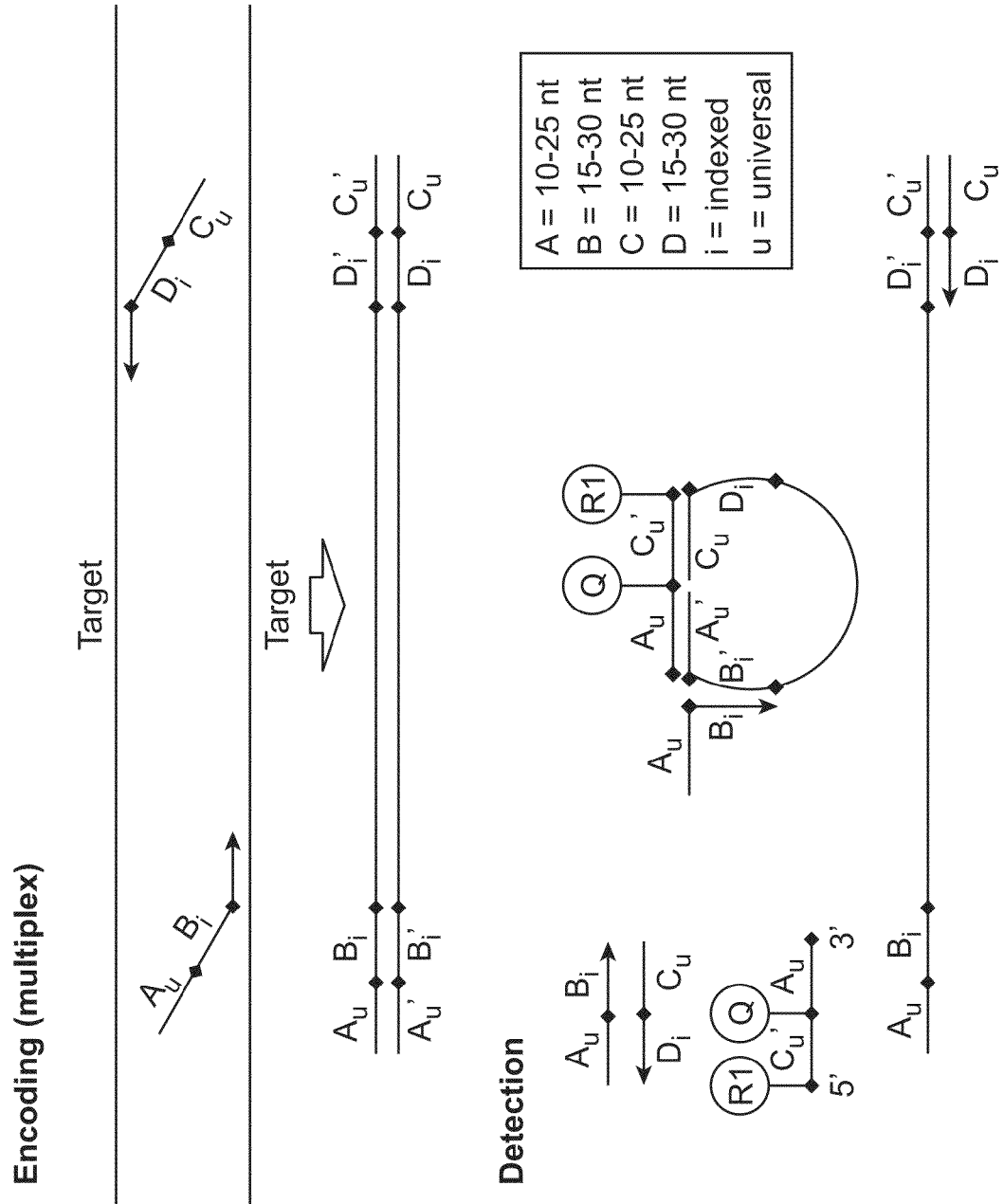
Figure 21:
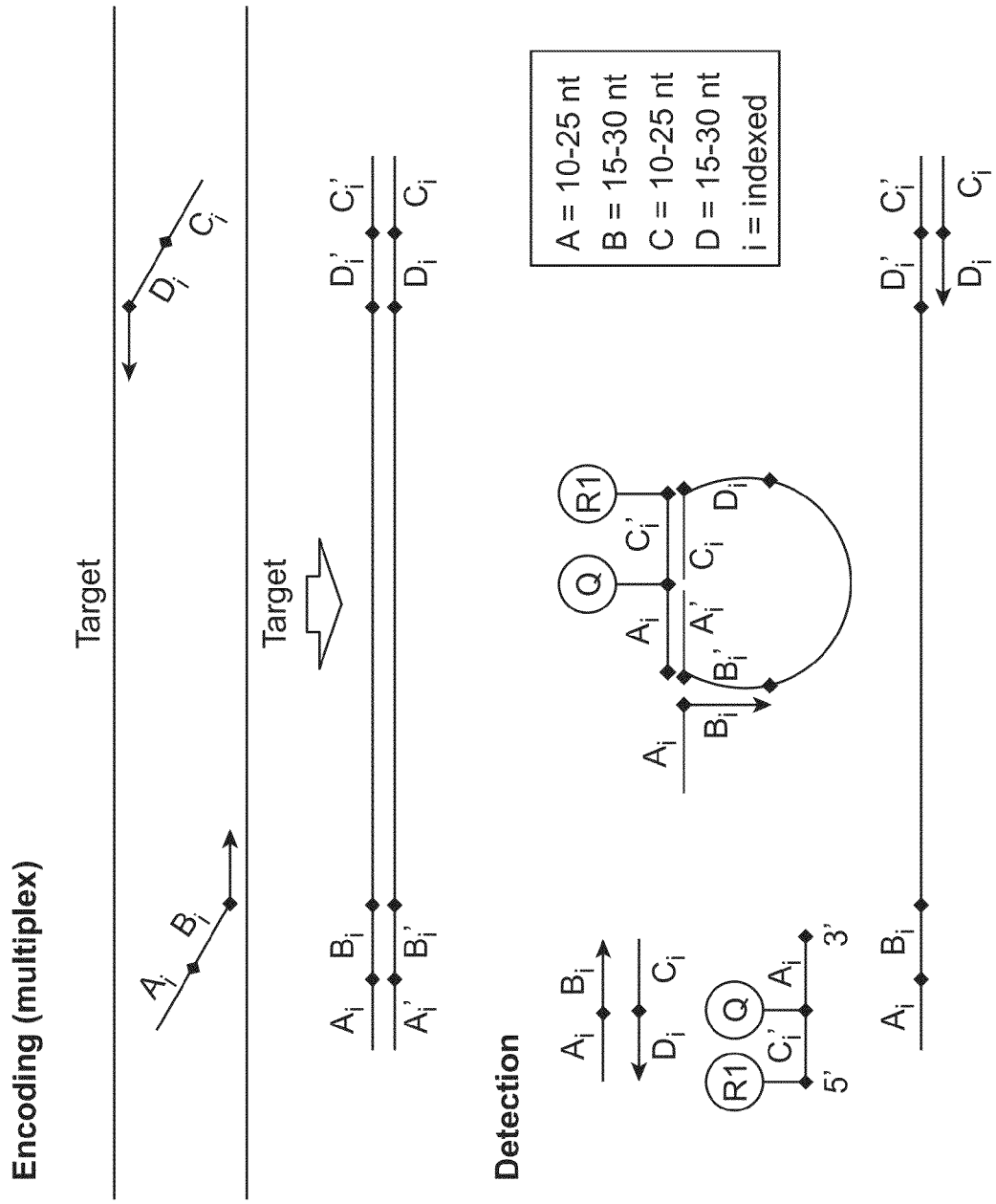

FIGS. 18 and 19 are similar to FIGS. 16 and 17, respectively, but shows a detection probe that comprises a linker between the probe's π segments.

FIGS. 20-23 illustrate a variety of detection probe geometries.

Figure 22:
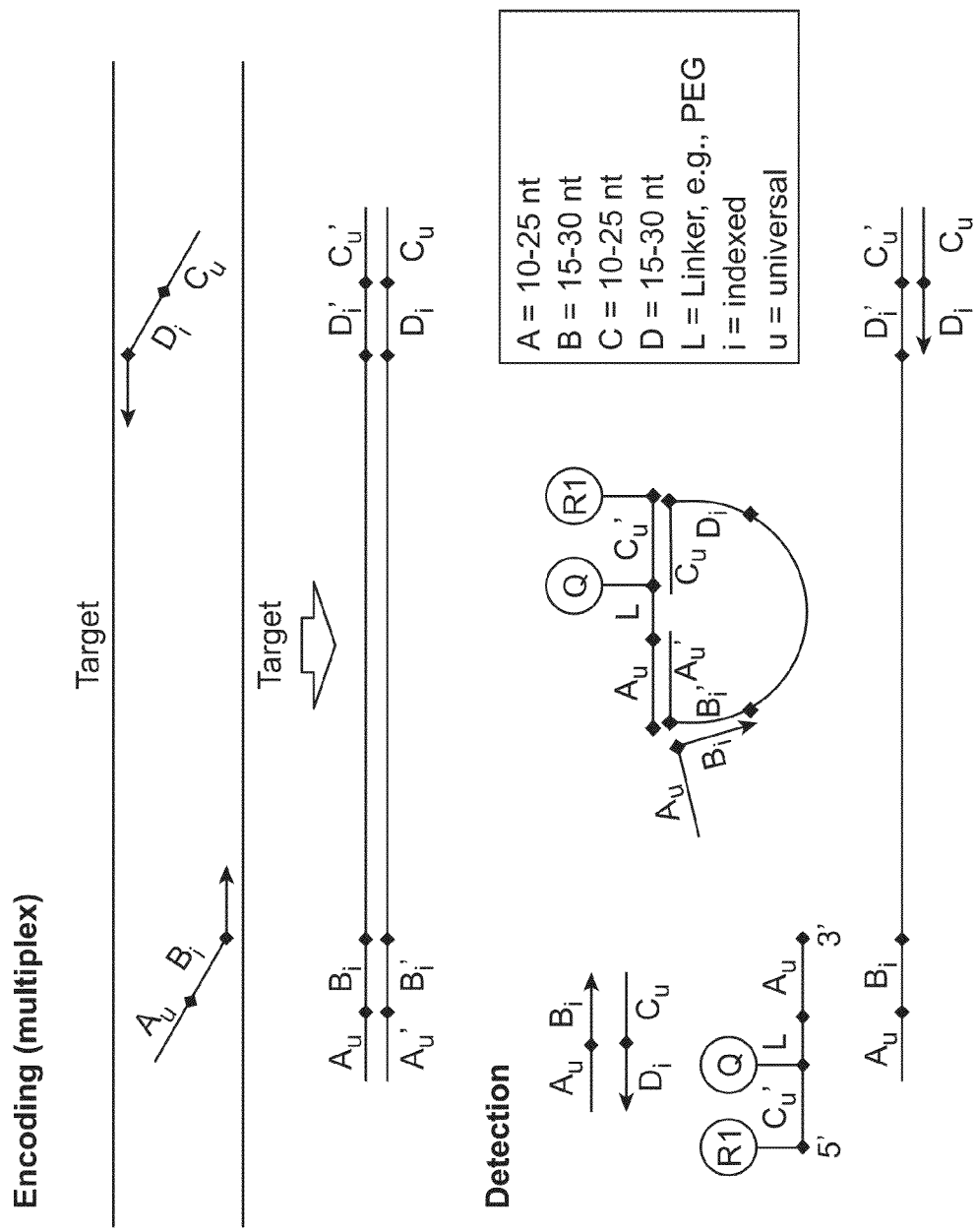
Figure 23:
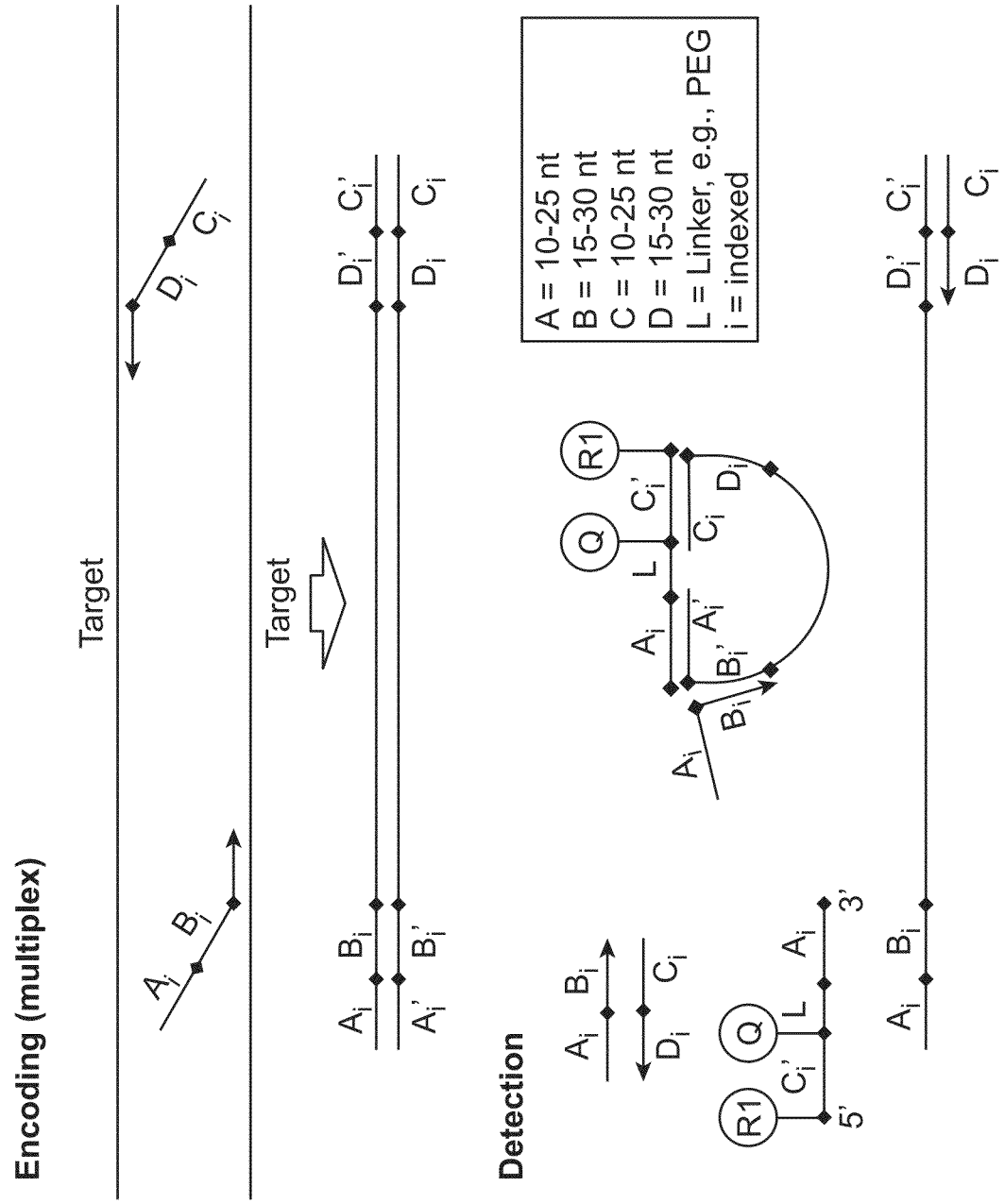
Figure 29:
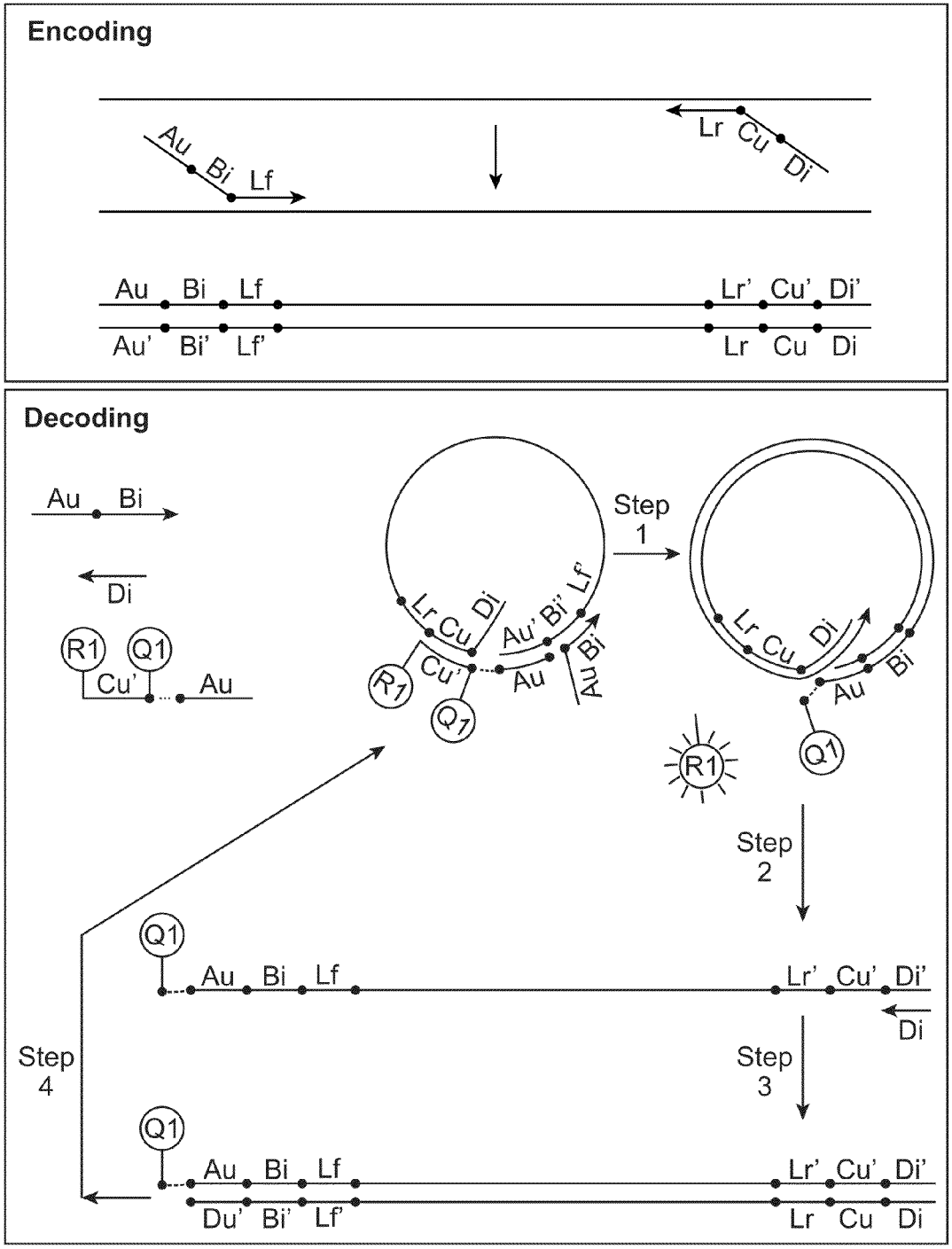
FIG. 29 illustrates a variation of the Ouroboros approach shown in FIG. 22.

FIG. 29 illustrates a variation of the Ouroboros approach shown in FIG. 22. In this approach, the encoding reaction uses an encoding primer set in which a first encoding primer has the structure 5'-P-I-T-3' and the second encoding primer has the structure 5'-I-P-T-3'. In FIG. 29 the probe binding sequences are denoted Au and Cu, the target binding sequences are denoted Bi and Di and the target binding sequences are denoted Lf and Lr. Using this process, encoding and decoding reactions can be carried out to detect target sequence (FIG. 34A). In this example four concentrations of the cDNA generated from an encoding reaction were used (see FIG. 29) were used in a PCR thermocycle profile comprising: 50° C.-2 min, 95° C.—10 min, 2 cycles of 95° C.—5 sec, 64° C.-12 min and 40 cycles of 96° C.-5 sec, 60° C.-1 min. This reaction generates a linear response ($r^2$=0.996 based on Ct value) to 10× serially diluted cDNA.

3.5 Illustration 5: Genotyping

This example demonstrates that either probe configuration can be used for genotyping as well. This involves using allele-specific PCR in the encoding step in order to associate a distinct decoding primer segment (i.e., indexing sequence) and probe segment (i.e., probe binding sequences) with each allele.

Figure 24:
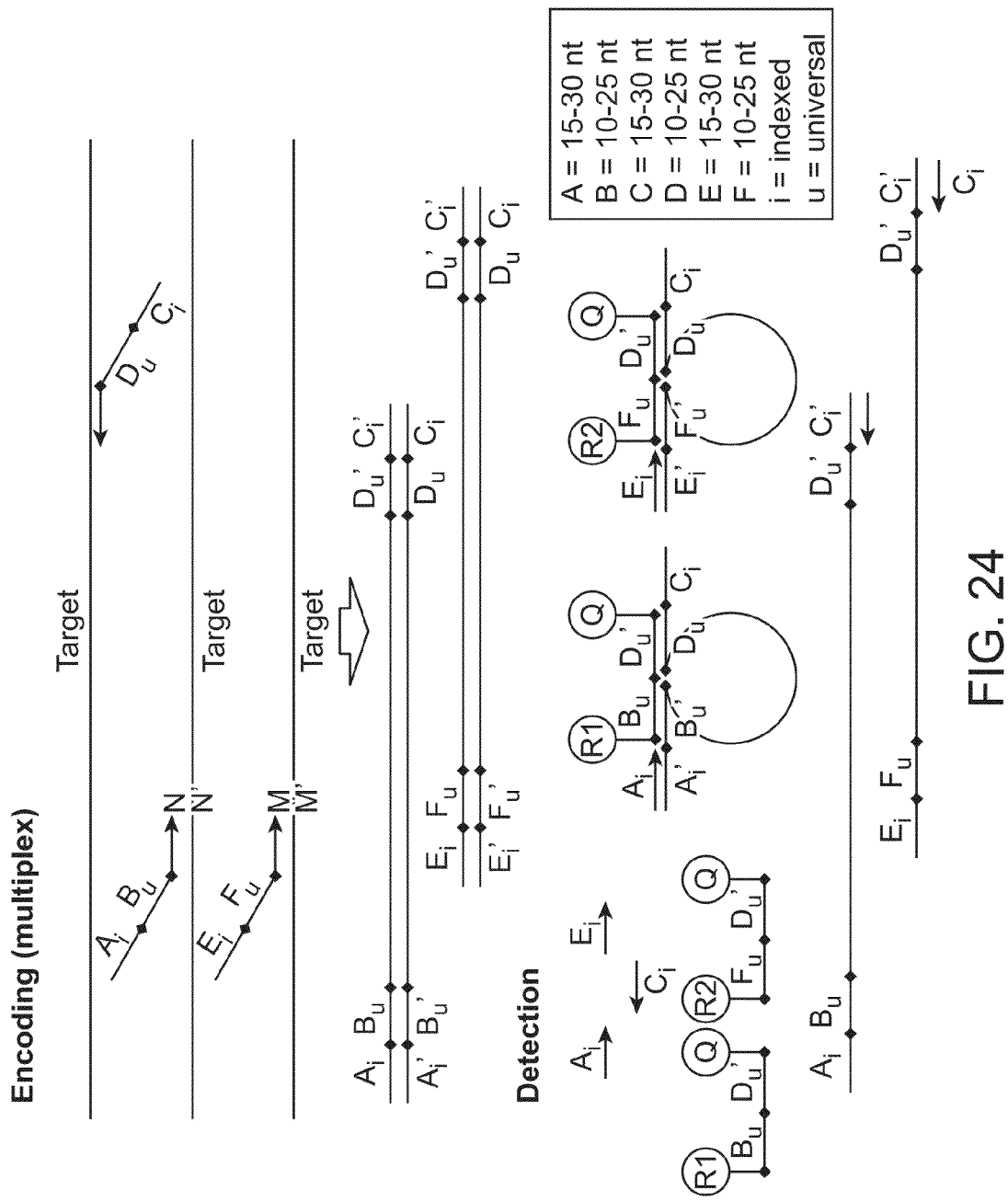
FIGS. 24-25 illustrate genotyping using the methods of the invention.

FIG. 24 illustrates the use of encoding primers and two differently labeled detection probes. In the encoding step, three encoding primers are used (i.e., two encoding primer pairs, including one common primer). The two allele-specific encoding primers, $A_i$-$B_u$-$T_N$ and $E_i$-$F_u$-$T_M$, each comprise an allele-specific nucleotide at the 3' end of the target-binding sequence. Under appropriate conditions, the encoding primers hybridize to the target sequence such that the allele-specific primers anneal to their cognate alleles, represented by complementary nucleotides N' and M', respectively. If the allele-specific encoding primer is mismatched at the 3' end (i.e.; not complementary to the corresponding target nucleotide sequence), the primer will not serve as an efficient template for primer extension. Therefore, amplification of target sequences that are complementary to the 3' nucleotide of the allele-specific primer will be favored, resulting in production of a greater number of copies comprising the corresponding allele. Amplification of the target sequence results in incorporation of the encoding primer sequences into the resulting amplicons, thereby associating each allele-specific target sequence with allele-specific probe-binding sequence (which is subsequently bound by a detection probe having an allele-specific reporter moiety). Alternatively, or in combination, the allele-specific encoding primer could associate an indexing sequence with the target-binding sequence. In the case of an allele-specific indexing sequence and universal probe-binding sequences, different aliquots of a reaction can be combined with different decoding primers.

Figure 25:
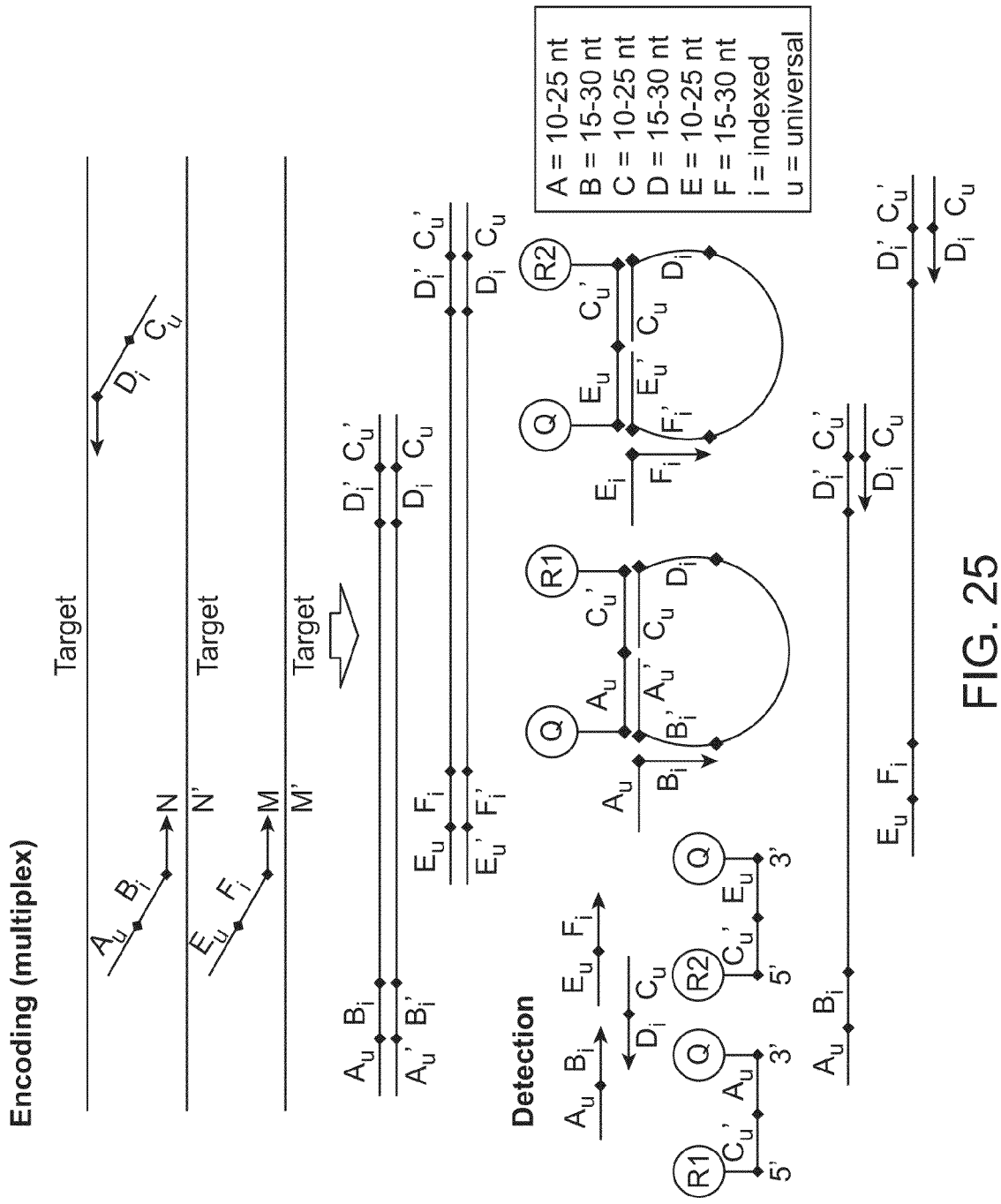

Genotyping can be carried out using all variations of indexing probes, linker configurations, and Reporter and Quencher configurations described above. FIG. 25 illustrates a genotyping reaction using the Ouroboros configuration.

4.6 Illustration 6: Assays Using a Decoding Primer that Binds a Template Sequence An advantage of the Ouroboros configuration is that an encoding step is not required in order to incorporate two-primer specificity into a universal probe. In the illustrations above, detection of a hydrolysis probe requires primer extension from an decoding primer hybridized to an indexing sequence. In a variation illustrated in FIG. 26, each encoding primer pair comprises target-binding sequences ($T_1$, $T_2$) and probe-binding sequences (Au, Cu). As in the above examples, amplification of the target sequence result in amplicons in which the probe-binding sequences of Au and Cu flank the target sequence, thereby associating the target polynucleotide with the probe-binding sequences. In this approach, the decoding primer binds the target-binding sequence in an amplicon, and serves as primer for a primer extension resulting in hydrolysis of a 5' reporter of an associated probe.

Figure 27:
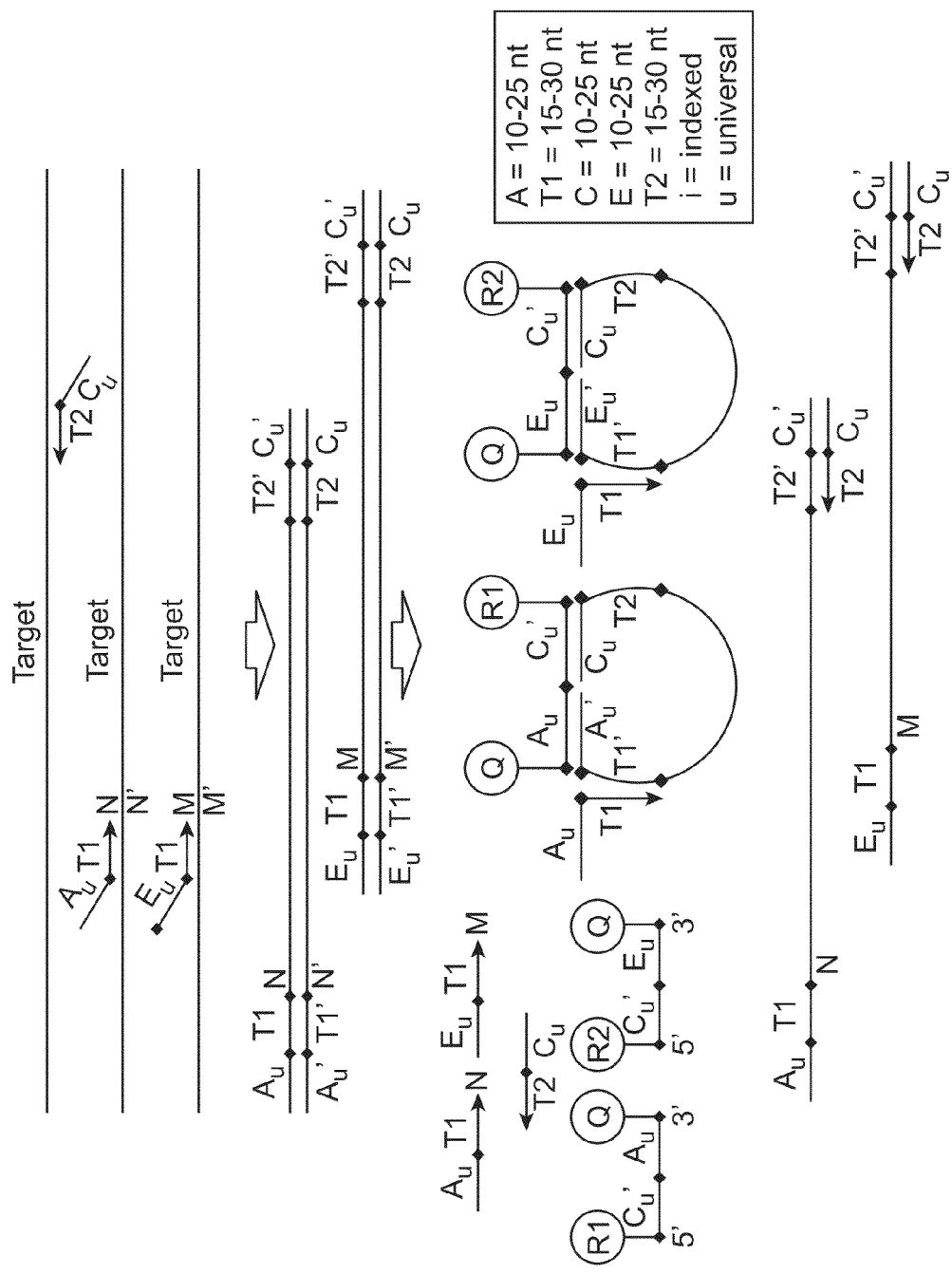

FIG. 27 shows implementation of this approach for genotyping studies. As illustrated, the target sequence is amplified using two allele-specific primers $A_u$, $T_1$ and $E_u$, $T_1$, and a common primer $C_u$, $T_2$. The target-binding sequence of primer $A_u$, $T_1$ comprises a 3' nucleotide N that is complementary to allele-specific nucleotide N'. The target-binding sequence of primer $E_u$, T1 comprises a 3' nucleotide M that is complementary to allele-specific nucleotide M'. As described in Example 7, efficient amplification of the target sequence occurs if the allele-specific primer is complementary to the allele-specific nucleotide present in the target sequence.

In the detection step, the target polynucleotides are combined with primers $A_u$, $T_1$, $E_u$, $T_1$, and $C_u$, $T_2$, two fluorogenic probes, and DNA polymerase under conditions suitable for primer extension. The first probe comprises hybridizing segments $C_u$' and $A_u$ and reporter dye R1. The second probe comprises hybridizing segments $E_u$' and $A_u$ and reporter dye R2. The detection step is as described in Example 4, except that primers $A_u$, $T_1$ and $E_u$, $T_1$ are used for primer extension. If nucleotide N' is present in the amplified product, then reporter R1 will be separated from the quencher. If nucleotide M' is present in the amplified product, then reporter R2 will be separated from the quencher.

3.7 Illustration 7: Assays without Decoding Primers

FIG. 30 illustrates an embodiment in which decoding primers are eliminated and "self-digesting" probes are used. As illustrated, an initial encoding amplification associates each target sequence with a pair of probe-binding sequences. In FIG. 30, the probe-binding sequences are denoted Du and Bu'. The encoding primers also have target binding sequences, denoted "Lf" and "Lr". The encoding primers have the structure 5'-P-T-3' shown in FIG. 30 as 5'-Du-Lf-3' (forward encoding primer) and 5'-Bu'-Lr-3' (reverse encoding primer). The amplicons are combined with a FRET-type detection probe having the structure 5'-$P_1$-L-$P_2$'-3' denoted in the figure as 5'-Bu-PI-Du-3'. A DNA polymerase with 5' nuclease activity is used to extend the detection probe at the 3' end, using the amplicon as template. Extension results in cleavage of the detection probe releasing the signal moiety (reporter), resulting in a detectable change in the fluorescent signal.

In this approach the detection step is carried out by allowing the detection probe to anneal to the product amplicon formed in the encoding reaction. As the probe extends and copies the template (producing a "probe extension product" the polymerase extending the probe at the 3'-end eventually digests probe sequence 5' end (Bu), resulting in the release of the fluorophore attached at the 5' end and an increase in detectable fluorescent emission light. The presence of the linker between the 5' and 3' sequences in the probe results in termination of the probe extension reaction.

FIG. 31 shows results in which two expressed genes were detected in a sample. Separate singleplex encoding reactions were carried out to amplify two target sequences (GAPDH & RPLPO) using the encoding primer sets show in Table 1. For each encoding reaction, diluted aliquots were added into separate reaction wells for decoding.

TABLE 1

|  | Sequence | SEQ ID NO: |
|---|---|---|
| Forward primer 1 | 5'-GACTGAGAGCGGGTGACGTCGAG ATACACCATGGGGAAGGTGAAG-3' | 1 |
| Reverse primer 2 | 5'-GTCTGACCACTCTACATCCGAGG AGGTGACCAGGCGCCCAATA-3' | 2 |
| Forward primer 1 | 5'-GACTGAGAGCGGGTGACGTCGAG ATGGCGACCTGGAAGTCCAA-3' | 3 |
| Reverse primer 2 | 5'-GTCTGACCACTCTACATCCGAGG AGTTGTCTGCTCCCACAATGAAAC-3' | 4 |
| Detection probe | 5'-FAM-CTCCTCGGATGTAGAGTGG TCAGAC-BHQ1-PEG-GACTGAGAGC GGGTGACGTCGAGAT-3' | 5, 12 |

The detection step was carried out by adding the detection probe and DNA polymerase under conditions in which the probe extends and copies the template until it digests the 5' end of its own probe sequence, resulting in the release of the fluorophore. The amplicon-extended probe complex is then denatured and a new detection probe was allowed to anneal to the amplicon, repeating the extension and generation of signal. This was accomplished using a thermocycling profile of heating to 95° C.-10 min and 50 cycles of 95° C. for 5 sec (denaturation), then cooling the solution to 60° C. for 2.0 m, (extension) and detecting signal using an Applied BioSystems 7900HT real-time PCR instrument. FIG. 31 shows that a concentration dependent response in fluorescence signal was detected. Reactions carried out in this way demonstrate an increase in fluorescence in concentration dependent manner with two different target sequences. See FIG. 31 showing Encode Set 1 (GAPDH) and Encode Set 2 (RPLPO). As demonstrated the highest concentration of pre-amplified cDNA was detectable with a maximal signal reached in the first 20 cycles, in contrast a 10 fold lower concentration of cDNA, while detectable, did not reach maximal signal through 50 rounds of thermocycling. Compared to the negative control, which did not generate an increase in fluorescence, both samples that contained cDNA were clearly detectable.

3.8 Illustration 8: Assays Using an Extendible Probe and a Single Decoding Primer FIG. 32 illustrates an embodiment in which a single decoding primer is used to both detect and amplify the template strand during the detection step. As illustrated, an initial encoding amplification associates each target sequence with a pair of probe-binding sequences, denoted Bu and Du. The encoding primers have the structure 5'-Du-Lf-3' (forward encoding primer) and 5'-Ci-Bu'-Lr-3' (reverse encoding primer). The amplicons are combined with a FRET-type detection probe having the structure 5'-Bu-PI-Du-3', where "PI" denotes a linker. A DNA polymerase with 5' nuclease activity is used to extend the detection probe at the 3' end using the amplicon as template, eventually cleaving the signal moiety (reporter) from the detection probe, resulting in a detectable change in the fluorescent signal. As shown in the figure, extension of the probe continues after the reporter is released and terminates at the linker moiety.

The signal generated in this process may be, and preferably is, increased by amplifying the probe extension product. The probe extension product may be amplified by denaturing the double-stranded amplicon-probe extension product complex, and amplifying the probe extension product using a primer set comprising the detection probe (forward primer) and a single indexing primer (denoted Ci in the figure) ("reverse decoding primer"). The amplicon-extended probe complex is then denatured and a new detection probe was allowed to anneal to the amplicon, repeating the extension and generation of signal. In this example the sample cDNA generated from the encoding reaction were used in a PCR thermocycle profile comprising: 50° C.-2 min, 95° C.—10 min, 2 cycles of 95° C.—5 sec, 64° C.-12 min and 40 cycles of 96° C.-5 sec, 60° C.-1 min and detecting signal using an Applied BioSystems 7900HT real-time PCR instrument. FIG. 34B shows that a concentration dependent response in fluorescence signal was detected. Using this process a encoding and decoding reaction can be carried out to perform detection of target sequence. In this example four concentrations of the 10× serially diluted cDNA (obtained from BioChain) generated from the encoding reaction (FIG. 32) were used in the reactions. The reactions produce data that generate a linear response ($r^2$=0.994 based on Ct value) to the cDNA.

4. Illustration 9

Detection of MicroRNAs

In one aspect of the invention, the universal probe assays disclosed herein may be used to detect microRNAs (miRNAs), or other short RNA molecules.

miRNAs are short (on average 22 nucleotides) ribonucleic acid molecules that bind to complementary sequences on target messenger RNA transcripts (mRNAs), usually resulting in translational repression and gene silencing. MiRNAs may also have roles in transcript degradation and sequestering, translational suppression, and transcriptional and translational activation. There are currently over 10,000 miRNAs that have been identified in a range of species including metazoa, mycetozoa, viridiplantae, and viruses. The human genome may encode over 1000 miRNAs which may target about 60% of mammalian genes and are abundant in many human cell types. Assays for miRNAs may provide miRNA fingerprints (e.g., tissue, cell or disease state-specific). See, e.g., Sayed and Abdellatif, 2011, "MicroRNAs in development and disease" *Physiol Rev.* 91:827-87; Lundstrom, 2011, "Micro-RNA in disease and gene therapy" *Curr Drug Discov Technol.* 8:76-86; Mostert et al., 2011, "Diagnostic applications of cell-free and circulating tumor cell-associated miRNAs in cancer patients" *Expert Rev Mol Diagn* 11:259-75; Ambros et al., 2003, "A uniform system for microRNA annotation," *RNA* 9 (3): 277-279. Such fingerprints may be used for classification of disease states as well as other uses that will be apparent to those of skill in the art.

Due to the short length of miRNA molecules, the design of conventional real time PCR assays is challenging. In one aspect, the present invention overcomes these difficulties and provides other advantages using template directed amplification steps (rather then, for example, primer directed PCR). In template directed amplification, a synthetic template is used in the first step to amplify an RNA sequence. As described in detail below, the template can contain multiple regions of sequence that code for various functionalities, for example the encoding of a universal probe assay. The initial reaction proceeds by creating a synthetic template that is complementary to a short RNA sequence, such as a microRNA. These methods are particularly suited for analysis of miRNA but in some embodiments can be applied to assays for any short RNAs (e.g., 16-30 bases, sometimes 18-24 bases, most often 22 bases) as well as other RNAs capable of priming synthesis on a DNA template. In some embodiments the RNA assayed for is not a transfer RNA.

Figure 35:
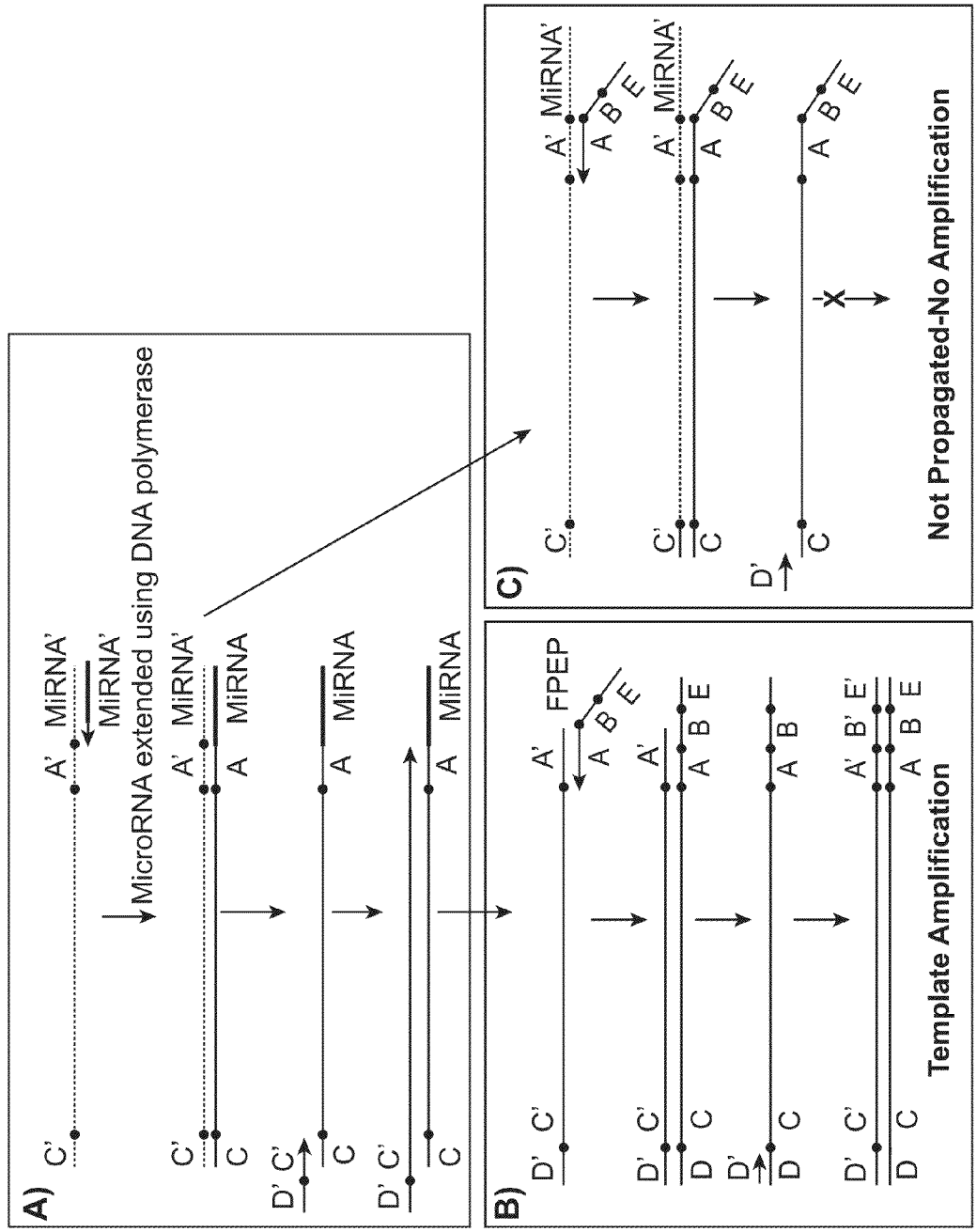
FIG. 35 shows an assay for miRNA.
Figure 36:
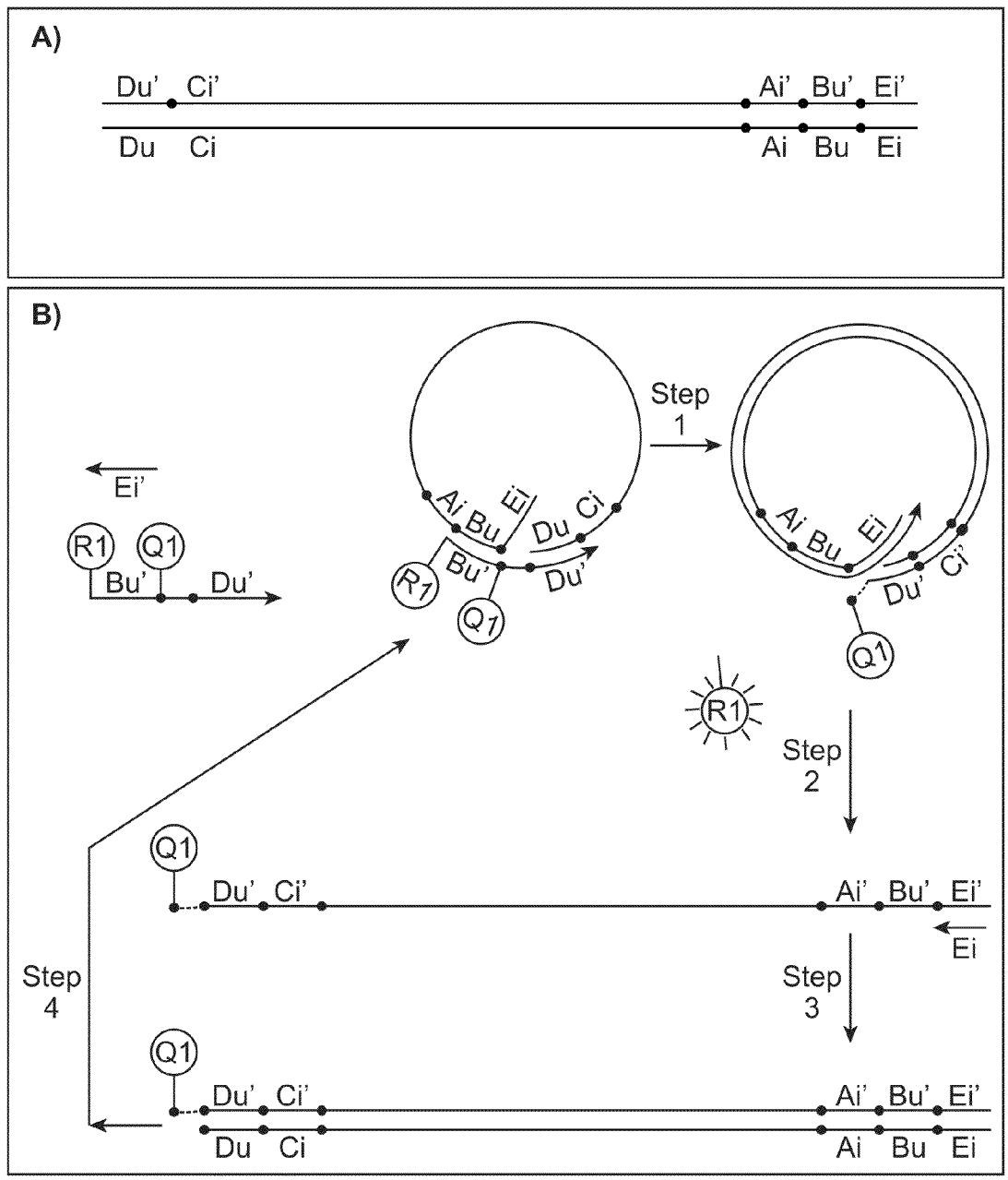
FIG. 36 shows an exemplary detection step of an assay for miRNA.

For illustration and not limitation, exemplary assays are illustrated in FIGS. 35 and 36. It will be recognized that the figures are for illustration of general approaches, and that the invention is not limited to any particular embodiments illustrated.

In one aspect, the invention provides a method for specific detection of a microRNA, comprising: (a) combining (i) a sample comprising the microRNA, (ii) an artificial DNA template comprising a first sequence that is complementary to the microRNA and a second sequence that is 3' to the first sequence, (iii) reagents for DNA-dependent extension of an RNA primer including a polymerase; thereby producing an extension combination; (b) exposing the extension combination to conditions under which the microRNA anneals to the DNA template and the microRNA is extended by the polymerase thereby producing a chimeric polynucleotide comprising a 5' microRNA portion and a 3' DNA portion complementary to the second sequence; and (c) detecting the production of the chimeric polynucleotide.

FIG. 35 provides an illustration of this approach. Panel A shows an miRNA annealed to an artificial DNA template comprising a complementary sequence (miRNA'). The complementary sequence may be complementary to the entire length of the miRNA (e.g., 22 bases) or a portion thereof including the 3' terminus of the miRNA. Although absolute complementarity is generally preferred, in some cases less than complete complementarity (sufficient for annealing of the miRNA to the template) is used. In certain embodiments less than complete complementarity is useful, for example, to detect multiple closely related miRNAs using the same template.

Extension of the miRNA primer results in a double-stranded polynucleotide in which one stand is the synthetic DNA template and the second strand is a chimeric polynucleotide comprising a 5' microRNA portion and a 3' DNA portion. Extension of the miRNA primer may be accomplished using any of a variety of DNA polymerases capable of extending an RNA primer. These include, for example, DNA polymerase I of *Thermus aquaticus* (Taq polymerase) or *Thermus thermophilus* (Tth polymerase). In some cases a thermostable polymerase is used. In other cases, a polymerase that is inactivated at elevated temperature (e.g. 95° C., 5 min.) is preferred. In some cases, the polymerase does not have reverse transcriptase (RNA dependent DNA polymerase) activity. In certain embodiments, a conditions can be selected such that a polymerase (such as Tth polymerase) copies the miRNA portion of the chimeric polynucleotide (e.g., in the presence of Mn ion; see Myers and Gelfand, 1991, *Biochemistry*, 30:7661-66).

The invention contemplates any number of approaches to detecting the production of the chimeric polynucleotide. One approach comprises amplifying at least a region of the DNA portion of chimeric polynucleotide and detecting the amplification product. FIG. 35 illustrates copying the DNA portion of the chimeric polynucleotide using a forward extension primer with the structure 5'-Y-3' (wherein Y is a sequence complementary to the DNA portion of the chimeric polynucleotide) or 5'-Z-Y'-3' (or, 5'-D'-C', as shown in the figure).

While the production of the forward primer extension product (FPEP) can be directly detected by art known methods, further amplification is generally preferred. When further amplification is contemplated, the forward primer may include a 5' tag sequence (Z or D') in addition to the sequence complementary to the DNA portion of the chimeric polynucleotide (Y or C'). Generally, the forward primer will hybridize at or near the 3' end of the chimeric polynucleotide, but it will be recognized this is not necessarily required.

In embodiments in which further amplification steps are used to detect the chimeric polynucleotide, the double-stranded polynucleotide (illustrated at the bottom of Panel A) is denatured and the DNA portion of the forward primer extension product is amplified using a forward amplification primer and a reverse amplification primer (see Panel B). This amplification can be detected directly by art-known methods and/or methods described herein.

Panel B of FIG. 35 illustrates detecting the forward extension primer extension product (and by extension, the production of the chimeric polynucleotide) by amplifying the forward extension primer extension product using a forward amplification primer and a reverse amplification primer. The forward amplification primer may be the same as the forward extension primer (e.g., D'C' in the figure). It is preferred, however, that the forward amplification primer has the sequence of the 5' tag sequence (Z or D') or a similar sequence that hybridizes to the complement of 5' tag sequence. As is illustrated in Panel C, this approach reduces or eliminates "background" amplification of the synthetic DNA template.

In FIG. 35 the reverse amplification primer is denoted 5'-E-B-A-3', but it will be recognized that any primer that results in a detectable amplification product may be used. In addition, although the reverse amplification primer shown in FIG. 35 anneals to the 3' end of the forward primer extension product, the reverse amplification primer could, alternatively, anneal at an upstream portion. Any primer pair that specifically amplifies at least some of the forward primer extension product may be used. Using extension and amplification primers that anneal near a terminus of a substrate polynucleotide is generally advantageous insofar as a shorter artificial DNA template may be used in the assay.

As noted, Panel B shows a reverse amplification primer having the structure ABE. As will be recognized and as illustrated in FIG. 36, this structure facilitates detection of the amplification product (and, by extension, the production of the chimeric polynucleotide and the presence or amount of the miRNA).

The process outlined in FIG. 35 can be carried out in a variety of formats, including microfluidic formats. In one approach, the steps in Panel A ("extension steps") are carried out in one reaction volume (e.g., in a single tube, well or chamber) and the reactions of Panel B ("amplification steps") are carried out in a different reaction volume or volumes. In another approach, the extension and amplification steps are carried out in the same reaction volume.

Generally, when the forward extension primer and forward amplification primer are different, the concentration of the forward extension primer is minimized in the amplification steps. This can be accomplished in any of several ways known in the art including one of more of:

(a) using a low concentration of the forward extension primer in the extension steps;

(b) using size selection to completely or partially remove small (primer-size) single stranded molecules, including the forward extension primer, after formation of the double-stranded polynucleotide having a synthetic DNA template strand and a chimeric polynucleotide strand) and then adding the forward amplification primer;

(c) removing single-stranded molecules (including the forward extension primer) by introducing an exonuclease (e.g., exonuclease 1, RecJf) or combinations of exonucleases which digest single-stranded DNA from the 5' and/or 3' ends after formation of the double-stranded polynucleotide;

(d) using forward extension primer(s) bound to a bead, magnetic particle, or other substrate, and removing the forward extension primer(s) at the desired time using art-known methods;

(e) removing forward extension primer(s) based on their sequences (e.g., by hybridization to an immobilized capture sequence;

(f) substituting dUTP for dTTP in the artificial template, and pretreating the product of the miRNA extension reaction with uracil N-glycosylase (UNG) prior to PCR amplification to eliminate template carryover.

Although discussed above in relation to detecting a specific miRNA, it will be immediately apparent to those of skill in the art that the methods of the invention may be applied to detection of multiple miRNAs in a sample (e.g., at least 2, at least 3, at least 10, at least 25, at least 100 or at least 500 different miRNA sequences). In one approach, "multiplex" extension reactions for multiple (i.e., "N") miRNAs on multiple artificial DNA templates are carried out in a reaction volume, resulting in "N" double-stranded molecules; the double-stranded molecules are amplified and products detected. In one approach, detection is carried out as a multiplex analysis (e.g., "N" different amplification products are detected in a single reaction volume. Alternatively, the extension reaction can be distributed to at least "N" different aliquots and each aliquot can be interrogated for the presence signal corresponding to a single miRNA. In another approach, the extension reaction can be distributed to fewer than "N" different aliquots, and each aliquot can be interrogated for the presence signal corresponding to a multiple miRNA. For example, if N=100, the extension reaction can be distributed to 10 aliquots, each of which can be interrogated for the presence of signals corresponding to ten miRNA sequences. In yet another embodiment, several different extension reactions can be carried out, each with a subset of the "N' miRNAs of interest. It will be appreciated that numerous approaches consistent with the present invention can be used.

FIG. 36 illustrates detection of the double-stranded product using assay methods disclosed hereinabove. It will be understood that any of the assay approaches disclosed herein may be used to detect miRNAs, and that the particular approach of FIG. 36 is for illustration and not limitation. In Panel A, the double-stranded product of the amplification step is shown. This product corresponds to the double-stranded product of the amplification step in FIG. 35 Panel B, except that subscripts "u" (universal) and "I" (indexing) are added.

As noted hereinabove, a "sample" refers to a composition containing a target polynucleotide. Without limitation exemplary samples from may contain miRNAs obtained from humans, non-human animals, plants, fungi and bacteria. In some embodiments the sample comprises miRNA from a single cell type or a single tissue type. In some examples, the sample comprises miRNA from a single cell (e.g., a tumor cell, stem cell or fetal cell). In some embodiments, the sample comprises cell-free miRNA (e.g., obtained from blood, urine, spinal fluid, amniotic fluid, breast milk and the like). In some embodiments, the sample comprises cell-free miRNA obtained from blood or plasma of a pregnant female.

In various embodiments, a biological material may be processed (e.g., cells removed, miRNA enriched or purified, reagents such as buffers, RNase inhibitors, etc. added) prior to analysis.

In some embodiments, the microRNA that is detected is 21-23 bases in length (typically 22 bases in length). In some embodiments the microRNA is not phosphorylated at the 3' terminus. In some embodiments the microRNA is phosphorylated at the 3' terminus and detecting optionally comprises removing the 3' phosphate from the miRNA prior to extending the RNA primer. Art-known methods, including treatment with a phosphatase (e.g., a polynucleotide 3' phosphatase [EC 3.1.3.32]) may be used to remove a 3' phosphate.

As noted above, the sample comprising the microRNA is combined with the artificial DNA template and reagents for DNA-dependent extension of an RNA primer including a polymerase; thereby producing an extension combination.

The artificial DNA template used in assays of the invention may vary in length or properties. Generally, the length of the artificial DNA template is 40-500 bases, more often 45-300 bases, even more often 45-100 bases and often about 60 bases. The phrase "DNA template" is used to distinguish the template from the RNA (e.g., miRNA) primer, but is not intended to limit the structure of the template to deoxyribonucleotides. Thus, the term "artificial nucleic acid" may also be used. In some embodiments the template contains only deoxyribonucleotides. In some embodiments, the template may contain nonstandard or artificial nucleotides or linkages provided an miRNA of interest can anneal to and be extended by a DNA-dependent DNA polymerase. Thus, in some embodiments an artificial DNA template may comprise inosine, methylcytosine, dUTP (in place of dTTP) or other bases, uncharged or modified linkages (e.g., methyl phosphonates, phosphotriesters, phosphoamidates, carbamates, alpha anomeric nucleic acids and the like), synthetic molecules that mimic polynucleotides in their ability to bind to a designated sequence via hydrogen bonding and other chemical interactions, and the like. In some embodiments the DNA template may comprise one or more ribonucleotides. In some cases the artificial DNA template will contain a blocker on the 3' end (e.g., to prevent the template from priming other reactions, e.g., during the extension step or subsequent steps). Examples of blockers include 3'-$PO_4$, carbon spacers, and PEG.

Reagents for DNA-dependent extension of an RNA primer include a DNA polymerase capable of extending a RNA primer, and other reagents required for extension. The precise content of the extension combination will vary based on the choice of the polymerase and other factors, but will generally include deoxyribonucleic acid triphosphates (dNTPs), buffer, divalent ions (e.g., Mg++), chelator(s) (e.g., EDTA), RNAse or protease inhibitors, detectable labels, and the like. It will be well within the ability of those of skill in the art to select reagents for extension and amplification. Likewise, those of skill in the art be able to select conditions for extension and amplification. Depending on the polymerase used and desires of the operator, extension generally occurs at a temperature in the range of 25° C. to 50° C. (and sometimes higher), and will occur under temperature and ionic conditions that allow the miRNA to anneal to the template.

In some embodiments, the extension steps are carried out using one DNA polymerase, and the amplification and/or detection steps are carried out using a different DNA polymerase. In one approach, the synthetic DNA template comprises artificial bases, the DNA polymerase used in the extension step recognizes the artificial bases, and the DNA polymerase used in the amplification step does not amplify a strand comprising these bases. DNA polymerases with appropriate specificities can be selected by those of skill in the art.

In one illustration, a sample containing Let7-microRNA (SEQ ID NO:6) is combined with a synthetic template (SEQ ID NO:7) and a reaction mix containing dNTP's, co-factors (master mix) and a DNA polymerase. The reaction is first denatured with a hot start step (95° C. for 5 min) to activate the enzyme. Upon annealing at between 50-72° C. the microRNA is extended. Once this extension is complete the 1 unit of exonuclease 1 is added to the reaction to degrade the synthetic template from the 3' end. After this digestion, a set of forward and reverse encoding primers (SEQ ID NOS:8 and 9) are added to the reaction mix and the extended microRNA is encoded for universal detection using detection probes by thermocycling the reaction 12-18 cycles of 95° C. (5 sec) and 65° C. (30 sec). When encoding is complete the reaction mix is diluted 1:100 and the universal extendable probe (SEQ ID NO:10) is added along with the indexed primer. The reaction is then monitored using a real-time PCR instrument to determine the increase in fluorescence as a function of cycle number.

TABLE 2

|  | Sequence (shown 5'→ 3') | SEQ ID NO: |
|---|---|---|
| Let7-microRNA: | UGAGGUAGGAGGUUGUAUAGUU | 6 |
| Synthetic Template | ACACCATGGGGAAGGTGAAGTA TTGGGCGCCTGGTCACAACTAT ACAACCTCCTACCTCA | 7 |
| Forward Encoding primer | GACTGAGAGCGGGTGACGTCGAG ATACACCATGGGGAAGGTGAAG | 8 |

TABLE 2-continued

|  | Sequence (shown 5'→ 3') | SEQ ID NO: |
|---|---|---|
| Reverse Encoding Primer | AGTCACCTGCGGATTAATGTGT CTGACCACTCTACATCCGAGGA GGTGACCAGGCGCCCAATA | 9 |
| Probe sequence | FAM-CTCCTCGGATGTAGAGTG GTCAGAC-BHQ1-Peg9-GACT GAGAGCGGGTGACGTCGAGAT | 10, 13 |
| Decode primer | 5'-AGTCACCTGCGGATTAATGT-3' | 11 |

While the present invention has been described with reference to the specific embodiments thereof, it should be understood by those skilled in the art that various changes can be made and equivalents can be substituted without departing from the scope of the invention. In addition, many modifications can be made to adapt a particular situation, material, composition of matter, process, process step or steps, to achieve the benefits provided by the present invention without departing from the scope of the present invention. All such modification re intended to be within the scope of the claims appended hereto.

All publications and patent documents cited herein are incorporated herein by reference as if each such publication or document was specifically and individually indicated to be incorporated herein by reference. Citation of publications and patent documents is not intended as an indication that any such document is pertinent prior art, nor does it constitute any admission as to the contents or date of the same.

The invention claimed is:

1. A method for producing a labeled amplification product, said method comprising amplifying a target nucleic acid sequence to produce an amplification product comprising said target sequence, a first probe-binding sequence 5' to the target sequence, and a second probe-binding sequence 3' to the target sequence, wherein the first and second probe-binding sequences are not complementary to the target sequence, thereby producing an amplification product; and hybridizing a first detection probe to the amplification product, said first detection probe comprising a first segment that hybridizes to the first probe-binding sequence and a second segment that hybridizes to the second probe-binding sequence, wherein the first and second segments of the first detection probe are joined by an intervening non-nucleotide linker or an intervening non-hybridizing nucleotide linker, thereby producing a labeled amplification product.

2. The method of claim 1 wherein the target nucleic acid sequence is amplified by the polymerase chain reaction or the ligase chain reaction.

3. The method of claim 1 wherein the first detection probe comprises a fluorescent dye.

4. The method of claim 3 wherein the first detection probe is a fluorescence resonance energy transfer (FRET) probe comprising a reporter dye and a quencher dye.

5. The method of claim 3 wherein the first detection probe is a molecular beacon probe.

6. The method of claim 1 wherein the target nucleic acid sequence is one of a plurality of distinct target nucleic acid sequences in a sample.

7. The method of claim 1 further comprising combining the labeled amplification product with a first primer under conditions in which said primer anneals to the amplification product and is extended by a DNA polymerase with 5' nuclease activity, wherein said extension causes the release of a reporter dye or a quencher dye from the first detection probe or causes the release of the first detection probe from the labeled amplification product.

8. The method of claim 7 further comprising additional rounds of amplification of the target sequence.

9. The method of claim 8 wherein said additional rounds comprise PCR amplification with the first primer and a reverse primer.

10. The method of claim 6 further comprising producing a second labeled amplification product, said method comprising
   amplifying a second target nucleic acid sequence to produce a second amplification product comprising said second target sequence, a third probe-binding sequence 5' to the second target sequence, and a fourth probe-binding sequence 3' to the second target sequence, thereby producing a second amplification product; and
   hybridizing a second detection probe to the second amplification product, said second detection probe comprising a first segment that hybridizes to the third probe-binding sequence and a second segment that hybridizes to the fourth probe-binding segment, thereby producing a second labeled amplification product.

11. The method of claim 10 wherein the third probe-binding sequence is the same as the first probe-binding sequence and the fourth probe-binding sequence is the same as the second probe-binding sequence and a single detection probe binds both the first and second amplification products.

12. The method of claim 10 wherein the first and second detection probes comprise different reporter dyes.

13. The method of claim 10 wherein the third probe-binding sequence is not the same as the first probe-binding sequences and/or the fourth probe-binding sequence is not the same as the second-probe binding sequence.

14. A method comprising
   (a) combining
      (1) a target polynucleotide;
      (2) a first encoding primer, wherein the first encoding primer comprises
         a first target-binding sequence complementary to and capable of binding to a first primer-binding sequence (PBS) of the target polynucleotide and
         a first probe-binding sequence not complementary to the target polynucleotide sequence at a position adjacent to said first PBS; and,
      (3) a second encoding primer, wherein the second encoding primer comprises
         a second target-binding sequence complementary to and capable of binding to a second PBS of the target polynucleotide and
         a second probe-binding sequence not complementary to the target polynucleotide sequence at a position adjacent to said second PBS;
   (b) exposing the combination produced in step (a) to amplification conditions, thereby producing amplicons comprising the target polynucleotide sequence bounded by the first probe-binding sequence and the second probe-binding sequence or the complement of the second probe-binding sequence; and
   (c) detecting the amplicon by hybridizing a detection probe to the amplicon, which detection probe binds both of (i) the first probe-binding sequence and (ii) the second probe-binding sequence or the complement of the second probe-binding sequence, and wherein the detection probe does not hybridize to the target polynucleotide sequence.

15. The method of claim 14 wherein the target polynucleotide is double stranded, the first target-binding sequence is located at the 3' terminus of the first encoding primer, the second target-binding sequence is located at the 3' terminus of the second encoding primer, and the first and second primer binding sequences are on different strands of the target polynucleotide.

16. The method of claim 14 wherein the amplification conditions are PCR amplification conditions.

17. The method of claim 14 wherein the target polynucleotide is double stranded, the first target-binding sequence is located at the 3' terminus of the first encoding primer, the second target-binding sequence is located at the 5' terminus of the second encoding primer, and the first and second primer binding sequences are on the same strand of the target polynucleotide.

18. The method of claim 17 wherein the amplification conditions are LCR amplification conditions.

19. The method of claim 14 wherein the first encoding primer comprises the first target-binding sequence, the first probe-binding sequence, and a first indexing sequence, and the second encoding primer comprises the second target-binding sequence, the second probe-binding sequence, and a second indexing sequence,
   and wherein the target sequence is further amplified using
      a forward primer comprising the first probe binding sequence, and the first indexing sequence, and
      a reverse primer comprising the second probe binding sequence, and the second indexing sequence.

20. The method of claim 19 wherein in the second encoding primer the second probe binding sequence is between the second target binding sequence and the second indexing sequence.

21. A method of detecting the presence of a double stranded or partially double stranded target polynucleotide in a sample, comprising:
   (a) contacting the target polynucleotide with a first encoding primer and a second encoding primer,
   wherein the first encoding primer comprises a first target-binding sequence complementary to and capable of hybridizing to a first primer binding sequence of the target polynucleotide, and a first probe binding sequence, wherein the second encoding primer comprises a second target-binding sequence complementary to and capable of hybridizing to a second primer binding sequence portion of the target polynucleotide, and a second probe binding sequence, wherein the first and second primer binding sequences are on complementary strands of the target polynucleotide, and wherein the first and second probe binding sequences are not complementary to the target polynucleotide sequence;

(b) amplifying a double-stranded target sequence between and including the first and second primer binding sequences to produce an amplification product comprising the first and second probe binding sequences;

(c) contacting the amplification product with a detection probe, such that the detection probe binds to both the first probe binding sequence and the complement of the second probe binding sequence, wherein the detection probe does not hybridize to the target polynucleotide sequence; and (d) detecting said binding, thereby determining that the target polynucleotide is present in the sample.

22. A method of detecting the presence of a target polynucleotide sequence in a sample, comprising:

a) amplifying the target polynucleotide sequence to produce an amplicon comprising the target polynucleotide sequence flanked by a first probe-binding sequence and a second probe-binding sequence, wherein the first and second probe-binding sequences are not complementary to the target polynucleotide sequence;

b) hybridizing a detection probe to the amplicon to form a detection probe-amplicon complex, wherein the detection probe comprises a first segment that hybridizes to the first probe-binding sequence, a second segment that hybridizes to the second probe-binding sequence, an extendible 3'-terminus, and a signal moiety positioned 5' to the extendible 3' terminus, and wherein the detection probe does not hybridize to the target polynucleotide sequence; and c) maintaining the detection probe-amplicon complex in the presence of DNA polymerase having 5' nuclease activity under extension reaction conditions, wherein the extendible 3' terminus of the detection probe is extended, wherein the amplicon acts as the template for the extension reaction, and wherein the 5' terminus of the detection probe is hydrolyzed by the nuclease activity and the signal moiety is released from the detection probe-amplicon complex and detected.

23. The method of claim 22 wherein the extension reaction produces an amplifiable polynucleotide, and the method further comprises amplifying the polynucleotide using a forward primer and a reverse primer.

24. The method of claim 23 wherein the detection probe comprises the forward primer.

25. The method of claim 22 wherein step (a) comprises amplifying the target polynucleotide sequence using a first encoding primer with the structure 5'-$P_1$-$I_1$-$T_1$-3', wherein $P_1$ is the first probe-binding sequence, $I_1$ is a first indexing sequence and $T_1$ is a first target-binding sequence, and a second encoding primer with the structure 5'-$I_2$-$P_2$-$T_2$-3', wherein $I_2$ is a second indexing sequence, $P_2$ is the second probe-binding sequence and $T_2$ is a second target-binding sequence.

26. A method of detecting the presence of a target polynucleotide sequence in a sample, comprising:

a) amplifying the target polynucleotide sequence to produce an amplicon comprising the target polynucleotide sequence flanked by a first probe-binding sequence, a second probe-binding sequence, and an indexing sequence, wherein the first probe binding sequence, second probe binding sequence, and indexing sequence are not complementary to the target polynucleotide sequence, b) hybridizing a detection probe to the amplicon to form a detection probe-amplicon complex, wherein the detection probe comprises a first segment that hybridizes to the first probe-binding sequence, a second segment that hybridizes to the second probe-binding sequence, a non-extendible 3'-terminus, and a signal moiety positioned 5' to the non-extendible 3' terminus, and wherein the detection probe does not hybridize to the target polynucleotide sequence, and c) maintaining the detection probe-amplicon complex in the presence of a DNA polymerase having 5' nuclease activity and an indexing primer that hybridizes to a sequence in the amplicon that is complementary to the indexing sequence under extension reaction conditions, wherein the indexing primer is extended, wherein the amplicon acts as the template for the extension reaction, and wherein the 5' terminus of the detection probe is hydrolyzed by the nuclease activity and the signal moiety is released from the detection probe-amplicon complex and detected.

* * * * *

SEQUENCE LISTING

```
<160> NUMBER OF SEQ ID NOS: 13

<210> SEQ ID NO 1
<211> LENGTH: 45
<212> TYPE: DNA
<213> ORGANISM: Artificial Sequence
<220> FEATURE:
<223> OTHER INFORMATION: Synthetic DNA forward primer

<400> SEQUENCE: 1
gactgagagc gggtgacgtc gagatacacc atggggaagg tgaag         45

<210> SEQ ID NO 2
<211> LENGTH: 43
<212> TYPE: DNA
<213> ORGANISM: Artificial Sequence
<220> FEATURE:
<223> OTHER INFORMATION: Synthetic DNA reverse primer

<400> SEQUENCE: 2
gtctgaccac tctacatccg aggaggtgac caggcgccca ata           43

<210> SEQ ID NO 3
<211> LENGTH: 43
<212> TYPE: DNA
<213> ORGANISM: Artificial Sequence
<220> FEATURE:
<223> OTHER INFORMATION: Synthetic DNA forward primer

<400> SEQUENCE: 3
gactgagagc gggtgacgtc gagatggcga cctggaagtc caa           43
```

```
<210> SEQ ID NO 4
<211> LENGTH: 47
<212> TYPE: DNA
<213> ORGANISM: Artificial Sequence
<220> FEATURE:
<223> OTHER INFORMATION: Synthetic DNA reverse primer

<400> SEQUENCE: 4
gtctgaccac tctacatccg aggagttgtc tgctcccaca atgaaac                47

<210> SEQ ID NO 5
<211> LENGTH: 25
<212> TYPE: DNA
<213> ORGANISM: Artificial Sequence
<220> FEATURE:
<223> OTHER INFORMATION: Synthetic DNA detection probe
<220> FEATURE:
<221> NAME/KEY: misc_feature
<222> LOCATION: (1)..(1)
<223> OTHER INFORMATION: 5' c modified by FAM
<220> FEATURE:
<221> NAME/KEY: misc_feature
<222> LOCATION: (25)..(25)
<223> OTHER INFORMATION: 3' c modified by BHQ1 and PEG linker to SEQ ID
      NO:12

<400> SEQUENCE: 5
ctcctcggat gtagagtggt cagac                                        25

<210> SEQ ID NO 6
<211> LENGTH: 22
<212> TYPE: RNA
<213> ORGANISM: Artificial Sequence
<220> FEATURE:
<223> OTHER INFORMATION: Synthetic RNA

<400> SEQUENCE: 6
ugagguagga gguuguauag uu                                           22

<210> SEQ ID NO 7
<211> LENGTH: 60
<212> TYPE: DNA
<213> ORGANISM: Artificial Sequence
<220> FEATURE:
<223> OTHER INFORMATION: Synthetic DNA template

<400> SEQUENCE: 7
acaccatggg aaggtgaag tattgggcgc ctggtcacaa ctatacaacc tcctacctca   60

<210> SEQ ID NO 8
<211> LENGTH: 45
<212> TYPE: DNA
<213> ORGANISM: Artificial Sequence
<220> FEATURE:
<223> OTHER INFORMATION: Synthetic DNA forward encoding primer

<400> SEQUENCE: 8
gactgagagc gggtgacgtc gagatacacc atggggaagg tgaag                  45

<210> SEQ ID NO 9
<211> LENGTH: 63
<212> TYPE: DNA
<213> ORGANISM: Artificial Sequence
<220> FEATURE:
<223> OTHER INFORMATION: Synthetic DNA reverse encoding primer
```

```
<400> SEQUENCE: 9
agtcacctgc ggattaatgt gtctgaccac tctacatccg aggaggtgac caggcgccca    60
ata                                                                  63

<210> SEQ ID NO 10
<211> LENGTH: 25
<212> TYPE: DNA
<213> ORGANISM: Artificial Sequence
<220> FEATURE:
<223> OTHER INFORMATION: Synthetic DNA forward primer
<220> FEATURE:
<221> NAME/KEY: misc_feature
<222> LOCATION: (1)..(1)
<223> OTHER INFORMATION: 5' c modified by FAM
<220> FEATURE:
<221> NAME/KEY: misc_feature
<222> LOCATION: (25)..(25)
<223> OTHER INFORMATION: 3' c modified by BHQ1 and Peg9 linker to SEQ
      ID NO:13

<400> SEQUENCE: 10
ctcctcggat gtagagtggt cagac                                          25

<210> SEQ ID NO 11
<211> LENGTH: 20
<212> TYPE: DNA
<213> ORGANISM: Artificial Sequence
<220> FEATURE:
<223> OTHER INFORMATION: Synthetic DNA decode primer

<400> SEQUENCE: 11
agtcacctgc ggattaatgt                                                20

<210> SEQ ID NO 12
<211> LENGTH: 25
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (1)..(1)
<223> OTHER INFORMATION: 5' g connected to PEG linker of SEQ ID NO:5

<400> SEQUENCE: 12
gactgagagc gggtgacgtc gagat                                          25

<210> SEQ ID NO 13
<211> LENGTH: 25
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (1)..(1)
<223> OTHER INFORMATION: 5' g connected to Peg9 linker of SEQ ID NO:10

<400> SEQUENCE: 13
gactgagagc gggtgacgtc gagat                                          25
```